(12) United States Patent
Mattei et al.

(10) Patent No.: US 6,686,381 B2
(45) Date of Patent: Feb. 3, 2004

(54) THIAZOLE DERIVATIVES

(75) Inventors: Patrizio Mattei, Riehen (CH); Werner Neidhart, Hagenthal le Bas (FR); Matthias Heinrich Nettekoven, Grenzach-Wyhlen (DE); Philippe Pflieger, Schwoben (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/374,573

(22) Filed: Feb. 26, 2003

(65) Prior Publication Data

US 2003/0225141 A1 Dec. 4, 2003

(30) Foreign Application Priority Data

Feb. 28, 2002 (EP) .............................................. 02004296

(51) Int. Cl.$^7$ ..................... A61K 31/425; C07D 277/42
(52) U.S. Cl. ........................................ 514/370; 548/194
(58) Field of Search ............................ 548/194; 514/370

(56) References Cited

U.S. PATENT DOCUMENTS

| | | |
|---|---|---|
| 4,598,089 A | 7/1986 | Hadvary et al. |
| 4,931,463 A | 6/1990 | Barbier et al. |
| 4,983,746 A | 1/1991 | Barbier et al. |
| 5,399,720 A | 3/1995 | Karpf et al. |
| 6,004,996 A | 12/1999 | Shah et al. |

| | | | |
|---|---|---|---|
| 2001/0039275 A1 | * 11/2001 | Bowler et al. | ............ 514/235.5 |

FOREIGN PATENT DOCUMENTS

| | | | |
|---|---|---|---|
| EP | 0 815 359 | 6/1986 | |
| EP | 0 189 577 | 8/1986 | |
| EP | 0 443 449 | 8/1991 | |
| EP | 0 524 495 | 1/1993 | |
| WO | WO 99/34786 | 7/1999 | |
| WO | WO 99 62892 | 12/1999 | |
| WO | WO 00/09122 | 2/2000 | |
| WO | WO 00/09123 | 2/2000 | |
| WO | WO 01 64675 | 9/2001 | |
| WO | WO2003011843 | * 2/2003 | ................. 548/192 |

* cited by examiner

*Primary Examiner*—Robert Gerstl
(74) *Attorney, Agent, or Firm*—George W. Johnston; Dennis P. Tramaloni; Eileen M. Ebel

(57) ABSTRACT

Compounds of formula I are provided

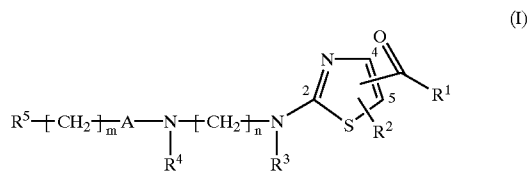

as well as pharmaceutically acceptable salts and esters thereof, wherein $R^1$ to $R^5$, n, m and A have the significance disclosed in the specification, and can be used for the treatment or prevention of arthritis, cardiovascular diseases, diabetes, renal failure, eating disorders and obesity.

22 Claims, No Drawings

THIAZOLE DERIVATIVES

BACKGROUND OF THE INVENTION

Neuropeptide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis.

Therefore compounds that antagonize neuropeptide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on con asso-ciated risk factors such as arthritis, cardiovascular diseases, diabetes and renal failure.

SUMMARY OF THE INVENTION

The invention provides compounds of formula I and pharmaceutically acceptable salts and esters thereof

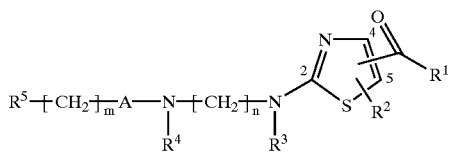

(I)

wherein
 $R^1$ is aryl or heteroaryl;
 $R^2$ is hydrogen, alkyl or cycloalkyl;
 $R^3$ is hydrogen, alkyl or cycloalkyl;
 $R^4$ is hydrogen, alkyl or cycloalkyl;
 $R^5$ is alkyl, cycloalkyl, aryl, heteroaryl;
 $R^6$ is hydrogen, alkyl or cycloalkyl;
 A is —C(O)—; —S(O)$_2$—; —N(R$^6$)—C(O)— or —O—C(O)—;
 n is 2 to 6; and
 m is zero to 2.

The compounds of formula I and their pharmaceutically acceptable salts and esters are neuropeptide ligands, for example, neuropeptide receptor antagonists and in particular, they are selective neuropeptides Y Y5 receptor antagonists.

DETAILED DESCRIPTION OF THE INVENTION

The present invention is concerned with novel thiazole derivatives useful as neuropeptide Y (NPY) receptor ligands, particularly neuropeptide Y (NPY) antagonists.

The invention provides compounds of formula I and pharmaceutically acceptable salts and esters thereof

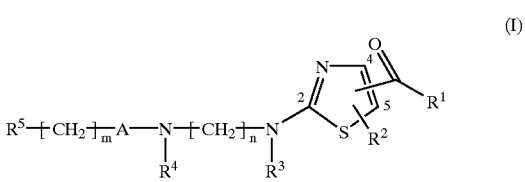

(I)

wherein
 $R^1$ is aryl or heteroaryl;
 $R^2$ is hydrogen, alkyl or cycloalkyl;
 $R^3$ is hydrogen, alkyl or cycloalkyl;
 $R^4$ is hydrogen, alkyl or cycloalkyl;
 $R^5$ is alkyl, cycloalkyl, aryl, heteroaryl;
 $R^6$ is hydrogen, alkyl or cycloalkyl;
 A is —C(O)—; —S(O)$_2$—; —N(R$^6$)—C(O)— or —O—C(O)—;
 n is 2 to 6; and
 m is zero to 2.

The compounds of formula I and their pharmaceutically acceptable salts and esters are neuropeptide ligands, for example, neuropeptide receptor antagonists and in particular, they are selective neuropeptides Y Y5 receptor antagonists.

The compounds of formula I, their salts and esters can be used in the prophylaxis or treatment of arthritis, cardiovascular diseases, diabetes, renal failure and particularly eating disorders and obesity.

Objects of the present invention are the compounds of formula I and their aforementioned salts and esters per se and their use as therapeutically active substances, a process for the manufacture of the said compounds, intermediates, pharmaceutical compositions, medicaments comprising the said compounds, their pharmaceutically acceptable salts and esters, the use of the said compounds, salts and esters for the prophylaxis and/or therapy of illnesses, especially in the treatment or prophylaxis of arthritis, cardiovascular diseases, diabetes, renal failure and particularly eating disorders such as hyperphagia and particularly obesity, and th e use of the said compounds, salts and esters for the production of medicaments for the treatment or prophylaxis of arthritis, cardiovascular diseases, diabetes, renal failure and particularly eating disorders and obesity.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl, and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and cyclopentyl.

The term "alkoxy", alone or in combination, signifies a group of the formula alkyl-O- in which the term "alkyl" has the previously given significance, such as methoxy, ethoxy, n-propoxy, isopropoxy, n-butoxy, isobutoxy, sec.butoxy and tert.butoxy, 2-hydroxyethoxy, 2-methoxyethoxy, preferably methoxy and ethoxy, and most preferred methoxy.

The term "aryl", alone or in combination, signifies a phenyl or naphthyl group, preferably a phenyl group which optionally carries one or more, preferably one to three substituents each independently selected from halogen, haloalkyl, amino, alkyl, alkoxy, aryloxy, alkylcarbonyl, cyano, carbamoyl, alkoxycarbamoyl, methylenedioxy, carboxy, alkoxycarbonyl, aminocarbonyl, alkylaminocarbonyl, dialkylaminocarbonyl, hydroxy, nitro, and haloalkoxy. Preferred substituents of aryl, preferably phenyl, are independently selected from halogen, trifluoromethyl, alkyl, alkoxy and haloalkoxy.

The term "aralkyl", alone or in combination, signifies an alkyl or cycloalkyl group as previously defined, preferably an alkyl group in which one hydrogen atom has been replaced by an aryl group as previously defined. Preferred are benzyl, benzyl substituted with hydroxy, alkoxy or halogen, preferably fluorine.

The term "heteroaryl", alone or in combination, signifies an aromatic 5- or 6-membered ring comprising 1 to 3 atoms independently selected from nitrogen, oxygen or sulfur. Optionally, the heteroaryl ring can be substituted on one or more carbon atoms with at least one substituent selected from halogen, alkyl, alkoxy and cyano. Examples of heteroaryl rings include furyl, pyridyl, 1,2-, 1,3- and 1,4-diazinyl or pyrazinyl, thienyl, isoxazolyl, oxazolyl, thiazolyl and pyrrolyl. Preferred heteroaryl rings are pyridinyl, thiophenyl and pyrazinyl which are optionally substituted with alkyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methylethylamino, pyrrolidin-1-yl or piperidino etc., preferably amino, dimethylamino and diethylamino and particularly preferred primary amino.

The term "halogen", alone or in combination, signifies fluorine, chlorine, bromine or iodine and preferably fluorine, chlorine or bromine and particularly chlorine.

The term "haloalkyl", alone or in combination, signifies an alkyl group as previously defined, wherein one or several hydrogen atoms, preferably one to three hydrogen atoms have/has been replaced by halogen. Examples of haloalkyl groups are trifluoromethyl, pentafluoroethyl and trichloromethyl. Preferred examples are trifluoromethyl and difluoromethyl. Most preferred is trifluoromethyl.

The term "haloalkoxy", alone or in combination, signifies an alkoxy group as previously defined, wherein one or several hydrogen atoms, preferably one to three hydrogen atoms have/has been replaced by halogen. A preferred example is trifluoromethoxy.

The term "cyano", alone or in combination, signifies a —CN group.

The term "nitro", alone or in combination, signifies a —NO$_2$ group.

The term —C(O)— means a carbonyl group.

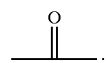

The term —S(O)$_2$— means the following group:

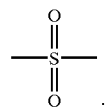

The term —N(R$^6$)—C(O)— means the following group:

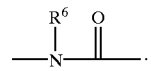

The term —O—C(O)— means the following group:

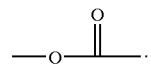

Examples of pharmaceutically acceptable salts of the compounds of formula I are salts with physiologically compatible mineral acids such hydrochloric acid, sulfuric acid or phosphoric acid; or with organic acids such as methanesulfonic acid, formic acid, acetic acid, trifluoroacetic acid, citric acid, fumaric acid, maleic acid, tartaric acid, succinic acid or salicylic acid. Preferred is oxalic acid. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes pharmaceutically acceptable solvates.

The term pharmaceutically acceptable esters of the compounds of formula I means that compounds of general formula (I) may be derivatised at functional groups to provide derivatives which are capable of conversion back to the parent compounds in vivo. Examples of such compounds include physiologically acceptable and; metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in: divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

In the nomenclature used in the present application the ring atoms of the thiazole ring are numbered as follows:

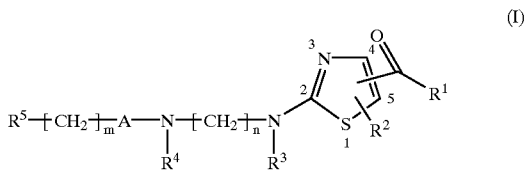

(I)

wherein $R^1$ to $R^5$, m, n and A are defined as before. In a preferred embodiment of the present invention $R^2$ is attached to the 5-position and the substituent —C(O)—$R^1$ is attached to the 4-position of the thiazole ring. Particularly preferred are the compounds of formula I, wherein the substituent —C(O)—$R^1$ is attached to the 5-position and $R^2$ is attached to the 4-position of the thiazole ring.

Preferred are compounds of formula I, wherein $R^2$ is hydrogen or alkyl. Particularly preferred are compounds of formula I, wherein $R^2$ is hydrogen or methyl. Most preferred are compounds according to formula I, wherein $R^2$ is hydrogen.

A further preferred object of the present invention are compounds of formula I, wherein $R^3$ is hydrogen or alkyl. Particularly preferred are those compounds of formula I, wherein $R^3$ is hydrogen.

Also a preferred object of the present invention are compounds of formula I, wherein $R^4$ is hydrogen or alkyl. Particularly preferred are compounds according to formula I, wherein $R^4$ is hydrogen.

Another preferred object of the present invention are compounds of formula I, wherein $R^5$ is alkyl, cycloalkyl, phenyl, phenyl substituted with one to three substituents independently selected from halogen, alkyl, alkoxy and haloalkyl, or $R^5$ is thiophenyl or thiophenyl substituted with alkyl, or $R^5$ is pyridinyl or pyridinyl substituted with alkyl or $R^5$ is pyrazinyl or pyrazinyl substituted with alkyl. Particularly preferred are compounds according to formula I, wherein $R^5$ is n-butyl, tert.butyl, cyclohexyl, thiophenyl, phenyl or phenyl substituted with one to three substituents independently selected from methyl, ethyl, methoxy, fluoro, chloro and trifluoromethyl. Further particularly preferred are compounds according to formula I, wherein $R^5$ is thiophenyl or phenyl optionally substituted with one to three substituents independently selected from alkyl, alkoxy, halogen and haloalkyl.

Preferred are compounds according to formula I, wherein $R^5$ is thiophenyl or phenyl both optionally substituted with one to three substituents independently selected from alkyl, alkoxy, halogen, haloalkyl, haloalkoxy and nitro.

A further preferred object of the present invention are compounds according to formula I, wherein $R^6$ is hydrogen.

Also preferred are compounds of formula I, wherein $R^1$ is pyridinyl or pyridinyl substituted with alkyl, or $R^1$ is thiophenyl or thiophenyl substituted with alkyl or $R^1$ is phenyl or phenyl substituted with one to three substituents independently selected from alkyl, halogen, haloalkyl or $R^1$ is pyrazinyl or pyrazinyl substituted with alkyl. Particularly preferred are compound according to formula I, wherein $R^1$ is pyridinyl, phenyl or phenyl substituted with one to three substituents independently selected from alkyl, alkoxy, halogen and haloalkyl. Very preferred are compounds of formula I, wherein $R^1$ is pyridinyl or phenyl substituted with one to three substituents independently selected from alkyl, alkoxy, halogen and haloalkyl.

A further particularly preferred object of the present invention are compounds according to formula I, wherein A is —S(O)$_2$—

Another preferred embodiment of the present invention are compounds of formula I, wherein A is —C(O)—.

Further preferred are compounds of formula I, wherein A is —N(R$^6$)—C(O)—.

Also preferred are compounds of formula I, wherein A is —O—C(O)—.

Likewise preferred are compounds of formula I, wherein n is 3 to 5. Particularly preferred are compounds of formula I, wherein n is 3. Further particularly preferred are compounds of formula I, wherein n is 5.

Preferred compounds of formula I are those, wherein m is zero or 1. Particularly preferred are those compounds of formula I, wherein m is zero. A further very preferred embodiment of this invention are compounds of formula I, wherein A is —S(O)$_2$— and m is zero.

Examples of preferred compounds of formula I are:
1. 2-Fluoro-N-{3-[5-(pyridine-2-carbonyl)-thiazol-2-ylamino]-propyl}-benzenesulfonamide
2. 2-Methoxy-5-methyl-N-{3-[5-(pyridine-2-carbonyl)-thiazol-2-ylamino]-propyl}-benzenesulfonamide
3. 2-Methoxy-5-methyl-N-{3-[5-(pyridine-3-carbonyl)-thiazol-2-ylamino]-propyl}-benzenesulfonamide
4. 2-Methoxy-5-methyl-N-{3-[5-(pyridine-4-carbonyl)-thiazol-2-ylamino]-propyl}-benzenesulfonamide
5. 2-Fluoro-N-{3-[5-(2-methyl-benzoyl)-thiazol-2-ylamino]-propyl}-benzenesulfonamide
6. 4-Methoxy-N-{3-[5-(2-methyl-benzoyl)-thiazol-2-ylamino]-propyl}-benzenesulfonamide
7. Thiophene-2-sulfonic acid {3-[5-(2-methyl-benzoyl)-thiazol-2-ylamino]-propyl}-amide
8. 2-Methoxy-5-methyl-N-{3-[5-(2-methyl-benzoyl)-thiazol-2-ylamino]-propyl}-benzenesulfonamide
9. 4-Fluoro-N-{3-[5-(2-methyl-benzoyl)-thiazol-2-ylamino]-propyl}-benzenesulfonamide
10. 2-Methyl-N-{3-[5-(2-methyl-benzoyl)-thiazol-2-ylamino]-propyl}-benzenesulfonamide
11. 3-Fluoro-N-{3-[5-(2-methyl-benzoyl)-thiazol-2-ylamino]-propyl}-benzenesulfonamide
12. 2-Chloro-N-{3-[5-(2-methyl-benzoyl)-thiazol-2-ylamino]-propyl}-5-trifluoromethyl-benzenesulfonamide
13. N-{3-[5-(2-Methyl-benzoyl)-thiazol-2-ylamino]-propyl}-benzenesulfonamide
14. 3-Methoxy-N-{3-[5-(2-methyl-benzoyl)-thiazol-2-ylamino]-propyl}-benzenesulfonamide
15. N-{3-[5-(2-Chloro-benzoyl)-thiazol-2-ylamino]-propyl}-2-fluoro-benzenesulfonamide
16. N-{3-[5-(2-Chloro-benzoyl)-thiazol-2-ylamino]-propyl}-4-methoxy-benzenesulfonamide
17. Thiophene-2-sulfonic acid {3-[5-(2-chloro-benzoyl)-thiazol-2-ylamino]-propyl}-amide
18. N-{3-[5-(2-Chloro-benzoyl)-thiazol-2-ylamino]-propyl}-2-methoxy-5-methyl-benzenesulfonamide
19. N-{3-[5-(2-Chloro-benzoyl)-thiazol-2-ylamino]-propyl}-4-fluoro-benzenesulfonamide
20. N-{3-[5-(2-Chloro-benzoyl)-thiazol-2-ylamino]-propyl}-2-methyl-benzenesulfonamide
21. N-{3-[5-(2-Chloro-benzoyl)-thiazol-2-ylamino]-propyl}-3-fluoro-benzenesulfonamide
22. 2-Chloro-N-{3-[5-(2-chloro-benzoyl)-thiazol-2-ylamino]-propyl}-5-trifluoromethyl-benzenesulfonamide
23. N-{3-[5-(2-Chloro-benzoyl)-thiazol-2-ylamino]-propyl}-benzenesulfonamide
24. N-{3-[5-(2-Chloro-benzoyl)-thiazol-2-ylamino]-propyl}-3-methoxy-benzenesulfonamide
25. {3-[5-(2-Methyl-benzoyl)-thiazol-2-ylamino]-propyl}-carbamic acid tert-butyl ester
26. {3-[5-(2-Chloro-benzoyl)-thiazol-2-ylamino]-propyl}-carbamic acid tert-butyl ester
27. {3-[5-(2-Ethyl-benzoyl)-thiazol-2-ylamino]-propyl}-carbamic acid tert-butyl ester
28. {3-[5-(2-Trifluoromethyl-benzoyl)-thiazol-2-ylamino]-propyl}-carbamic acid tert-butyl ester
29. Cyclohexanecarboxylic acid {3-[5-(2-methyl-benzoyl)-thiazol-2-ylamino]-propyl}-amide
30. Cyclohexanecarboxylic acid {3-[5-(2-ethyl-benzoyl)-thiazol-2-ylamino]-propyl}-amide
31. Pentanoic acid [3-(5-benzoyl-thiazol-2-ylamino)-propyl]-amide
32. Pentanoic acid {3-[5-(2-methyl-benzoyl)-thiazol-2-ylamino]-propyl}-amide
33. Pentanoic acid {3-[5-(2-ethyl-benzoyl)-thiazol-2-ylamino]-propyl}-amide
34. Pentanoic acid {3-[5-(2-fluoro-benzoyl)-thiazol-2-ylamino]-propyl}-amide
35. Pentanoic acid {3-[5-(2-chloro-benzoyl)-thiazol-2-ylamino]-propyl}-amide
36. N-[3-(5-Benzoyl-thiazol-2-ylamino)-propyl]-2-(4-chloro-phenyl)-acetamide
37. 2-(4-Chloro-phenyl)-N-{3-[5-(2-methyl-benzoyl)-thiazol-2-ylamino]-propyl}-acetamide
38. 2-(4-Chloro-phenyl)-N-{3-[5-(2-ethyl-benzoyl)-thiazol-2-ylamino]-propyl}-acetamide
39. Thiophene-2-carboxylic acid {3-[5-(2-methyl-benzoyl)-thiazol-2-ylamino]-propyl}-amide
40. Thiophene-2-carboxylic acid {3-[5-(2-ethyl-benzoyl)-thiazol-2-ylamino]-propyl}-amide
41. Thiophene-2-carboxylic acid {3-[5-(2-fluoro-benzoyl)-thiazol-2-ylamino]-propyl}-amide
42. Thiophene-2-carboxylic acid {3-[5-(2-chloro-benzoyl)-thiazol-2-ylamino]-propyl}-amide
43. N-{3-[5-(2-Ethyl-benzoyl)-thiazol-2-ylamino]-propyl}-2-fluoro-benzamide
44. N-{3-[5-(2-Chloro-benzoyl)-thiazol-2-ylamino]-propyl}-2-fluoro-benzamide
45. 3-Fluoro-N-{3-[5-(2-methyl-benzoyl)-thiazol-2-ylamino]-propyl}-benzamide
46. N-{3-[5-(2-Ethyl-benzoyl)-thiazol-2-ylamino]-propyl}-3-fluoro-benzamide
47. 3-Fluoro-N-{3-[5-(2-fluoro-benzoyl)-thiazol-2-ylamino]-propyl}-benzamide
48. N-{3-[5-(2-Chloro-benzoyl)-thiazol-2-ylamino]-propyl}-3-fluoro-benzamide
49. 4-Fluoro-N-{3-[5-(2-methyl-benzoyl)-thiazol-2-ylamino]-propyl}-benzamide
50. N-{3-[5-(2-Ethyl-benzoyl)-thiazol-2-ylamino]-propyl}-4-fluoro-benzamide
51. N-{3-[5-(2-Chloro-benzoyl)-thiazol-2-ylamino]-propyl}-4-fluoro-benzamide
52. N-{3-[5-(2-Methyl-benzoyl)-thiazol-2-ylamino]-propyl}-benzamide
53. N-{3-[5-(2-Ethyl-benzoyl)-thiazol-2-ylamino]-propyl}-benzamide
54. N-{3-[5-(2-Chloro-benzoyl)-thiazol-2-ylamino]-propyl}-benzamide
55. N-{3-[5-(2-Ethyl-benzoyl)-thiazol-2-ylamino]-propyl}-4-methoxy-benzamide
56. N-[3-(5-Benzoyl-thiazol-2-ylamino)-propyl]-2-methoxy-benzamide 57. N-{3-[5-(2-Ethyl-benzoyl)-thiazol-2-ylamino]-propyl}-2-methoxy-benzamide
58. 4-Chloro-N-{3-[5-(2-methyl-benzoyl)-thiazol-2-ylamino]-propyl}-benzamide
59. 4-Chloro-N-{3-[5-(2-ethyl-benzoyl)-thiazol-2-ylamino]-propyl}-benzamide
60. Cyclohexanecarboxylic acid {3-[5-(2-trifluoromethyl-benzoyl)-thiazol-2-ylamino]-propyl}-amide
61. Cyclohexanecarboxylic acid {3-[5-(4-methyl-pyridine-3-carbonyl)-thiazol-2-ylamino]-propyl}-amide
62. Pentanoic acid {3-[5-(2-trifluoromethyl-benzoyl)-thiazol-2-ylamino]-propyl}-amide
63. Pentanoic acid {3-[5-(4-methyl-pyridine-3-carbonyl)-thiazol-2-ylamino]-propyl}-amide
64. Pentanoic acid {3-[5-(2-methyl-pyridine-3-carbonyl)-thiazol-2-ylamino]-propyl}-amide
65. Pentanoic acid {3-[5-(3-methyl-thiophene-2-carbonyl)-thiazol-2-ylamino]-propyl}-amide
66. 2-(4-Chloro-phenyl)-N-{3-[5-(2-trifluoromethyl-benzoyl)-thiazol-2-ylamino]-propyl}-acetamide
67. 2-(4-Chloro-phenyl)-N-{3-[5-(3-methyl-pyridine-2-carbonyl)-thiazol-2-ylamino]-propyl}-acetamide
68. 2-(4-Chloro-phenyl)-N-{3-[5-(3-methyl-pyrazine-2-carbonyl)-thiazol-2-ylamino]-propyl}-acetamide
69. Thiophene-2-carboxylic acid {3-[5-(2-trifluoromethyl-benzoyl)-thiazol-2-ylamino]-propyl}-amide
70. Thiophene-2-carboxylic acid {3-[5-(3-methyl-pyridine-2-carbonyl)-thiazol-2-ylamino]-propyl}-amide
71. 2-Fluoro-N-{3-[5-(2-trifluoromethyl-benzoyl)-thiazol-2-ylamino]-propyl}-benzamide
72. 2-Fluoro-N-{3-[5-(3-methyl-pyrazine-2-carbonyl)-thiazol-2-ylamino]-propyl}-benzamide
73. 3-Fluoro-N-{3-[5-(2-trifluoromethyl-benzoyl)-thiazol-2-ylamino]-propyl}-benzamide
74. 3-Fluoro-N-{3-[5-(4-methyl-pyridine-3-carbonyl)-thiazol-2-ylamino]-propyl}-benzamide
75. 3-Fluoro-N-{3-[5-(3-methyl-pyridine-2-carbonyl)-thiazol-2-ylamino]-propyl}-benzamide
76. 3-Fluoro-N-{3-[5-(3-methyl-pyrazine-2-carbonyl)-thiazol-2-ylamino]-propyl}-benzamide
77. 4-Fluoro-N-{3-[5-(2-trifluoromethyl-benzoyl)-thiazol-2-ylamino]-propyl}-benzamide
78. 4-Fluoro-N-{3-[5-(4-methyl-pyridine-3-carbonyl)-thiazol-2-ylamino]-propyl}-benzamide
79. 4-Fluoro-N-{3-[5-(3-methyl-pyridine-2-carbonyl)-thiazol-2-ylamino]-propyl}-benzamide
80. 4-Fluoro-N-{3-[5-(3-methyl-thiophene-2-carbonyl)-thiazol-2-ylamino]-propyl}-benzamide
81. N-{3-[5-(2-Trifluoromethyl-benzoyl)-thiazol-2-ylamino]-propyl}-benzamide
82. N-{3-[5-(4-Methyl-pyridine-3-carbonyl)-thiazol-2-ylamino]-propyl}-benzamide
83. 4-Methoxy-N-{3-[5-(2-trifluoromethyl-benzoyl)-thiazol-2-ylamino]-propyl}-benzamide
84. 4-Methoxy-N-{3-[5-(4-methyl-pyridine-3-carbonyl)-thiazol-2-ylamino]-propyl}benzamide
85. 2-Methoxy-N-{3-[5-(2-trifluoromethyl-benzoyl)-thiazol-2-ylamino]-propyl}-benzamide
86. 4-Chloro-N-{3-[5-(2-trifluoromethyl-benzoyl)-thiazol-2-ylamino]-propyl}-benzamide
87. 4-Chloro-N-{3-[5-(4-methyl-pyridine-3-carbonyl)-thiazol-2-ylamino]-propyl}-benzamide
88. 4-Chloro-N-{3-[5-(2-methyl-pyridine-3-carbonyl)-thiazol-2-ylamino]-propyl}-benzamide
89. 1-[3-(5-Benzoyl-thiazol-2-ylamino)-propyl]-3-cyclohexyl-urea
90. 1-Cyclohexyl-3-{3-[5-(2-methyl-benzoyl)-thiazol-2-ylamino]-propyl}-urea
91. 1-Cyclohexyl-3-{3-[5-(2-ethyl-benzoyl)-thiazol-2-ylamino]-propyl}-urea
92. 1-{3-[5-(2-Chloro-benzoyl)-thiazol-2-ylamino]-propyl}-3-cyclohexyl-urea
93. 1-[3-(5-Benzoyl-thiazol-2-ylamino)-propyl]-3-butyl-urea
94. 1-Butyl-3-{3-[5-(2-methyl-benzoyl)-thiazol-2-ylamino]-propyl}-urea
95. 1-Butyl-3-{3-[5-(2-ethyl-benzoyl)-thiazol-2-ylamino]-propyl}-urea
96. 1-Butyl-3-{3-[5-(2-fluoro-benzoyl)-thiazol-2-ylamino]-propyl}-urea
97. 1-Butyl-3-{3-[5-(2-chloro-benzoyl)-thiazol-2-ylamino]-propyl}-urea
98. 1-(2-Methoxy-phenyl)-3-{3-[5-(2-methyl-benzoyl)-thiazol-2-ylamino]-propyl}-urea
99. 1-{3-[5-(2-Ethyl-benzoyl)-thiazol-2-ylamino]-propyl}-3-(2-methoxy-phenyl)-urea
100. 1-{3-[5-(2-Chloro-benzoyl)-thiazol-2-ylamino]-propyl}-3-(2-methoxy-phenyl)-urea
101. 1-(2-Fluoro-phenyl)-3-{3-[5-(2-methyl-benzoyl)-thiazol-2-ylamino]-propyl}-urea
102. 1-{3-[5-(2-Ethyl-benzoyl)-thiazol-2-ylamino]-propyl}-3-(2-fluoro-phenyl)-urea
103. 1-{3-[5-(2-Chloro-benzoyl)-thiazol-2-ylamino]-propyl}-3-(2-fluoro-phenyl)-urea
104. 1-(3-Fluoro-phenyl)-3-{3-[5-(2-methyl-benzoyl)-thiazol-2-ylamino]-propyl}-urea
105. 1-{3-[5-(2-Ethyl-benzoyl)-thiazol-2-ylamino]-propyl}-3-(3-fluoro-phenyl)-urea
106. 1-(4-Fluoro-phenyl)-3-{3-[5-(2-methyl-benzoyl)-thiazol-2-ylamino]-propyl}-urea
107. 1-{3-[5-(2-Ethyl-benzoyl)-thiazol-2-ylamino]-propyl}-3-(4-fluoro-phenyl)-urea
108. 1-[3-(5-Benzoyl-thiazol-2-ylamino)-propyl]-3-(2-chloro-benzyl)-urea
109. 1-(2-Chloro-benzyl)-3-{3-[5-(2-methyl-benzoyl)-thiazol-2-ylamino]-propyl}-urea
110. 1-(2-Chloro-benzyl)-3-{3-[5-(2-ethyl-benzoyl)-thiazol-2-ylamino]-propyl}-urea
111. 1-{3-[5-(2-Chloro-benzoyl)-thiazol-2-ylamino]-propyl}-3-(2-chloro-benzyl)-urea
112. 1-{3-[5-(2-Methyl-benzoyl)-thiazol-2-ylamino]-propyl}-3-phenyl-urea
113. 1-{3-[5-(2-Ethyl-benzoyl)-thiazol-2-ylamino]-propyl}-3-phenyl-urea
114. 1-{3-[5-(2-Chloro-benzoyl)-thiazol-2-ylamino]-propyl}-3-phenyl-urea
115. 1-Butyl-3-{3-[5-(4-methyl-pyridine-3-carbonyl)-thiazol-2-ylamino]-propyl}-urea
116. 1-{3-[5-(4-Methyl-pyridine-3-carbonyl)-thiazol-2-ylamino]-propyl}-3-phenyl-urea
117. 1-Cyclohexyl-3-{3-[5-(3-methyl-pyrazine-2-carbonyl)-thiazol-2-ylamino]-propyl}-urea
118. 1-Cyclohexyl-3-{3-[5-(3-methyl-thiophene-2-carbonyl)-thiazol-2-ylamino]-propyl}-urea
119. 4-Fluoro-N-{3-[5-(4-methyl-pyridine-3-carbonyl)-thiazol-2-ylamino]-propyl}-benzenesulfonamide
120. 4-Fluoro-N-{3-[5-(3-methyl-thiophene-2-carbonyl)-thiazol-2-ylamino]-propyl}-benzenesulfonamide
121. 2-Methoxy-5-methyl-N-{3-[5-(4-methyl-pyridine-3-carbonyl)-thiazol-2-ylamino]-propyl}-benzenesulfonamide
122. 2-Methoxy-5-methyl-N-{3-[5-(3-methyl-pyrazine-2-carbonyl)-thiazol-2-ylamino]-propyl}-benzenesulfonamide
123. 2-Methoxy-5-methyl-N-{3-[5-(3-methyl-thiophene-2-carbonyl)-thiazol-2-ylamino]-propyl}-benzenesulfonamide 124. 1-(4-Methoxy-phenyl)-3-{3-[5-(4-methyl-pyridine-3-carbonyl)-thiazol-2-ylamino]-propyl}-urea
125. {3-[4-(2-Methyl-benzoyl)-thiazol-2-ylamino]-propyl}-carbamic acid tert-butyl ester
126. N-{3-[4-(2-Methyl-benzoyl)-thiazol-2-ylamino]-propyl}-benzamide
127. 2-Fluoro-N-{3-[4-(2-methyl-benzoyl)-thiazol-2-ylamino]-propyl}-benzamide
128. 3,5-Dimethoxy-N-{3-[4-(2-methyl-benzoyl)-thiazol-2-ylamino]-propyl}-benzamide
129. Pentanoic acid {3-[4-(2-methyl-benzoyl)-thiazol-2-ylamino]-propyl}-amide
130. 1-{3-[4-(2-Methyl-benzoyl)-thiazol-2-ylamino]-propyl}-3-thiophen-2-yl-urea
131. 1-(2-Fluoro-phenyl)-3-{3-[4-(2-methyl-benzoyl)-thiazol-2-ylamino]-propyl}-urea
132. 2-Methyl-N-{3-[4-(2-methyl-benzoyl)-thiazol-2-ylamino]-propyl}-benzenesulfonamide
133. 4-Fluoro-N-{3-[4-(2-methyl-benzoyl)-thiazol-2-ylamino]-propyl}-benzenesulfonamide
134. 3-Methoxy-N-{3-[4-(2-methyl-benzoyl)-thiazol-2-ylamino]-propyl}-benzenesulfonamide
135. 4-Methoxy-N-{3-[4-(2-methyl-benzoyl)-thiazol-2-ylamino]-propyl}-benzenesulfonamide
136. N-{3-[4-(2-Methyl-benzoyl)-thiazol-2-ylamino]-propyl}-benzenesulfonamide
137. 2-Chloro-N-{3-[4-(2-methyl-benzoyl)-thiazol-2-ylamino]-propyl}-5-trifluoromethyl-benzenesulfonamide
138. Thiophene-2-sulfonic acid {3-[4-(2-methyl-benzoyl)-thiazol-2-ylamino]-propyl}-amide
139. 3-Fluoro-N-{3-[4-(2-methyl-benzoyl)-thiazol-2-ylamino]-propyl}-benzenesulfonamide
140. 2-Methoxy-5-methyl-N-{3-[4-(2-methyl-benzoyl)-thiazol-2-ylamino]-propyl}-benzenesulfonamide
141. 2,5-Dimethoxy-N-{3-[4-(2-methyl-benzoyl)-thiazol-2-ylamino]-propyl}-benzenesulfonamide
142. 2-Fluoro-N-{5-[5-(pyridine-2-carbonyl)-thiazol-2-ylamino]-pentyl}-benzenesulfonamide
143. 4-Methoxy-N-{5-[5-(pyridine-2-carbonyl)-thiazol-2-ylamino]-pentyl}-benzenesulfonamide
144. Thiophene-2-sulfonic acid {5-[5-(pyridine-2-carbonyl)-thiazol-2-ylamino]-pentyl}-amide
145. 2-Methoxy-5-methyl-N-{5-[5-(pyridine-2-carbonyl)-thiazol-2-ylamino]-pentyl}-benzenesulfonamide
146. 4-Fluoro-N-{5-[5-(pyridine-2-carbonyl)-thiazol-2-ylamino]-pentyl}-benzenesulfonamide
147. 2-Methyl-N-{5-[5-(pyridine-2-carbonyl)-thiazol-2-ylamino]-pentyl}-benzenesulfonamide
148. 3-Fluoro-N-{5-[5-(pyridine-2-carbonyl)-thiazol-2-ylamino]-pentyl}-benzenesulfonamide
149. 2-Chloro-N-{5-[5-(pyridine-2-carbonyl)-thiazol-2-ylamino]-pentyl}-5-trifluoromethyl-benzenesulfonamide
150. N-{5-[5-(Pyridine-2-carbonyl)-thiazol-2-ylamino]-pentyl}-benzenesulfonamide
151. 3-Methoxy-N-{5-[5-(pyridine-2-carbonyl)-thiazol-2-ylamino]-pentyl}-benzenesulfonamide
152. 2-Fluoro-N-{5-[5-(pyridine-4-carbonyl)-thiazol-2-ylamino]-pentyl}-benzenesulfonamide
153. 2-Methoxy-5-methyl-N-{5-[5-(pyridine-4-carbonyl)-thiazol-2-ylamino]-pentyl}-benzenesulfonamide
154. 2-Fluoro-N-{5-[5-(2-methyl-benzoyl)-thiazol-2-ylamino]-pentyl}-benzenesulfonamide
155. 4-Methoxy-N-{5-[5-(2-methyl-benzoyl)-thiazol-2-ylamino]-pentyl}-benzenesulfonamide
156. Thiophene-2-sulfonic acid {5-[5-(2-methyl-benzoyl)-thiazol-2-ylamino]-pentyl}-amide
157. 2-Methoxy-5-methyl-N-{5-[5-(2-methyl-benzoyl)-thiazol-2-ylamino]-pentyl}-benzenesulfonamide
158. 4-Fluoro-N-{5-[5-(2-methyl-benzoyl)-thiazol-2-ylamino]-pentyl}-benzenesulfonamide
159. 2-Methyl-N-{5-[5-(2-methyl-benzoyl)-thiazol-2-ylamino]-pentyl}-benzenesulfonamide
160. 3-Fluoro-N-{5-[5-(2-methyl-benzoyl)-thiazol-2-ylamino]-pentyl}-benzenesulfonamide
161. 2-Chloro-N-{5-[5-(2-methyl-benzoyl)-thiazol-2-ylamino]-pentyl}-5-trifluoromethyl-benzenesulfonamide
162. N-{5-[5-(2-Methyl-benzoyl)-thiazol-2-ylamino]-pentyl}-benzenesulfonamide
163. 3-Methoxy-N-{5-[5-(2-methyl-benzoyl)-thiazol-2-ylamino]-pentyl}-benzenesulfonamide
164. N-{5-[5-(2-Chloro-benzoyl)-thiazol-2-ylamino]-pentyl}-2-fluoro-benzenesulfonamide
165. N-{5-[5-(2-Chloro-benzoyl)-thiazol-2-ylamino]-pentyl}-4-methoxy-benzenesulfonamide
166. Thiophene-2-sulfonic acid {5-[5-(2-chloro-benzoyl)-thiazol-2-ylamino]-pentyl}-amide
167. N-{5-[5-(2-Chloro-benzoyl)-thiazol-2-ylamino]-pentyl}-2-methoxy-5-methyl-benzenesulfonamide
168. N-{5-[5-(2-Chloro-benzoyl)-thiazol-2-ylamino]-pentyl}-4-fluoro-benzenesulfonamide
169. N-{5-[5-(2-Chloro-benzoyl)-thiazol-2-ylamino]-pentyl}-2-methyl-benzenesulfonamide
170. N-{5-[5-(2-Chloro-benzoyl)-thiazol-2-ylamino]-pentyl}-3-fluoro-benzenesulfonamide
171. 2-Chloro-N-{5-[5-(2-chloro-benzoyl)-thiazol-2-ylamino]-pentyl}-5-trifluoromethyl-benzenesulfonamide
172. N-{5-[4-Methyl-5-(2-methyl-benzoyl)-thiazol-2-ylamino]-pentyl}-benzenesulfonamide
173. 2-Methyl-N-{5-[4-methyl-5-(2-methyl-benzoyl)-thiazol-2-ylamino]-pentyl}-benzenesulfonamide
174. 2-Fluoro-N-{5-[4-methyl-5-(2-methyl-benzoyl)-thiazol-2-ylamino]-pentyl}-benzenesulfonamide
175. 3-Fluoro-N-{5-[4-methyl-5-(2-methyl-benzoyl)-thiazol-2-ylamino]-pentyl}-benzenesulfonamide
176. 4-Fluoro-N-{5-[4-methyl-5-(2-methyl-benzoyl)-thiazol-2-ylamino]-pentyl}-benzenesulfonamide
177. 2-Methoxy-5-methyl-N-{5-[4-methyl-5-(2-methyl-benzoyl)-thiazol-2-ylamino]-pentyl}-benzenesulfonamide
178. 3-Methoxy-N-{5-[4-methyl-5-(2-methyl-benzoyl)-thiazol-2-ylamino]-pentyl}-benzenesulfonamide
179. 4-Methoxy-N-{5-[4-methyl-5-(2-methyl-benzoyl)-thiazol-2-ylamino]-pentyl}-benzenesulfonamide
180. Thiophene-2-sulfonic acid {2-[5-(2-methyl-benzoyl)-thiazol-2-ylamino]-ethyl}-amide
181. 2,5-Dimethoxy-N-{3-[5-(2-methyl-benzoyl)-thiazol-2-ylamino]-propyl}-benzenesulfonamide
182. Thiophene-3-sulfonic acid {4-[5-(2-methyl-benzoyl)-thiazol-2-ylamino]-butyl}-amide
183. 2,5-Dimethoxy-N-{5-[5-(2-methyl-benzoyl)-thiazol-2-ylamino]-pentyl}-benzenesulfonamide
184. Thiophene-3-sulfonic acid {2-[5-(2-methyl-benzoyl)-thiazol-2-ylamino]-ethyl}-amide
185. 2,5-Dimethyl-N-{3-[5-(2-methyl-benzoyl)-thiazol-2-ylamino]-propyl}-benzenesulfonamide
186. 5-Chloro-2-methoxy-N-{3-[5-(2-methyl-benzoyl)-thiazol-2-ylamino]-propyl}-benzenesulfonamide
187. 2-Methyl-N-{4-[5-(2-methyl-benzoyl)-thiazol-2-ylamino]-butyl}-benzenesulfonamide
188. 5-Fluoro-2-methyl-N-{4-[5-(2-methyl-benzoyl)-thiazol-2-ylamino]-butyl}-benzenesulfonamide
189. 2-Chloro-N-{4-[5-(2-methyl-benzoyl)-thiazol-2-ylamino]-butyl}-5-trifluoromethyl-benzenesulfonamide
190. 2,5-Dimethyl-N-{5-[5-(2-methyl-benzoyl)-thiazol-2-ylamino]-pentyl}-benzenesulfonamide 191. N-{3-[5-(2-Methyl-benzoyl)-thiazol-2-ylamino]-propyl}-4-trifluoromethoxy-benzenesulfonamide
192. 4-Fluoro-N-{4-[5-(2-methyl-benzoyl)-thiazol-2-ylamino]-butyl}-benzenesulfonamide
193. 2,4-Difluoro-N-{4-[5-(2-methyl-benzoyl)-thiazol-2-ylamino]-butyl}-benzenesulfonamide
194. N-{5-[5-(2-Methyl-benzoyl)-thiazol-2-ylamino]-pentyl}-4-trifluoromethoxy-benzenesulfonamide
195. 2-Chloro-N-{3-[5-(2-methyl-benzoyl)-thiazol-2-ylamino]-propyl}-4-trifluoromethyl-benzenesulfonamide
196. 2-Fluoro-N-{4-[5-(2-methyl-benzoyl)-thiazol-2-ylamino]-butyl}-benzenesulfonamide
197. 5-Chloro-thiophene-2-sulfonic acid {4-[5-(2-methyl-benzoyl)-thiazol-2-ylamino]-butyl}-amide
198. 2-Chloro-N-{5-[5-(2-methyl-benzoyl)-thiazol-2-ylamino]-pentyl}-4-trifluoromethyl-benzenesulfonamide
199. Thiophene-3-sulfonic acid {3-[5-(2-methyl-benzoyl)-thiazol-2-ylamino]-propyl}-amide
200. 5-Fluoro-2-methyl-N-{3-[5-(2-methyl-benzoyl)-thiazol-2-ylamino]-propyl}-benzenesulfonamide
201. 3-Fluoro-N-{4-[5-(2-methyl-benzoyl)-thiazol-2-ylamino]-butyl}-benzenesulfonamide
202. 2-Methoxy-5-methyl-N-{4-[5-(2-methyl-benzoyl)-thiazol-2-ylamino]-butyl}-benzenesulfonamide
203. Thiophene-3-sulfonic acid {5-[5-(2-methyl-benzoyl)-thiazol-2-ylamino]-pentyl}-amide
204. 5-Fluoro-2-methyl-N-{5-[5-(2-methyl-benzoyl)-thiazol-2-ylamino]-pentyl}-benzenesulfonamide
205. 5-Chloro-2-methoxy-N-{2-[5-(2-methyl-benzoyl)-thiazol-2-ylamino]-ethyl}-benzenesulfonamide
206. 2,4-Difluoro-N-{3-[5-(2-methyl-benzoyl)-thiazol-2-ylamino]-propyl}-benzenesulfonamide
207. 2,5-Dimethyl-N-{4-[5-(2-methyl-benzoyl)-thiazol-2-ylamino]-butyl}-benzenesulfonamide
208. 2,5-Dimethoxy-N-{4-[5-(2-methyl-benzoyl)-thiazol-2-ylamino]-butyl}-benzenesulfonamide
209. 2,4-Difluoro-N-{5-[5-(2-methyl-benzoyl)-thiazol-2-ylamino]-pentyl}-benzenesulfonamide
210. 5-Chloro-thiophene-2-sulfonic acid {3-[5-(2-methyl-benzoyl)-thiazol-2-ylamino]-propyl}-amide
211. 4-Methoxy-N-{4-[5-(2-methyl-benzoyl)-thiazol-2-ylamino]-butyl}-benzenesulfonamide
212. 5-Chloro-2-methoxy-N-{4-[5-(2-methyl-benzoyl)-thiazol-2-ylamino]-butyl}-benzenesulfonamide
213. 5-Chloro-thiophene-2-sulfonic acid {5-[5-(2-methyl-benzoyl)-thiazol-2-ylamino]-pentyl}-amide
214. Thiophene-2-sulfonic acid {4-[5-(2-methyl-benzoyl)-thiazol-2-ylamino]-butyl}-amide
215. 3-Methoxy-N-{4-[5-(2-methyl-benzoyl)-thiazol-2-ylamino]-butyl}-benzenesulfonamide
216. N-{4-[5-(2-Methyl-benzoyl)-thiazol-2-ylamino]-butyl}-4-trifluoromethoxy-benzenesulfonamide
217. Thiophene-2-sulfonic acid methyl-{3-[5-(2-methyl-benzoyl)-thiazol-2-ylamino]-propyl}-amide
218. 3-Methoxy-N-methyl-N-{3-[5-(2-methyl-benzoyl)-thiazol-2-ylamino]-propyl}-benzenesulfonamide
219. 2-Chloro-N-methyl-N-{3-[5-(2-methyl-benzoyl)-thiazol-2-ylamino]-propyl}-4-trifluoromethyl-benzenesulfonamide
220. 2,N-Dimethyl-N-{3-[5-(2-methyl-benzoyl)-thiazol-2-ylamino]-propyl}-benzenesulfonamide
221. 5-Fluoro-2,N-dimethyl-N-{3-[5-(2-methyl-benzoyl)-thiazol-2-ylamino]-propyl}-benzenesulfonamide
222. 2-Chloro-N-methyl-N-{3-[5-(2-methyl-benzoyl)-thiazol-2-ylamino]-propyl}-5-trifluoromethyl-benzenesulfonamide
223. 4-Fluoro-N-methyl-N-{3-[5-(2-methyl-benzoyl)-thiazol-2-ylamino]-propyl}-benzenesulfonamide
224. 2,4-Difluoro-N-methyl-N-{3-[5-(2-methyl-benzoyl)-thiazol-2-ylamino]-propyl}-benzenesulfonamide
225. 2-Fluoro-N-methyl-N-{3-[5-(2-methyl-benzoyl)-thiazol-2-ylamino]-propyl}-benzenesulfonamide
226. 5-Chloro-thiophene-2-sulfonic acid methyl-{3-[5-(2-methyl-benzoyl)-thiazol-2-ylamino]-propyl}-amide
227. 3-Fluoro-N-methyl-N-{3-[5-(2-methyl-benzoyl)-thiazol-2-ylamino]-propyl}-benzenesulfonamide
228. 2-Methoxy-5,N-dimethyl-N-{3-[5-(2-methyl-benzoyl)-thiazol-2-ylamino]-propyl}-benzenesulfonamide
229. 4-Chloro-N-methyl-N-{3-[5-(2-methyl-benzoyl)-thiazol-2-ylamino]-propyl}-benzenesulfonamide
230. 2,5,N-Trimethyl-N-{3-[5-(2-methyl-benzoyl)-thiazol-2-ylamino]-propyl}-benzenesulfonamide
231. N-Methyl-N-{3-[5-(2-methyl-benzoyl)-thiazol-2-ylamino]-propyl}-4-nitro-benzenesulfonamide
232. 4-Methoxy-N-methyl-N-{3-[5-(2-methyl-benzoyl)-thiazol-2-ylamino]-propyl}-benzenesulfonamide
233. 5-Chloro-2-methoxy-N-methyl-N-{3-[5-(2-methyl-benzoyl)-thiazol-2-ylamino]-propyl}-benzenesulfonamide Examples of particularly preferred compounds of formula I are:

Thiophene-2-sulfonic acid {3-[5-(2-methyl-benzoyl)-thiazol-2-ylamino]-propyl}-amide;

2-methoxy-5-methyl-N-{3-[5-(2-methyl-benzoyl)-thiazol-2-ylamino]-propyl}-benzenesulfonamide;

2-chloro-N-{3-[5-(2-methyl-benzoyl)-thiazol-2-ylamino]-propyl}-5-trifluoromethyl-benzenesulfonamide;

thiophene-2-sulfonic acid {3-[5-(2-chloro-benzoyl)-thiazol-2-ylamino]-propyl}-amide;

N-{3-[5-(2-chloro-benzoyl)-thiazol-2-ylamino]-propyl}-2-methoxy-5-methyl-benzenesulfonamide;

2-chloro-N-{3-[5-(2-chloro-benzoyl)-thiazol-2-ylamino]-propyl}-5-trifluoromethyl-benzenesulfonamide;

2-chloro-N-{3-[4-(2-methyl-benzoyl)-thiazol-2-ylamino]-propyl}-5-trifluoromethyl-benzenesulfonamide;

2-methoxy-5-methyl-N-{3-[4-(2-methyl-benzoyl)-thiazol-2-ylamino]-propyl}-benzenesulfonamide;

2-methoxy-5-methyl-N-{5-[5-(pyridine-2-carbonyl)-thiazol-2-ylamino]-pentyl}-benzenesulfonamide;

4-methoxy-N-{5-[5-(2-methyl-benzoyl)-thiazol-2-ylamino]-pentyl}-benzenesulfonamide;

2-methoxy-5-methyl-N-{5-[5-(2-methyl-benzoyl)-thiazol-2-ylamino]-pentyl}-benzenesulfonamide;

2-methyl-N-{5-[5-(2-methyl-benzoyl)-thiazol-2-ylamino]-pentyl}-benzenesulfonamide;

3-fluoro-N-{5-[5-(2-methyl-benzoyl)-thiazol-2-ylamino]-pentyl}-benzenesulfonamide;

2-chloro-N-{5-[5-(2-methyl-benzoyl)-thiazol-2-ylamino]-pentyl}-5-trifluoromethyl-benzenesulfonamide;

N-{5-[5-(2-chloro-benzoyl)-thiazol-2-ylamino]-pentyl}-2-fluoro-benzenesulfonamide;

N-{5-[5-(2-chloro-benzoyl)-thiazol-2-ylamino]-pentyl}-2-methoxy-5-methyl-benzenesulfonamide;

N-{5-[5-(2-chloro-benzoyl)-thiazol-2-ylamino]-pentyl}-2-methyl-benzenesulfonamide;

2-methoxy-5-methyl-N-{5-[4-methyl-5-(2-methyl-benzoyl)-thiazol-2-ylamino]-pentyl}-benzenesulfonamide;

2-chloro-N-{3-[5-(2-methyl-benzoyl)-thiazol-2-ylamino]-propyl}-4-trifluoromethyl-benzenesulfonamide;

5-fluoro-2-methyl-N-{3-[5-(2-methyl-benzoyl)-thiazol-2-ylamino]-propyl}-benzenesulfonamide;

2,5-dimethoxy-N-{4-[5-(2-methyl-benzoyl)-thiazol-2-ylamino]-butyl}-benzenesulfonamide;

5-chloro-thiophene-2-sulfonic acid {3-[5-(2-methyl-benzoyl)-thiazol-2-ylamino]-propyl}-amide;

thiophene-2-sulfonic acid {4-[5-(2-methyl-benzoyl)-thiazol-2-ylamino]-butyl}-amide;

thiophene-2-sulfonic acid methyl-{3-[5-(2-methyl-benzoyl)-thiazol-2-ylamino]-propyl}-amide;

2,N-dimethyl-N-{3-[5-(2-methyl-benzoyl)-thiazol-2-ylamino]-propyl}-benzenesulfonamide;

5-chloro-thiophene-2-sulfonic acid methyl-{3-[5-(2-methyl-benzoyl)-thiazol-2-ylamino]-propyl}-amide;

4-chloro-N-methyl-N-{3-[5-(2-methyl-benzoyl)-thiazol-2-ylamino]-propyl}-benzenesulfonamide and N-methyl-N-{3-[5-(2-methyl-benzoyl)-thiazol-2-ylamino]-propyl}-4-nitro-benzenesulfonamide.

Examples of particularly preferred compounds of formula I are:

Thiophene-2-sulfonic acid {3-[5-(2-methyl-benzoyl)-thiazol-2-ylamino]-propyl}-amide;

2-methoxy-5-methyl-N-{3-[5-(2-methyl-benzoyl)-thiazol-2-ylamino]-propyl}-benzenesulfonamide;

2-chloro-N-{3-[5-(2-methyl-benzoyl)-thiazol-2-ylamino]-propyl}-5-trifluoromethyl-benzenesulfonamide;

thiophene-2-sulfonic acid {3-[5-(2-chloro-benzoyl)-thiazol-2-ylamino]-propyl}-amide;

N-{3-[5-(2-chloro-benzoyl)-thiazol-2-ylamino]-propyl}-2-methoxy-5-methyl-benzenesulfonamide;

2-chloro-N-{3-[5-(2-chloro-benzoyl)-thiazol-2-ylamino]-propyl}-5-trifluoromethyl-benzenesulfonamide;

2-chloro-N-{3-[4-(2-methyl-benzoyl)-thiazol-2-ylamino]-propyl}-5-trifluoromethyl-benzenesulfonamide;

2-methoxy-5-methyl-N-{3-[4-(2-methyl-benzoyl)-thiazol-2-ylamino]-propyl}-benzenesulfonamide;

2-methoxy-5-methyl-N-{5-[5-(pyridine-2-carbonyl)-thiazol-2-ylamino]-pentyl}-benzenesulfonamide;

4-methoxy-N-{5-[5-(2-methyl-benzoyl)-thiazol-2-ylamino]-pentyl}-benzenesulfonamide;

2-methoxy-5-methyl-N-{5-[5-(2-methyl-benzoyl)-thiazol-2-ylamino]-pentyl}-benzenesulfonamide;

2-methyl-N-{5-[5-(2-methyl-benzoyl)-thiazol-2-ylamino]-pentyl}-benzenesulfonamide;

3-fluoro-N-{5-[5-(2-methyl-benzoyl)-thiazol-2-ylamino]-pentyl}-benzenesulfonamide;

2-chloro-N-{5-[5-(2-methyl-benzoyl)-thiazol-2-ylamino]-pentyl}-5-trifluoromethyl-benzenesulfonamide;

N-{5-[5-(2-chloro-benzoyl)-thiazol-2-ylamino]-pentyl}-2-fluoro-benzenesulfonamide;

N-{5-[5-(2-chloro-benzoyl)-thiazol-2-ylamino]-pentyl}-2-methoxy-5-methyl-benzenesulfonamide;

N-{5-[5-(2-chloro-benzoyl)-thiazol-2-ylamino]-pentyl}-2-methyl-benzenesulfonamide; and 2-methoxy-5-methyl-N-{5-[4-methyl-5-(2-methyl-benzoyl)-thiazol-2-ylamino]-pentyl}benzenesulfonamide.

Processes for the manufacture of compounds of formula I are an object of the invention.

The preparation of compounds of formula I of the present invention may be carried out in sequential or convergent synthetic routes. Syntheses of the invention are shown in the following Schemes. The skills required for carrying out the reaction and purification of the resulting products are known to those in the art. The substituents and indices used in the following description of the processes have the significance given above unless indicated to the contrary.

Compounds of general formula IH ($R^2$ means hydrogen) can be prepared according to scheme 1 as follows:

a) Bis amino derivatives IA, either commercially available or prepared from commercially available precursors by methods taught in the art, are mono-protected with a suitable protecting group (PG i.e. Boc, Fmoc, and the like), provided that PG has no adverse effect on the reaction or on the reagents involved in the synthetic route, by reaction of IA with preferably $Boc_2O$, preferably in the presence or the absence of a base such as triethylamine, diisopropylethylamine, and the like, preferably in the presence of a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice. (literature: J. Med. Chem., 32(2), 391–6; 1989).

b) Thioureas can be prepared from suitable starting materials according to methods known in the art. The elaboration of the thiourea-moiety in ID starting from an amino functionality, like in IB can be affected by methods described in literature. For example mono-protected derivatives IB are condensed with benzoyl isothiocyanate in a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the protected urea derivatives IC. (literature: Organic Letters, 2(20), 3237–3240;2000). The urea derivatives IC are subjected to basic cleavage conditions such as $K_2CO_3$ aq., and the like, in a solvent such as methanol, and the like, to liberate the urea functionality and access ureas ID. (for reaction conditions described in literature affecting such a reaction see for example: J. Med. Chem., 32(8), 1963–70; 1989).

c) The conversion of the liberated ureas ID to Dimethylaminomethylene-thioureido derivatives IE (R2 means hydrogen) was affected by reaction of derivatives ID with N,N-Dimethylformamide dimethyl acetal either neat or in a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, DMF and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the protected urea derivatives IC. For reaction conditions described in literature affecting such a reaction see for example: Heterocycles, 11, 313–18; 1978.

d) Dimethylaminomethylene-thioureido derivatives IE can be converted to thiazole derivatives IF (R2 means hydrogen) by reaction of IE with α-bromoketones (a known compound or compound prepared by known methods. The source for α-Bromoketones employed is indicated as appropriate) in a solvent such as ethanol, and the like, in the presence or the absence of a base. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, methanol, ethanol and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the protected thiazole derivatives IF. For reaction conditions described in literature affecting such a reaction see for example: J. Heterocycl. Chem., 16(7), 1377–83; 1979. The resulting compound of formula IF is a compound of the present invention and may be the desired product; alternatively it may be subjected to consecutive reactions.

e) Cleavage of the protecting group PG such as Boc, Fmoc, and the like from thiazole derivatives IF to access free amines IG or various salts thereof, IF is in the case PG means Boc subjected to suitable reaction conditions like acidic cleavage. There is no particular restriction on the nature of the acid used in this stage, and any acid commonly used in this type of reaction may equally be employed here. Examples of such acids include: HCl, TFA, and the like in a solvent. There is no particular restriction on the nature of the solvent to be employed, provided that it has no adverse effect on the reaction or the reagents involved and that it can dissolve the reagents, at least to some extent. Examples for suitable solvents include: dioxane, water, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IG. For conditions described in literature affecting the cleavage of a protecting group see for example: Protecting Groups, Kocienski, P. Thieme Verlag New York 1994.

f) Sulfonamides, amides, carbamates and ureas can be prepared from suitable starting materials according to methods known in the art. The conversion of the amino-moiety in IG to access sulfonamides, amides, carbamates and can be affected by methods described in literature. For example the conversion of the amine derivatives IG or their respective salts to access compounds of the general formula IH is affected by reaction of IG with suitable acid chlorides, sulfonyl chlorides, isocyanates, chloroformates, or carbonate esters (compounds known or compound prepared by known methods) respectively in a solvent like dichloromethane and in the presence or the absence of a base. There is no particular restriction on the nature of the solvent to be employed, provided that it has no adverse effect on the reaction or the reagents involved and that it can dissolve the reagents, at least to some extent. Examples for suitable solvents include: chloroform, or dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IH. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999.

Scheme 1

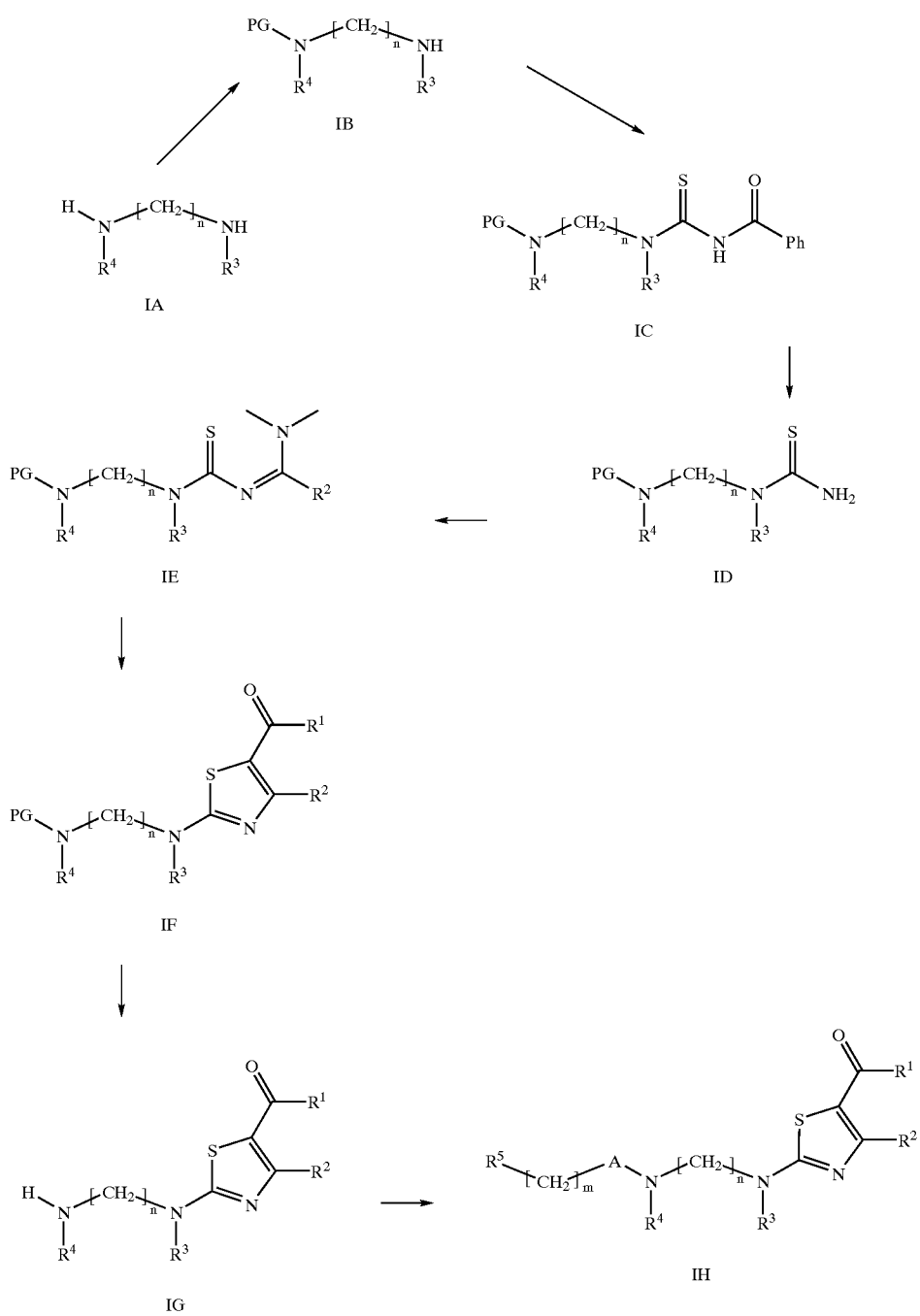

Compounds of general formula IIE ($R^2$ means alkyl or cycloalkyl) can be prepared according to scheme 2 as follows:

a) Thioisocyanates can be prepared from suitable starting materials according to methods known in the art. The elaboration of the thioisocyanate-moiety in IIA ($R^3$ means hydrogen) starting from an amino functionality, can be affected by methods described in literature. For example compounds of the general formula IB (PG for example Boc, Fmoc, and such like) are condensed with carbondisulfide, neat or in a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, THF and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield an intermediate which is reacted with cyanamide in one-pot or after isolation of the intermediate. Elaboration of the thioisocanate derivatives IIA (R3 means hydrogen) is affected by addition of a base such as pyridine, or the like. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, THF and the like. There is no particular restriction on the nature of the base used in this stage, and any base commonly used in this type of reaction may equally be employed here. Examples of such bases include pyridine, triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thioisocyanate derivatives IIA. For reaction conditions described in literature affecting such a reaction see for example: Journal of Organic Chemistry, 65(19), 6069–6072; 2000.

b) Thioureido derivatives can be prepared from suitable starting materials according to methods known in the art. The elaboration of the thioisocyanate-moiety in IIA (R3 means hydrogen) to a thioureido-moiety can be affected by methods described in literature. For example compounds of the general formula IIA are condensed with an amidine or their salts (R2 means alkyl, cycloakly), a known compound or compound prepared by known methods, in a solvent such as THF, or the like, and a base,:such as NaOH, or the like. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, THF and the like. There is no particular restriction on the nature of the base used in this stage, and any base commonly used in this type of reaction may equally be employed here. Examples of such bases include NaOHaq., KOHaq, NEt$_3$, and the like. The reaction can take place over a wide range of temperatures, and the precise reaction temperature is not critical to the invention. We find it convenient to carry out the reaction from 0° C. to heating to reflux temperature of the solvent. The time required for the reaction may also vary widely, depending on many factors, notably the reaction temperature and the nature of the reagents. However, a period of from 0.5 h to several days will usually suffice to yield the thioureido derivatives IIB. For reaction conditions described in literature affecting such a reaction see for example: C. R. Seances Acad. Sci., Ser. 2, 294(19), 1183–6; 1982.

c) Dimethylaminomethylene-thioureido derivatives IIB can be converted to thiazole derivatives IIC (R2 means alkyl, cycloalkyl) by reaction of IIB with α-bromoketones (a known compound or compound prepared by known methods) in a solvent such as ethanol, and the like, in the presence or the absence of a base. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, DMF, dioxane, methanol, ethanol and the like. There is no particular restriction on the nature of the base used in this stage, and any base commonly used in this type.of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the protected thiazole derivatives IIC (R3 means H). For reaction conditions described in literature affecting such a reaction see for example: Org. Chem., 65(21), 7244–7247; 2000. The resulting compound of formula IIC (R3 means H) is a compound of the present invention and may be the desired product; alternatively it may be subjected to consecutive reactions. Introduction of R3 means alkyl or cycloalkyl can be affected by reductive amination of IIC with the respective aldehyde under reducing conditions in a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, THF, and the like. There is no particular restriction on the nature of the reducing agent used in this stage, and any reducing agent commonly used in this type of reaction may equally be employed here. Examples of such reducing agents include NaBH$_4$, NaCNBH$_3$, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the protected thiazole derivatives IIC (R3 means alkyl or cycloalkyl). For reaction conditions described in literature affecting a reductive amination see for example: Reductive amination in: A Guide to Functional Group Preparations, 2nd Edition, Richard C. Larock. John Wiley & Sons, New York, N.Y. 1999. The resulting compound of formula IIC (R3 means alkyl or cycloalkyl) is a compound of the present invention and may be the desired product; alternatively it may be subjected to consecutive reactions.

d) Cleavage of the protecting group such as Boc and Fmoc, and the like from thiazole derivatives IIC to access free amines IID or various salts thereof, IIC is subjected to suitable reaction conditions like for example acidic cleavage for the cleavage of the Boc-protecting group. There is no particular restriction on the nature of the acid used in this stage, and any acid commonly used in this type of reaction may equally be employed here. Examples of such acids include: HCl, TFA, and the like in a solvent. There is no particular restriction on the nature of the solvent to be employed, provided that it has no adverse effect on the reaction or the reagents involved and that it can dissolve the reagents, at least to some extent. Examples for suitable solvents include: dioxane, water, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IID. For conditions described in literature affecting the cleavage of a protecting group see for example: Protecting Groups, Kocienski, P. Thieme Verlag New York 1994.

e) Sulfonamides, amides, carbamates and ureas can be prepared from suitable starting materials according to methods known in the art. The conversion of the amino-moiety in IID to access sulfonamides, amides, carbamates and ureas can be affected by methods described in literature. For example the conversion of the amine derivatives IID or their respective salts to access compounds of the general formula IIE is affected by reaction of IID with suitable acid chlorides, sulfonyl chlorides, isocyanates, chloroformates, or carbonate esters (compounds known or compound prepared by known methods) respectively in a solvent like dichloromethane and in the presence or the absence of a base. There is no particular restriction on the nature of the solvent to be employed, provided that it has no adverse effect on the reaction or the reagents involved and that it can dissolve the reagents, at least to some extent. Examples for suitable solvents include: chloroform, dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IIE. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999.

Scheme 2

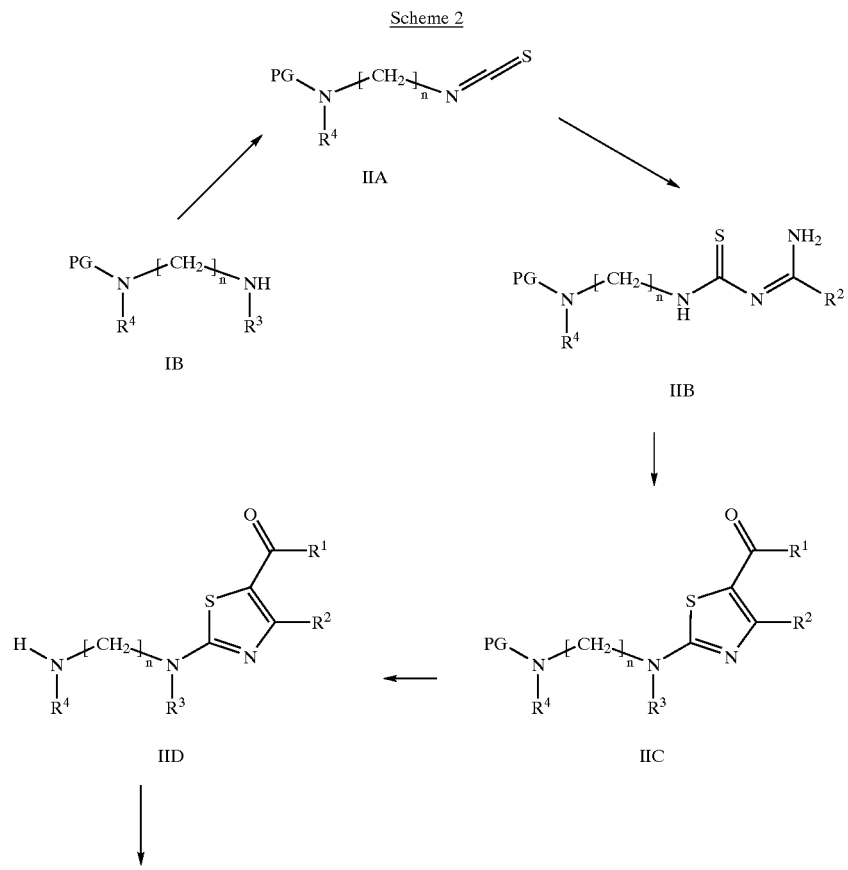

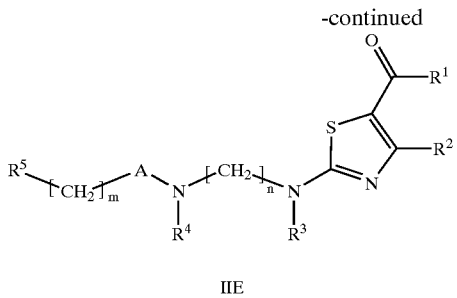

IIE

Compounds of general formula IIID can be prepared according to scheme 3 as follows:
a) Aminothiazoles can be prepared from suitable starting materials according to methods known in the art. The conversion of a thiourea-moiety like in derivatives of the general formula ID can be affected by methods described in literature. For example thiourea derivatives of the general formula ID are reacted with a-bromo-diketones of the general formula IIIA (compounds known or compounds prepared by known methods) in a solvent such as methanol, or the like, in the presence or the absence of a base, such as triethylamine, or the like. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, ethanol, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IIIB. For reaction conditions described in literature affecting such reactions see for example: J. Heterocycl. Chem., 16(7), 1377–83; 1979.
b) Cleavage of the protecting group such as Boc and Fmoc, and the like from thiazole derivatives IIIB to access free amines IIIC or various salts thereof, IIIB is subjected to suitable reaction conditions like for example acidic cleavage for the cleavage of the Boc-protecting group. There is no particular restriction on the nature of the acid used in this stage, and any acid commonly used in this type of reaction may equally be employed here. Examples of such acids include: HCl, TFA, and the like in a solvent. There is no particular restriction on the nature of the solvent to be employed, provided that it has no adverse effect on the reaction or the reagents involved and that it can dissolve the reagents, at least to some extent. Examples for suitable solvents include: dioxane, water, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IIIC. For conditions described in literature affecting the cleavage of a protecting group see for example: Protecting Groups, Kocienski, P. Thieme Verlag New York 1994.
c) Sulfonamides, amides, carbamates and ureas can be prepared from suitable starting materials according to methods known in the art. The conversion of the amino-moiety in IIIC to access sulfonamides, amides, carbamates and ureas can be affected by methods described in literature. For example the conversion of the amine derivatives IIIC or their respective salts to access compounds of the general formula IIID is affected by reaction of IIIC with suitable acid chlorides, sulfonyl chlorides, isocyanates, chloroformates, or carbonate esters (compounds known or compound prepared by known methods) respectively in a solvent, such as dioxane and methanol, and such like, and in the presence or the absence of a base, such as triethylamine, or the like. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thiazole derivatives IIID. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999.

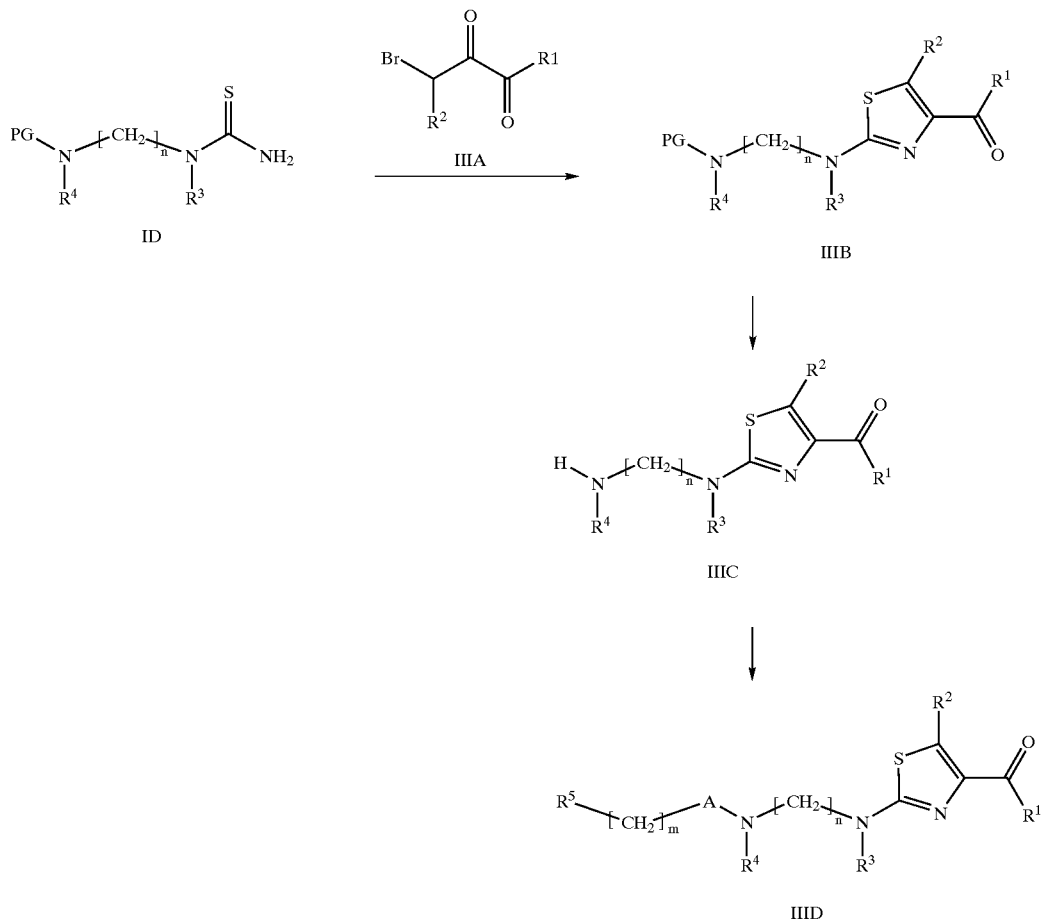

Scheme 3

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid.

The conversion of compounds of formula I into pharmaceutically usable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicyclohexylcarbodiimide (DCC) to produce the carboxylic ester or carboxylic amide.

Preferred intermediates are:

Example H
 [2-(3-Amino-propylamino)-thiazol-5-yl]-phenyl-methanone; hydrochloride Example I
 [2-(3-Amino-propylamino)-thiazol-5-yl]-o-tolyl-methanone; hydrochloride Example J
 [2-(3-Amino-propylamino)-thiazol-5-yl]-(2-ethyl-phenyl)-methanone; hydrochloride Example K
 [2-(3-Amino-propylamino)-thiazol-5-yl]-(2-fluoro-phenyl)-methanone; hydrochloride Example L
 [2-(3-Amino-propylamino)-thiazol-5-yl]-(2-chloro-phenyl)-methanone; hydrochloride Example M
 [2-(3-Amino-propylamino)-thiazol-5-yl]-(2-trifluoromethyl-phenyl)-methanone; hydrochloride Example N
 [2-(3-Amino-propylamino)-thiazol-5-yl]-(4-methyl-pyridin-3-yl)-methanone; hydrochloride Example O
 2-(3-Amino-propylamino)-thiazol-5-yl]-(3-methyl-pyridin-2-yl)-methanone; hydrochloride Example P
 [2-(3-Amino-propylamino)-thiazol-5-yl]-(2-methyl-pyridin-3-yl)-methanone; hydrochloride Example Q
 [2-(3-Amino-propylamino)-thiazol-5-yl]-(3-methyl-pyrazin-2-yl)-methanone; hydrochloride Example R
 [2-(3-Amino-propylamino)-thiazol-5-yl]-(3-methyl-thiophen-2-yl)-methanone; hydrochloride Example S
 [2-(5-Amino-pentylamino)-thiazol-5-yl]-o-tolyl-methanone; hydrochloride Example T
  [2-(5-Amino-pentylamino)-thiazol-5-yl]-pyridin-2-yl-methanone; hydrochloride
Example U
  [2-(5-Amino-pentylamino)-thiazol-5-yl]-pyridin-4-yl-methanone; hydrochloride
Example V
  [2-(5-Amino-pentylamino)-thiazol-5-yl]-(2-chloro-phenyl)-methanone; hydrochloride
Example Y
  {3-[4-(2-Methyl-benzoyl)-thiazol-2-ylamino]-propyl}-carbamic acid tert-butyl ester
Example Z
  [2-(3-Amino-propylamino)-thiazol-4-yl]-o-tolyl-methanone; hydrochloride
Example AC
  {5-[4-Methyl-5-(2-methyl-benzoyl)-thiazol-2-ylamino]-pentyl}-carbamic acid tert-butyl ester
Example AD
  [2-(5-Amino-pentylamino)-4-methyl-thiazol-5-yl]-o-tolyl-methanone hydrochloride Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions containing a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A preferred object of the invention is the use of compounds as described before for the production of medicaments for the treatment of obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

Particularly preferred is a method for the treatment of obesity whereby an effective amount of a compound as mentioned above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

A preferred process for the preparation of a compound of formula I comprises the reaction of a compound of formula (II)

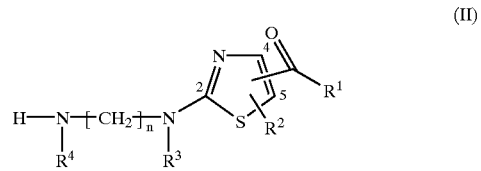

in the presence of a compound of formula (III)

wherein $R^1$ to $R^5$, A, m and n are defined as before and, wherein X means e.g. chloro or bromo.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention is a pharmaceutical composition comprising a compound of formula I described above and a therapeutically inert carrier. Preferred is this composition comprising further a therapeutically effective amount of a lipase inhibitor. Particularly preferred is the above composition, wherein the lipase inhibitor is orlistat.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Assay Procedures
Cloning of Mouse NPY5 Receptor cDNAs:
  The full-length cDNA encoding the mouse NPY5 (mNPY5) receptor was amplified from mouse brain cDNA using specific primers, designed based on the published sequence, and Pfu DNA-Polymerase. The amplification product was subcloned into the mammalian expression vector pcDNA3 using EcoRI and XhoI restriction sites. Positive clones were sequenced and one clone, encoding the published sequence (see Borowsky, B., et al., Molecular biology and pharmacology of multiple NPY Y5 receptor species homologs, Regul. Pept. (1998) 75–76:45–53) was selected for generation of stable cell clones.

Stable Transfection:

Human embryonic kidney 293 (HEK293) cells were transfected with 10 μg mNPY5 DNA using the lipofectamine reagent (Gibco BRL) according to the manufacturer's instruction. Two days after transfection, geneticin selection (1 mg/ml) was initiated and several stable clones were isolated. One clone was further used for pharmacological characterization.

Radioligand Competition Binding:

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-phenanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labelled peptide YY (PYY) and 10 μL DMSO containing increasing amounts of unlabeled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I]labelled neuropeptide Y. It is determined by linear regression analysis after logit/log transformation of the binding data.

Results obtained in the foregoing test using representative compounds of the invention as the test compounds are shown in the following table:

| Compound | $IC_{50}$ |
|---|---|
| Example No.1<br>2-Fluoro-N-{3-[5-(pyridine-2-carbonyl)-thiazol-2-ylamino]-propyl}-benzenesulfonamide | 5.4 nM |
| Example No. 140<br>2-Methoxy-5-methyl-N-{3-[4-(2-methyl-benzoyl)-thiazol-2-ylamino]-propyl}-benzene sulfonamide | 6 nM |

Compounds as described above have $IC_{50}$ values below 1000 nM; more preferred compounds have $IC_{50}$ values below 100 nM. Most preferred compounds have $IC_{50}$ values below 10 nM. These results have been obtained by using the foregoing test.

The in vitro assay published by D. Lachammer, et al., Reversal of NPY inhibition of forkelin-stimulated cAMP production, J. Biol. Chem. (1992) 267:10935–8, and M. H. Norman et al., J. Med. Chem. (2001) 44:2344–56, was used to confirm that the compounds of the present invention are antagonists of neuropeptide Y.

The compounds of formula I and their pharmaceutically usable salts, solvates and esters can be used as medicaments (e.g. in the form of pharmaceutical preparations which include pharmaceutically acceptable carriers which are therapeutically inert). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically usable salts, solvates and esters can be processed with pharmaceutically inert, inorganic or organic adjuvants for the production of tablets, coated tablets, dragees and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts, solvates and esters can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by the examples, which have no limiting character.

EXAMPLES

Example A (3-Thioureido-propyl)-carbamic Acid tert-Butyl Ester

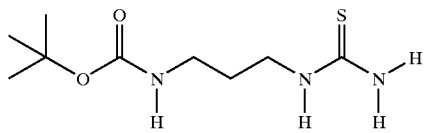

A solution of 2 g (11.47 mmol) (3-Amino-propyl)-carbamic acid tert-butyl ester in 20 ml THF was treated with 1.62 ml (11.47 mmol) Benzoyl isothiocyanate and stirred for 1 h at room temperature. After removal of the volatiles the residue was suspended in 50 ml methanol and 4.8 g (34.4 mmol) $K_2CO_3$ in 50 ml water was added. The mixture was stirred at room temperature for 16 h, concentrated, and extracted with ethyl acetate. The combined organic layers were washed with $NaHCO_3$ sat., brine, dried with $MgSO_4$ and evaporated under reduced pressure. The residue was purified by flash column chromatography on silica eluting with ethyl acetate/heptane. The combined product fractions were evaporated under reduced pressure to yield 1.48 g (74%) of the title compound.

1-H-NMR (300 MHz, DMSO-d6) δ=7.57 (s, br, 2H, $NH_2$), 6.93 (s, br, 1H, NH), 6.80 (s, br, 1H, NH), 3.33 (m, 2H, $CH_2$), 2.93 (m, 2H, $CH_2$), 1.54 (m, 2H, $CH_2$), 1.37 (s, 9H, $CH_3$). MS (m/e): 234.3 ($MH^+$, 100%).

Example B (5-Thioureido-pentyl)-carbamic Acid tert-Butyl Ester

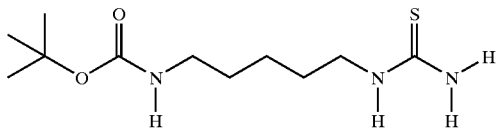

The title compound was synthesised from (5-Amino-pentyl)-carbamic acid tert-butyl ester according to the procedure described for Example A MS (m/e): 262.4 ($MH^+$, 100%).

Example C

[3-(3-Dimethylaminomethylene-thioureido)-propyl]-carbamic Acid tert-Butyl Ester

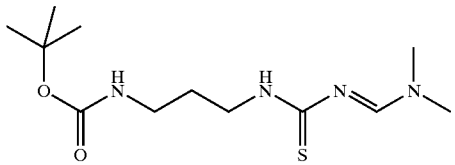

A mixture of 1.48 g (6.35 mmol) (3-Thioureido-propyl)-carbamic acid tert-butyl ester and 15 ml Dimethylformamide dimethyl acetal was heated to 100° C. for 16 h. The mixture was concentrated and the residue was purified by flash column chromatography on silica eluting with ethyl acetate/n-hexane 1/1 to yield 1.65 g (90%) of the title compound.

1-H-NMR (300 MHz, DMSO-d6) δ=8.68 (s, 1H, CH), 8.63 (s, br, 1H, NH), 6.77 (s, br, 1H, NH), 3.44 (m, 2H, $CH_2$), 3.11 (s, 3H, $CH_3$), 2.97 (s, 3H, $CH_3$), 2.87 (m, 1.57 (t, J=5.1 Hz, 2H, $CH_2$), 1.37 (s, 9H, $CH_3$). MS (m/e): 289.3 ($MH^+$, 100%).

Example D

[5-(3-Dimethylaminomethylene-thioureido)-pentyl]-carbamic Acid tert-Butyl Ester

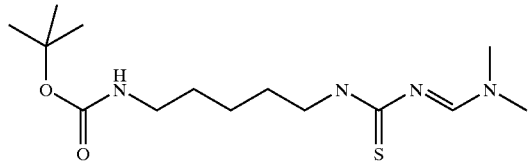

The title compound was synthesized from (5-Thioureido-pentyl)-carbamic acid tert-butyl ester and Dimethylformamide dimethyl acetal according to the procedure described for Example C in 54% yield.

1-H-NMR (300 MHz, DMSO-d6) δ=8.68 (s, 1H, CH), 8.66 (s, br, 1H, NH), 6.75 (s, br, 1H, NH), 3.45 (m, 2H, $CH_2$), 3.11 (s, 3H, $CH_3$), 2.97 (s, 3H, $CH_3$), 2.90 (m, 2H, $CH_2$), 1.50 (m, 2H, $CH_2$), 1.20 (m, 2H, $CH_2$), 1.36 (s, 9H, $CH_3$). MS (m/e): 317.4 ($MH^+$, 100%).

Example E

2-Bromo-1-(3-methyl-pyrazin-2-yl)-ethanone Dihydrobromide

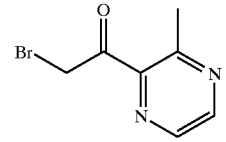

A solution of 5.4 g (40 mmol) 1-Pyrazin-2yl-ethanone in 21 ml HBr (33%) and 7 ml methanol was treated with 2.05 ml (40 mmol) bromine and heated to 60° C. for 7 h. The precipitate was filtered off, washed with ethyl acetate/diethyl ether 1/1 and dried to obtain 8.3 g (55%) of the title compound as grey solid.

1-H-NMR (400 MHz, DMSO-d6) δ=8.78 (d, J=2 Hz, 1H, H-5), 8.66 ((d, J=2 Hz, 1H, H-6), 5.01 (s, 2H, $CH_2$), 2.75 (s, 3H, $CH_3$). MS (m/e): 215.0 (M+H, 100%).

Example F

2-Bromo-1-(4-methyl-pyridin-3-yl)-ethanone Hydrobromide

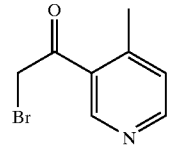

The title compound was synthesised according to Example E 1-(4-methyl-pyridin-3-yl)-ethanone and HBr/bromine in 85% yield as grey solid. MS (m/e): 214.0 (M+H, 100%).

Example G

2-Bromo-1-(2-ethyl-phenyl)-ethanone

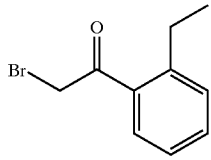

To a solution of 15.2 g (88 mmol) dibromethane in 120 ml THF at −75° C. was added 44 ml (88 mmol) of a 2M solution of LDA in THF and subsequently 6.57 g (40 mmol) ethylbenzoic acid methyl ester in 80 ml THF. 37.5 ml of a 1.6 M n-butyl lithium solution in n-hexane was added and after 30 min the mixture was treated carefully below −65° C. with 35 ml HCl (37%). The mixture was washed with water and $NaHCO_3$ aq. and the organic phase was dried with $MgSO_4$, filtered and concentrated under reduced pressure. The residue was purified by flash column chromatography on silica eluting with ethyl acetate/hexane 1:9 twice to afford 3.8 g (41%) of the title compound as yellow oil. MS (m/e): 227.1 (M+H, 100%).

Example 25

{3-[5-(2-Methyl-benzoyl)-thiazol-2-ylamino]-propyl}-carbamic Acid tert-Butyl Ester

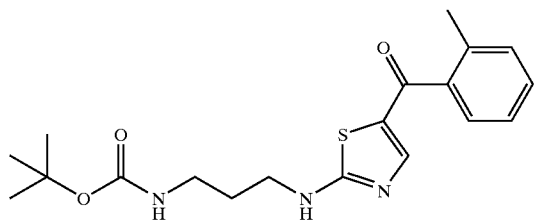

A mixture of 613 mg (2.9 mmol) 2-methyl phenacylbromide (literature: WO9907666), 691 mg (2.4 mmol) [3-(3-Dimethylaminomethylene-thioureido)-propyl]-carbamic acid tert-butyl ester and 1 ml (7.2 mmol) $NEt_3$ in 20 ml ethanol was heated to 100° C. for 16 h. The mixture was concentrated and purified by flash column chromatography on silica eluting with ethyl acetate/n-hexane 1/1. The combined product fractions were evaporated and 693 mg (77%) of the title compound (MS (m/e): 375.9 (MH$^+$, 100%)) were obtained.

Example 26

{3-[5-(2-Chloro-benzoyl)-thiazol-2-ylamino]-propyl}-carbamic Acid tert-Butyl Ester

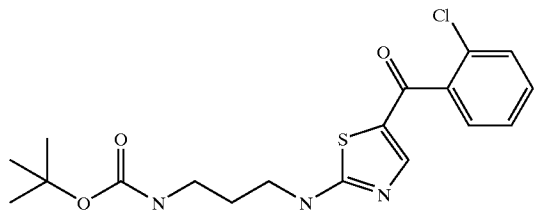

The title compound was synthesised from [3-(3-Dimethylaminomethylene-thioureido)-propyl]-carbamic acid tert-butyl ester and 2-chloro phenacylbromide (commercially available) according to the procedure described for Example 25. MS (m/e): 395.8 (MH$^+$, 100%).

Example 27

{3-[5-(2-Ethyl-benzoyl)-thiazol-2-ylamino]-propyl}-carbamic Acid tert-Butyl Ester

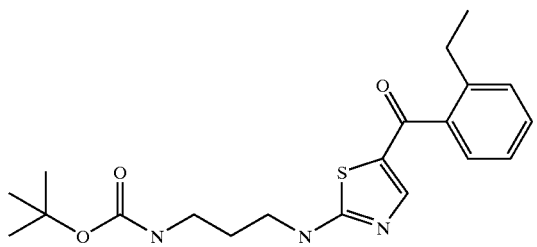

The title compound was synthesised from [3-(3-Dimethylaminomethylene-thioureido)-propyl]-carbamic acid tert-butyl ester and 2-ethyl phenacylbromide according to the procedure described for Example 25. MS (m/e): 389.9 (MH$^+$, 100%).

Example 28

{3-[5-(2-Trifluoromethyl-benzoyl)-thiazol-2-ylamino]-propyl}-carbamic Acid tert-Butyl Ester

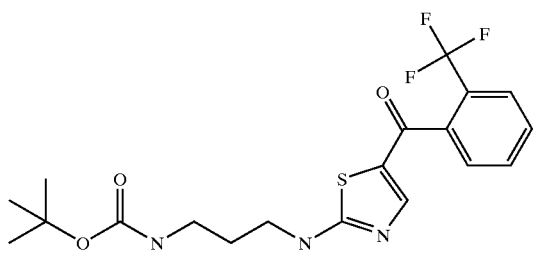

The title compound was synthesised from [3-(3-Dimethylaminomethylene-thioureido)-propyl]-carbamic acid tert-butyl ester and 2-trifluoromethyl phenacylbromide (literature: EP 432040) according to the procedure described for Example 25. MS (m/e): 429.9 (MH$^+$, 100%).

Example H

[2-(3-Amino-propylamino)-thiazol-5-yl]-phenyl-methanone; Hydrochloride

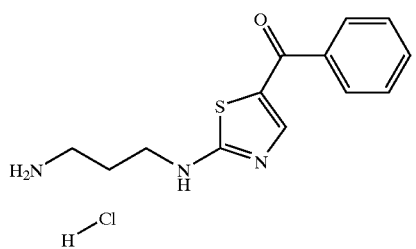

A mixture of 0.5 g (1.73 mmol) [3-(3-Dimethylaminomethylene-thioureido)-propyl]-carbamic acid tert-butyl ester, 0.448 g (2.25 mmol) phenacyl bromide (commercially available) and 0.723 ml (5.2 mmol) NEt₃ in 20 ml EtOH was heated to 100° C. for 16 h. After cooling to room temperature 3 ml of a 4N HCl solution in dioxane was added and the mixture was stirred for 2 h at 60° C. The mixture was concentrated, the precipitate was filtered off, washed with diethyl ether and dried to yield 0.505 g (81%) of the title compound.

1-H-NMR (300 MHz, DMSO-d6) δ=9.13 (s, br, 1H, NH), 8.04 (s, br, 2H, NH₂), 7.60 (m, 6H, Ph/thiazole), 3.43 (m, 2H, CH₂), 2.85 (m, 2H, CH₂), 1.85 (m, 2H, CH₂). MS (m/e): 262.2 (MH⁺, 100%).

Example I

[2-(3-Amino-propylamino)-thiazol-5-yl]-o-tolyl-methanone; Hydrochloride

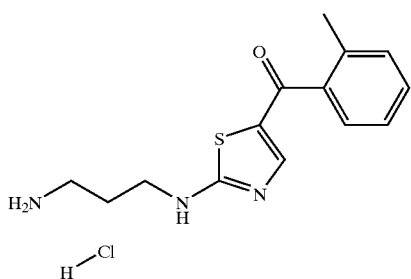

The title compound was synthesised from [3-(3-Dimethylaminomethylene-thioureido)-propyl]-carbamic acid tert-butyl ester and 2-methyl phenacyl bromide (literature: WO9907666) according to the procedure described for Example H. MS (m/e): 276.3 (MH⁺, 100%).

Example J

[2-(3-Amino-propylamino)-thiazol-5-yl]-(2-ethyl-phenyl)-methanone; Hydrochloride

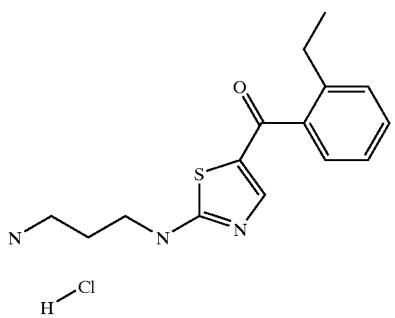

The title compound was synthesised from [3-(3-Dimethylaminomethylene-thioureido)-propyl]-carbamic acid tert-butyl ester and 2-ethyl phenacyl bromide according to the procedure described for Example H. MS (m/e): 290.3 (MH⁺, 100%).

Example K

[2-(3-Amino-propylamino)-thiazol-5-yl]-(2-fluoro-phenyl)-methanone; Hydrochloride

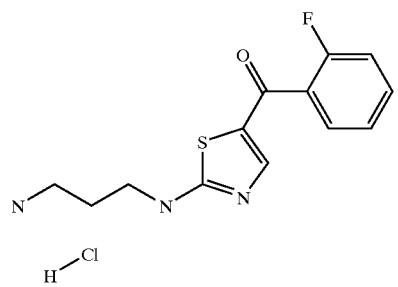

The title compound was synthesised from [3-(3-Dimethylaminomethylene-thioureido)-propyl]-carbamic acid tert-butyl ester 2-Fluoro-phenacyl bromide (commercially available) according to the procedure described for Example H. MS (m/e): 280.3 (MH⁺, 100%).

Example L

[2-(3-Amino-propylamino)-thiazol-5-yl]-(2-chloro-phenyl)-methanone; Hydrochloride

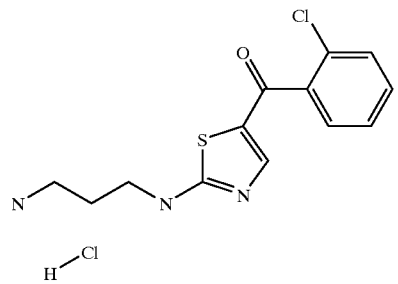

The title compound was synthesised from [3-(3-Dimethylaminomethylene-thioureido)-propyl]-carbamic acid tert-butyl ester 2-Chloro-phenacyl bromide (commercially available) according to the procedure described for Example H. MS (m/e): 296.4 (MH⁺, 100%).

Example M

[2-(3-Amino-propylamino)-thiazol-5-yl]-(2-trifluoromethyl-phenyl)-methanone; Hydrochloride

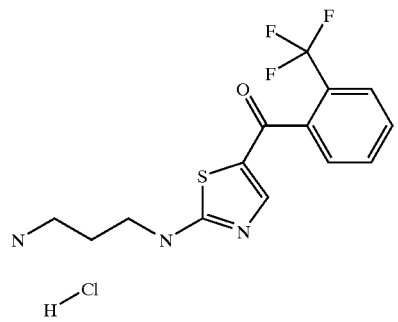

The title compound was synthesised from [3-(3-Dimethylaminomethylene-thioureido)-propyl]-carbamic acid tert-butyl ester 2-Trifluoromethyl-phenacyl bromide (literature: EP432040) according to the procedure described for Example H.

MS (m/e): 330.4 (MH⁺, 100%).

Example N

[2-(3-Amino-propylamino)-thiazol-5-yl]-(4-methyl-pyridin-3-yl)-methanone; Hydrochloride

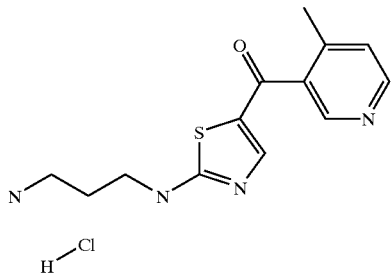

The title compound was synthesised from [3-(3-Dimethylaminomethylene-thioureido)-propyl]-carbamic acid tert-butyl ester and 2-Bromo-1-(4-methyl-pyridin-3-yl)-ethanone according to the procedure described for Example H. MS (m/e): 277.3 (MH⁺, 100%).

Example O 2-(3-Amino-propylamino)-thiazol-5-yl]-(3-methyl-pyridin-2-yl)-methanone; Hydrochloride

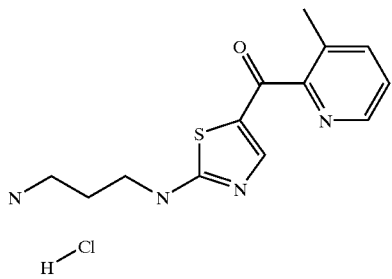

The title compound was synthesised from [3-(3-Dimethylaminomethylene-thioureido)-propyl]-carbamic acid tert-butyl ester and 2-Bromo-1-(3-methyl-pyridin-2-yl)-ethanone (literature: WO9935130) according to the procedure described for Example H. MS (m/e): 277.3 (MH⁺, 100%).

Example P

[2-(3-Amino-propylamino)-thiazol-5-yl]-(2-methyl-pyridin-3-yl)-methanone; Hydrochloride

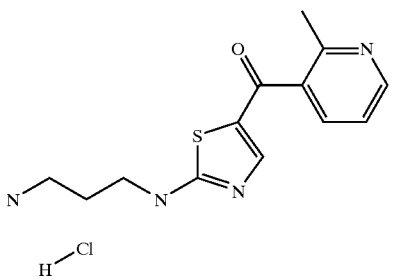

The title compound was synthesised from [3-(3-Dimethylaminomethylene-thioureido)-propyl]-carbamic acid tert-butyl ester and 2-Bromo-1-(2-methyl-pyridin-3-yl)-ethanone (Literature: J. Heterocycl. Chem. 1978, 15, 217) according to the procedure described for Example H. MS (m/e): 277.3 (MH⁺, 100%).

Example Q

[2-(3-Amino-propylamino)-thiazol-5-yl]-(3-methyl-pyrazin-2-yl)-methanone; Hydrochloride

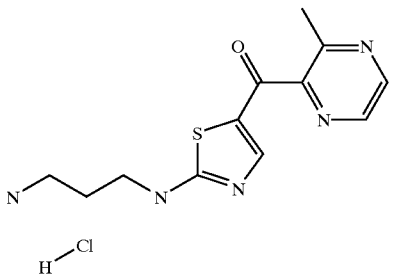

The title compound was synthesised from [3-(3-Dimethylaminomethylene-thioureido)-propyl]-carbamic acid tert-butyl ester and 2-Bromo-1-(3-methyl-pyrazin-2-yl)-ethanone according to the procedure described for Example H. MS (m/e): 278.3 (MH⁺, 100%).

Example R

[2-(3-Amino-propylamino)-thiazol-5-yl]-(3-methyl-thiophen-2-yl)-methanone; Hydrochloride

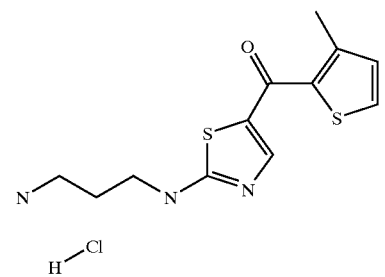

The title compound was synthesised from [3-(3-Dimethylaminomethylene-thioureido)-propyl]-carbamic acid tert-butyl ester and 2-Bromo-1-(3-methyl-thiophen-2- yl)-ethanone (Literature: EP432040) according to the procedure described for Example H. MS (m/e): 282.2 (MH+, 100%).

Example S

[2-(3-Amino-propylamino)-thiazol-5-yl]-pyridin-2-yl-methanone; Hydrochloride

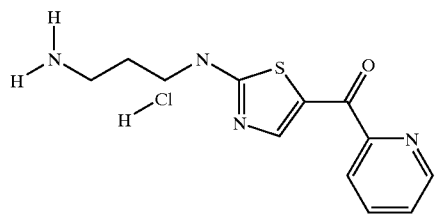

The title compound was synthesised from [3-(3-Dimethylaminomethylene-thioureido)-propyl]-carbamic acid tert-butyl ester and 2-(bromoacetyl)pyridine hydrobromide (commercially available) according to the procedure described for Example H. MS (m/e): 263.2 (MH+, 100%).

Example Z

[2-(3-Amino-propylamino)-thiazol-5-yl]-pyridin-3-yl-methanone; Hydrochloride

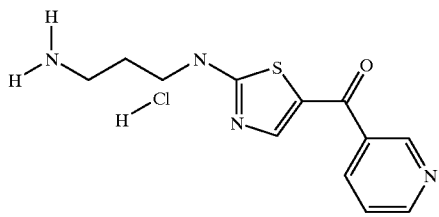

The title compound was synthesised from [3-(3-Dimethylaminomethylene-thioureido)-propyl]-carbamic acid tert-butyl ester and 3-(bromoacetyl)pyridine hydrobromide (commercially available) according to the procedure described for Example H. MS (m/e): 263.2 (MH+, 100%).

Example U

[2-(3-Amino-propylamino)-thiazol-5-yl]-pyridin-4-yl-methanone; Hydrochloride

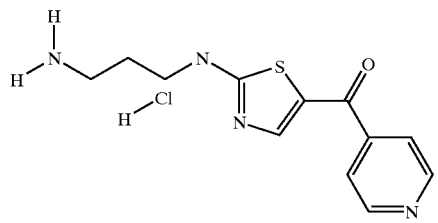

The title compound was synthesised from [3-(3-Dimethylaminomethylene-thioureido)-propyl]-carbamic acid tert-butyl ester and 2-bromo-1-(4-pyridinyl)-1-ethanone hydrobromide (commercially available) according to the procedure described for Example H. MS (m/e): 263.2 (MH+, 100%).

Example V

[2-(5-Amino-pentylamino)-thiazol-5-yl]-o-tolyl-methanone; Hydrochloride

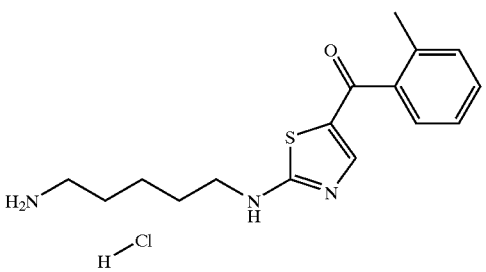

A mixture of 396 mg (1.25 mmol) [5-(3-Dimethylaminomethylene-thioureido)-pentyl]-carbamic acid tert-butyl ester, 388 mg (1.82 mmol) 2-methyl phenacylbromide (Literature: WO9907666) and 0.7 ml NEt3 in 8 ml ethanol was heated to 100° C. for 16 h. After evaporation to dryness the residue was taken up in 6 ml dioxane and treated with 3 ml of a 4N HCl in dioxane and stirred for 16 h at room temperature. After concentration the residue taken up in diethyl ether, the precipitate was filtered of and dried to yield 320 mg (75%) of the title compound. MS (m/e): 304.5 (MH+, 100%).

Example W

[2-(5-Amino-pentylamino)-thiazol-5-yl]-pyridin-2-yl-methanone; Hydrochloride

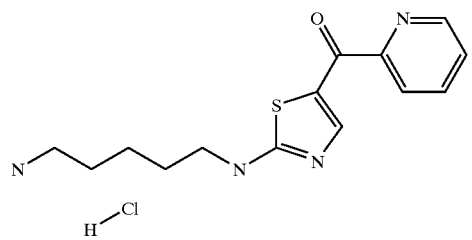

The title compound was synthesised from [5-(3-Dimethylaminomethylene-thioureido)-pentyl]-carbamic acid tert-butyl ester and 2-Bromo-1-pyridin-2-yl-ethanone (commercially available) according to the procedure described for Example V. MS (m/e): 291.4 (MH+, 100%).

Example X

[2-(5-Amino-pentylamino)-thiazol-5-yl]-pyridin-4-yl-methanone; Hydrochloride

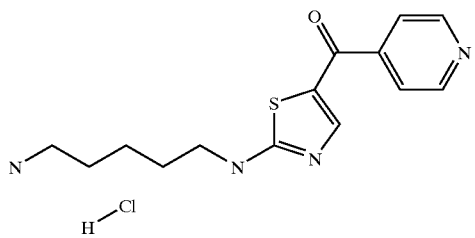

The title compound was synthesised from [5-(3-Dimethylaminomethylene-thioureido)-pentyl]-carbamic acid tert-butyl ester and 2-Bromo-1-pyridin-4-yl-ethanone (commercially available) according to the procedure described for Example V. MS (m/e): 291.3 (MH$^+$, 100%).

Example Y

[2-(5-Amino-pentylamino)-thiazol-5-yl]-(2-chloro-phenyl)-methanone; Hydrochloride

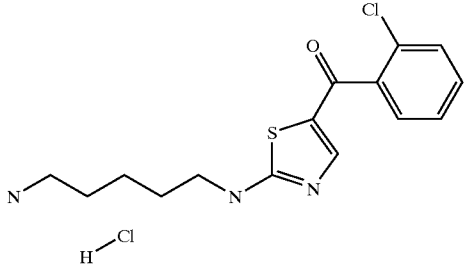

The title compound was synthesised from [5-(3-Dimethylaminomethylene-thioureido)-pentyl]-carbamic acid tert-butyl ester and 2-Bromo-1-(2-chloro-phenyl)-ethanone (commercially available) according to the procedure described for Example V. MS (m/e): 324.2 (MH$^+$, 100%).

Example 7

Thiophene-2-sulfonic Acid {3-[5-(2-Methyl-benzoyl)-thiazol-2-ylamino]-propyl}-amide

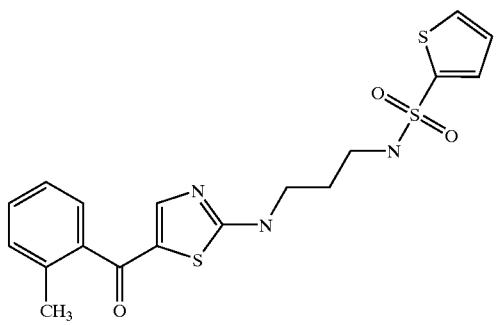

A mixture of 31.1 mg (0.1 mmol) [2-(3-Amino-propylamino)-thiazol-5-yl]-o-tolyl-methanone hydrochloride in 1 ml methanol, 18.2 mg (0.1 mmol) Thiophene-2-sulfonyl chloride in 1 ml DCM and 0.15 ml NEt$_3$ was stirred for 16 h at 50° C. After evaporation to dryness the residue was taken up in 1.5 ml MeOH/formic acid 1/1 and subjected to preparative HPLC separation on reversed phase eluting with an acetonitrile/water gradient. Evaporation of product fractions yielded 11.4 mg (27%) of the title compound.

MS (m/e): 386.3 ((M−H), 100%).

According to the procedure described for the synthesis of Example 7 further sulfonamides have been synthesised from [2-(3-Amino-propylamino)-thiazolyl- or [2-(5-Amino-pentylamino)-thiazolyl derivatives and sulfonyl chlorides. The results are shown in table 1 and comprise Example 1 to Example 24, Example 119 to Example 123 and Example 142 to Example 171, and Examples 180 to Example 233.

Example 31

Pentanoic Acid [3-(5-benzoyl-thiazol-2-ylamino]-propyl]-amide

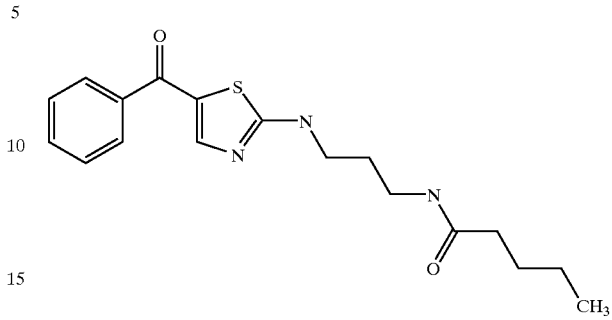

A mixture of 11.9 mg (0.04 mmol) [2-(3-Amino-propylamino)-thiazol-5-yl]-phenyl-methanone hydrochloride, 5.8 mg (0.048 mmol) pentanoyl chloride and 39 ul (0.28 mmol) NEt$_3$ in 1 ml methanol and 0.5 ml DCM was stirred at room temperature for 16 h. After evaporation to dryness the residue was taken up in 1.5 ml MeOH/formic acid 1/1 and subjected to preparative HPLC separation on reversed phase eluting with an acetonitrile/water gradient. Evaporation of product fractions yielded 6 mg (43%) of the title compound.

MS (m/e): 345.5 (MH$^+$, 100%).

According to the procedure described for the synthesis of Example 31 further amides have been synthesised from [2-(3-Amino-propylamino)-thiazolyl derivatives and acid chlorides. The results are shown in table 1 and comprise Example 29 to Example 88.

Example 98

1-(2-Methoxy-phenyl)-3-{3-[5-(2-methyl-benzoyl)-thiazol-2-ylamino]-propyl}-urea

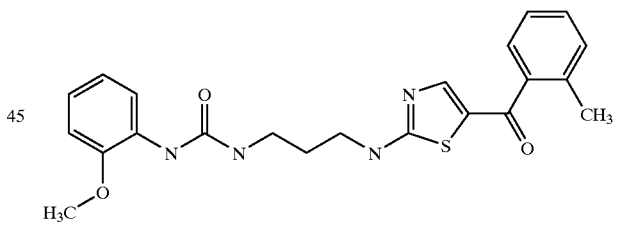

A mixture of 12.5 mg (0.04 mmol) [2-(3-Amino-propylamino)-thiazol-5-yl]-o-tolyl-methanone hydrochloride, 7.6 mg (0.05 mmol) 2-Methoxyphenyl isocyanate and 39 ul NEt$_3$ in 1 ml methanol was stirred for 16 h at room temperature. After evaporation to dryness the residue was taken up in 1.5 ml MeOH/formic acid 1/1 and subjected to preparative HPLC separation on reversed phase eluting with an acetonitrile/water gradient. Evaporation of product fractions yielded 7.9 mg (47%) of the title compound.

MS (m/e): 424.3 (M$^+$, 100%).

According to the procedure described for the synthesis of Example 98 further ureas have been synthesised from [2-(3-Amino-propylamino)-thiazolyl derivatives and isocyanates. The results are shown in table 1 and comprise Example 89 to Example 118.

Example Z 1-o-Tolyl-propane-1,2-dione

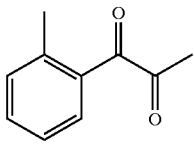

A mixture of 7 g (47.23 mmol) 1-o-Tolyl-propan-2-one, 30.5 g (0.141 mol) pyridinium chlorochromate and 11.2 g (0.141 mol) pyridine in 200 ml DCM was heated to reflux for 16 h. The mixture was filtered through a pad of silica and the filtrate was evaporated under reduced pressure. The residue was purified by flash column chromatography on silica eluting with ethyl acetate/n-hexane 1:4. The product fractions were evaporated to yield 1.178 g (15%) of the title compound.

1-H-NMR (300 MHz, DMSO-d6) δ=7.64 d, J=6 Hz, 1H, phenyl), 7.52 (d, J=6 Hz, 1H, phenyl), 7.38 (d, J=6 Hz, 2H, phenyl), 2.52 (s, 3H, $CH_3$), 2.49 (s, 3H, $CH_3$). MS (m/e): 162 ($M^+$, 100%).

Example AA

3-Bromo-1-o-tolyl-propane-1,2-dione

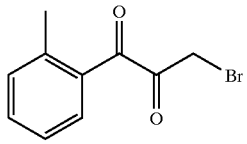

A mixture of 3 g (18.49 mmol) 1-o-Tolyl-propane-1,2-dione and 1.05 ml (20.34 mmol) bromine in 30 ml $CHCl_3$ and 0.53 ml acetic acid was heated to 70° C. for 16 h. The mixture was evaporated under reduced pressure to yield 4.35 g (98%) of the title compound.

1-H-NMR (300 MHz, DMSO-d6) δ=7.60 (m, 4H, phenyl), 2.52 (s, 2H, $CH_2$), 2.51 (s, 3H, $CH_3$). MS (m/e): 234.3 ($MH^+$, 100%).

Example AB

{3-[4-(2-Methyl-benzoyl)-thiazol-2-ylamino]-propyl}-carbamic Acid tert-Butyl Ester

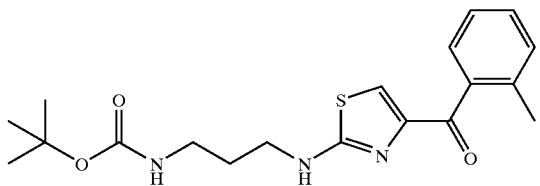

A mixture of 2.55 g (10.6 mmol) 3-Bromo-1-o-tolyl-propane-1,2-dione, 1.9 g (8.1 mmol) (3-thioureido-propyl)-carbamic acid tert-butyl ester and 5.66 ml (40.6 mmol) $NEt_3$ in 100 ml methanol was heated to 80° C. for 2 h. The reaction mixture was evaporated under reduced pressure and the residue was purifier by flash column chromatography on silica eluting with a gradient of heptane and ethyl acetate.

Evaporation of the product fractions yielded 2.17 g (71%) of the title compound as dark red oil.

1-H-NMR (300 MHz, DMSO-d6) δ=7.82 (s, br, 1H, NH), 7.38–7.27 (m, 5H, phenyl/thiazole), 6.84 (s, br, 1H, NH), 3.19 (m, 2H, $CH_2$), 2.97 (m, 2H, $CH_2$), 2.25 (s, 3H, $CH_3$), 1.65 (m, 2H, $CH_2$), 1.37 (s, 9H, $CH_3$). MS (m/e): 376.5 ($MH^+$, 100%).

Example AC

[2-(3-Amino-propylamino)-thiazol-4-yl]-o-tolyl-methanone; Hydrochloride

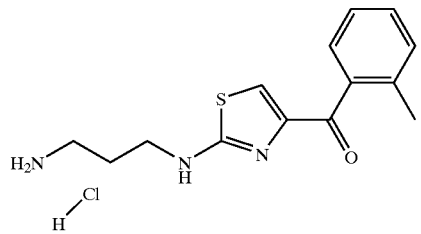

A mixture of 2.17 g (5.8 mmol) {3-[4-(2-Methyl-benzoyl)-thiazol-2-ylamino]-propyl}-carbamic acid tert-butyl ester and 30 ml 4N HCl in dioxane and 20 ml ethanol was stirred at room temperature for 16 h. The mixture was concentrated to yield 1.8 g (quant.) of the title compound.

1-H-NMR (300 MHz, DMSO-d6) δ=8.23 (s, br, 2H, $NH_2$), 7.45–7.35 (m, 5H, phenyl/thiazole), 6.0 (s, br, 1H, NH), 3.39 (m, 2H, $CH_2$), 2.86 (m, 2H, $CH_2$), 2.29 (s, 3H, $CH_3$), 1.91 (t, J=6 Hz, 2H, $CH_2$). MS (m/e): 276.3 ($MH^+$, 100%).

Example 138

Thiophene-2-sulfonic Acid {3-[4-(2-Methyl-benzoyl)-thiazol-2-ylamino]-propyl}-amide

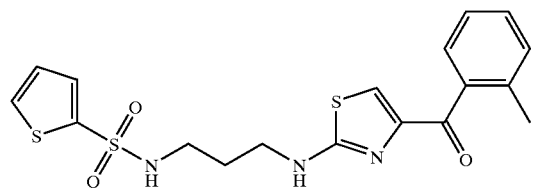

A solution of 15.6 mg (0.5 mmol) [2-(3-Amino-propylamino)-thiazol-4-yl]-o-tolyl-methanone hydrochloride in 1 ml methanol was treated with 11.9 mg (0.65 mmol) thiophene-2-sulfonyl chloride in 0.13 ml dioxane and 34.7 ul $NEt_3$. The mixture was stirred at 60° C. for 16 h and after addition of 0.5 ml formic acid subjected to preparative HPLC separation on reversed phase eluting with an acetonitrile/water gradient. Evaporation of the product fractions yielded 6.2 mg (29%) of the title compound.

MS (m/e): 422.3 ($MH^+$, 100%).

According to the procedure described for the synthesis of Example 138 further sulfonamides have been synthesised from thiazole derivatives and sulfonylchlorides. The results are shown in table 1 and comprise Example 132 to Example 141.

According to the procedure described for the synthesis of Example 138 amides have been synthesised with the temperature adjustment to room temperature from thiazole derivatives and acid chlorides. The results are shown in table 1 and comprise Example 126 to Example 129.

According to the procedure described for the synthesis of Example 138 ureas have been synthesised with the temperature adjustment to room temperature from thiazole derivatives and isocyanates. The results are shown in table 1 and comprise Example 130 and Example 131.

Example AD (5-Isothiocyanato-pentyl)-carbamic Acid tert-Butyl Ester

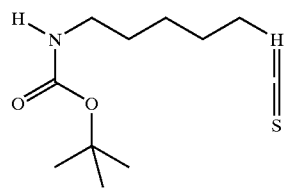

To a solution of 2 g (9.9 mmol) (5-Amino-pentyl)-carbamic acid tert-butyl ester in 40 ml THF at 0° C. was added 896 μl (14.83 mmol) CS$_2$ and allowed to stir at room temperature for 14 h. 623 mg (14.83 mmol) cyanamide and 4 drops NEt$_3$ was added and the mixture was heated to 4° C. for 3 h. The mixture was extracted with diethyl ether and the combined organic layers were dried with MgSO$_4$. After filtration and removal of the volatiles the residue was purified by flash column chromatography on silica eluting with ethyl acetate/cyclohexane 1:1. The evaporation of the product fractions yielded 2.24 g (93%) of the title compound.

1-H-NMR (250 MHz, CDCl$_3$) δ=4.58 (s, br, 1H, NH), 3.52 (t, J=6.5 Hz, 2H, NCH2), 3.13 (dd, J$_1$=6.5 Hz, J$_2$=4 Hz, 2H, NHC$\underline{H}_2$), 1.74 (m, 2H, CH$_2$), 1.50 (m, 4H, CH$_2$), 1.44 (s, 9H, CH$_3$).

MS (m/e): 262.3 (M+NH$_4$, 100%).

Example AE

{5-[3-(1-Amino-ethylidene)-thioureido]-pentyl}-carbamic Acid tert-Butyl Ester

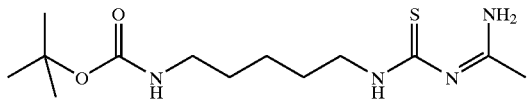

A solution of 245 mg (1 mmol) (5-Isothiocyanato-pentyl)-carbamic acid tert-butyl ester in 1 ml IN NaOH at 0° C. was treated with 94.5 mg (1 mmol) acetidine hydrochloride in 2 ml THF and allowed to stir for 5 h at 0° C. The mixture was extracted three times with 15 ml diethyl ether, the combined organic layers were dried with MgSO$_4$ and after filtration evaporated under reduced pressure to yield 297 mg (98%) of the title compound.

MS (m/e): 303.4 (M+H, 100%).

Example AF

{5-[4-Methyl-5-(2-methyl-benzoyl)-thiazol-2-ylamino]-pentyl}-carbamic Acid tert-Butyl Ester

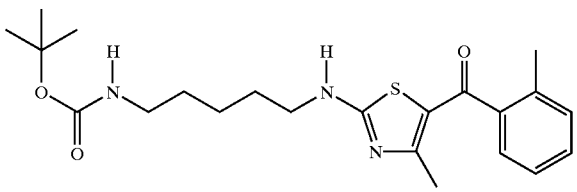

To a solution of 290 mg (0.96 mmol) {5-[3-(1-Amino-ethylidene)-thioureido]-pentyl}-carbamic acid tert-butyl ester in 5 ml ethanol was added 213 mg (1 mmol) o-Methylphenacyl bromide and 139 μl NEt3 and allowed to stir for 5 h at room temperature. Afterwards the mixture was directly applied to preparative HPLC on reversed phase eluting with an acetonitrile/water gradient. The evaporation of the product fractions yielded 180 mg (45%) of the title compound.

MS (m/e): 418.3 (M+H, 100%).

Example AG

[2-(5-Amino-pentylamino)-4-methyl-thiazol-5-yl]-o-tolyl-methanone Hydrochloride

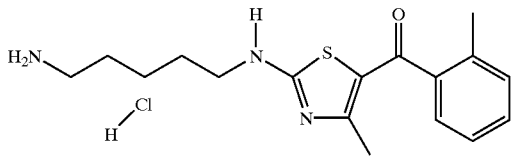

A solution of 170 mg (0.4 mmol) {5-[4-Methyl-5-(2-methyl-benzoyl)-thiazol-2-ylamino]-pentyl}-carbamic acid tert-butyl ester in 2 ml dioxane was treated with 1 ml 4N HCl in dioxane and allowed to react for 5 h at room temperature. The mixture was evaporated under reduced pressure to afford 143 mg (99%) of the title compound.

1-H-NMR (300 MHz, CDCl$_3$) δ=8.72 (s, br, 1H, NH), 7.75 (m, 2H, H-3/H-6), 7.30 (m, 2H, H-4/H-5), 4.80 (s, br, 2H, NH$_2$), 3.68 (t, J=6.4 Hz, 1H, NCH$_2$), 3.23 (m, 1H, NCH$_2$), 2.74 (m, 2H, NCH$_2$), 2.21 (s, 3H, CH$_3$), 1.91 (s, 3H, CH$_3$), 1.54 (m, 1.37 (m, 2H, CH$_2$). MS (m/e): 318.4 (M+H, 100%).

Example 172

N-{5-[4-Methyl-5-(2-methyl-benzoyl)-thiazol-2-ylamino]-pentyl}-benzenesulfonamide

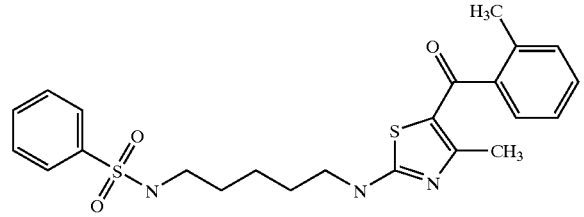

A solution of 18 mg (0.05 mmol) [2-(5-Amino-pentylamino)-4-methyl-thiazol-5-yl]-o-tolyl-methanone hydrochloride in 1 ml ethanol was treated with 10.6 mg (0.06 mmol) benzenesulfonylchloride and 21 ml NEt₃. The mixture was allowed to stir for 15 h at room temperature and afterwards subjected to preparative HPLC separation on reversed phase eluting with an acetonitrile/water gradient. Evaporation of the product fractions yielded 12.6 mg (55%) of the title compound.

MS (m/e): 458.3 (M+H, 100%).

AH (2-Thioureido-ethyl)-carbamic Acid tert-Butyl Ester

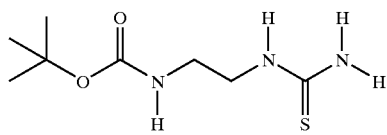

The title compound was synthesised from (2-Amino-ethyl)-carbamic acid tert-butyl ester. The compound is described in literature: WO0121623A1

Example AI

[2-(3-Dimethylaminomethylene-thioureido)-ethyl]-carbamic Acid tert-Butyl Ester

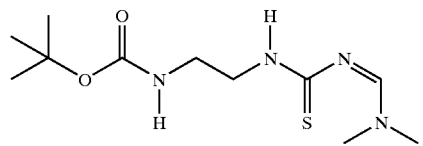

The title compound was synthesised from (2-Thioureido-ethyl)-carbamic acid tert-butyl ester and Dimethylformamide dimethyl acetal according to the procedure described for Example C in 51% yield. MS (m/e): 275.4 (MH⁺, 100%).

Example AJ

{2-[5-(2-Methyl-benzoyl)-thiazol-2-ylamino]-ethyl}-carbamic Acid tert-Butyl Ester

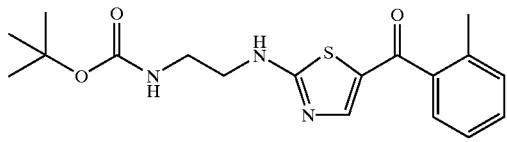

The title compound was synthesised from [2-(3-Dimethylaminomethylene-thioureido)-ethyl]-carbamic acid tert-butyl ester and 2-methyl phenacylbromide (Literature: WO9907666) according to the procedure described for Example 25 in 75% yield. MS (m/e): 362.1 (MH⁺, 100%).

Example AK

[2-(2-Amino-ethylamino)-thiazol-5-yl]-o-tolyl-methanone; Hydrochloride

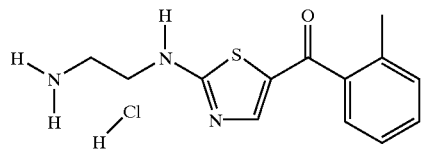

The title compound was synthesised from {2-[5-(2-Methyl-benzoyl)-thiazol-2-ylamino]-ethyl}-carbamic acid tert-butyl ester according to the procedure described for Example AC in quantitative yield. MS (m/e): 261.7 (MH⁺, 100%).

Example AL (4-Thioureido-butyl)-carbamic Acid tert-Butyl Ester

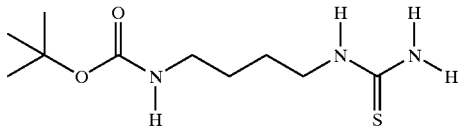

The title compound was synthesised from (4-Amino-butyl)-carbamic acid tert-butyl ester. The compound is described in literature: WO0102379A1

Example AM

[4-(3-Dimethylaminomethylene-thioureido)-butyl]-carbamic Acid tert-Butyl Ester

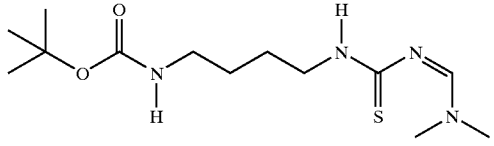

The title compound was synthesised from (4-Thioureido-butyl)-carbamic acid tert-butyl ester and Dimethylformamide dimethyl acetal according to the procedure described for Example C in 76% yield. MS (m/e): 303.3 (MH⁺, 100%).

Example AN

{4-[5-(2-Methyl-benzoyl)-thiazol-2-ylamino]-butyl}-carbamic Acid tert-Butyl Ester

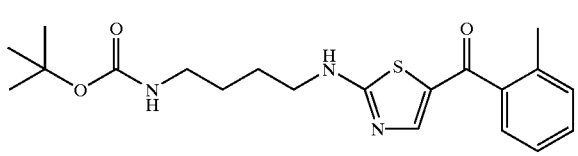

The title compound was synthesised from [4-(3-Dimethylaminomethylene-thioureido)-butyl]-carbamic acid tert-butyl ester and 2-methyl phenacylbromide (Literature: WO9907666) according to the procedure described for Example 25 in 69% yield. MS (m/e): 390.2 (MH⁺, 100%).

Example AO

[2-(4-Amino-butylamino)-thiazol-5-yl]-o-tolyl-methanone; Hydrochloride

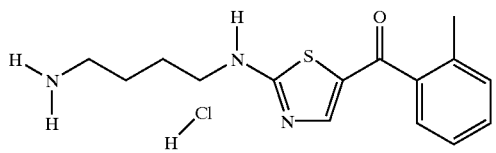

The title compound was synthesised from {4-[5-(2-Methyl-benzoyl)-thiazol-2-ylamino]-butyl}-carbamic acid tert-butyl ester according to the procedure described for Example AC in quantitative yield. MS (m/e): 289.7 (MH+, 100%).

Example AP

Methyl-(4-thioureido-propyl)-carbamic Acid tert-Butyl Ester

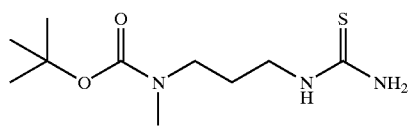

The title compound was synthesised from (3-Amino-propyl)-methyl-carbamic acid tert-butyl ester according to the procedure described for Example A (MS (m/e): 234.3 (MH$^+$, 100%).

Example AQ

[4-(3-Dimethylaminomethylene-thioureido)-propyl]-methyl-carbamic Acid tert-Butyl Ester

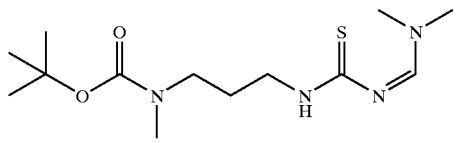

The title compound was synthesised from Methyl-(4-thioureido-butyl)-carbamic acid tert-butyl ester and Dimethylformamide dimethyl acetal according to the procedure described for Example C in 39% yield. MS (m/e): 328.9 (MH$^+$, 100%).

Example AR

Methyl-{3-[5-(2-methyl-benzoyl)-thiazol-2-ylamino]-propyl}-carbamic Acid tert-Butyl Ester

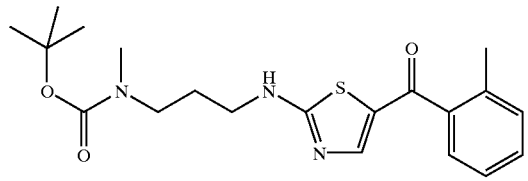

The title compound was synthesised from [4-(3-Dimethylaminomethylene-thioureido)-butyl]-methyl-carbamic acid tert-butyl ester and 2-methyl phenacylbromide (Literature: WO9907666) according to the procedure described for Example 25 in 78% yield. MS (m/e): 390.3 (MH+, 100%).

Example AS

[2-(3-Methylamino-propylamino)-thiazol-5-yl]-o-tolyl-methanone; Hydrochloride

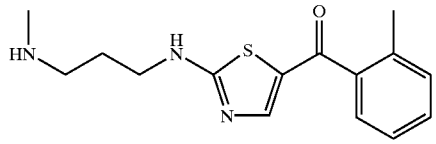

The title compound was synthesised from Methyl-{3-[5-(2-methyl-benzoyl)-thiazol-2-ylamino]-propyl}-carbamic acid tert-butyl ester according to the procedure described for Example AC in quantitative yield. MS (m/e): 289.1 (MH+, 100%).

Example AT

[2-(3-Amino-propylamino)-thiazol-5-yl]-o-tolyl-methanone

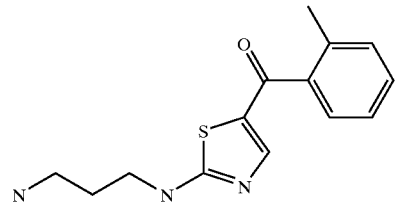

339 mg {3-[5-(2-Methyl-benzoyl)-thiazol-2-ylamino]-propyl}-carbamic acid tert-butyl ester was added to a solution of 25% aqueous hydrochloric acid in dioxane. The mixture was stirred 1 h at room temperature and maintained overnight in the refrigerator. The mixture was poured into saturated aqueous sodium bicarbonate solution (50 ml). The organics were extracted with dichloromethane (3×50 ml), dried over magnesium sulfate and evaporated under reduced pressure to afford the title compound as yellow foam (254 mg) which was used without further purification.

Example AU

N-{3-[5-(2-Methyl-benzoyl)-thiazol-2-ylamino]-propyl}-N'-(1,1-dimethylethyl)-sulfamide

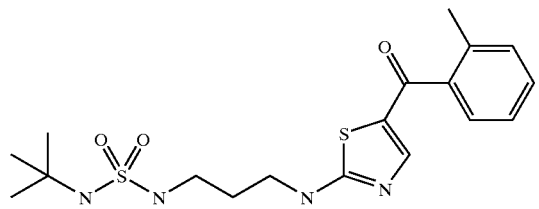

900 mg {3-[5-(2-Methyl-benzoyl)-thiazol-2-ylamino]-propyl}-carbamic acid tert-butyl ester was dissolved in diethyl ether and hydrogen chloride in ether added dropwise with stirring. The mixture was stirred overnight at room temperature and poured into saturated aqueous sodium bicarbonate solution. The organics were extracted with dichloromethane (3×25 ml), dried over magnesium sulfate and evaporated under reduced pressure to afford [2-(3-Amino-propylamino)-thiazol-5-yl]-o-tolyl-methanone as a yellow gum (579 mg, 88%). A solution of 0.22 ml tert-butanol in hexane (2 ml) was cautiously added to a stirred solution of 0.2 ml chlorosulfonyl isocyanate in hexane (5 ml). The resulting white precipitate was stirred until it had dissolved (1.5 h) and the mixture cooled to −78° C. before the slow addition of a solution of [2-(3-Amino-propylamino)-thiazol-5-yl]-o-tolyl-methanone and 0.4 ml triethylamine in dichloromethane. The cooling bath was removed and the yellow mixture allowed to reach room temperature and stirred 2 h at room temperature. The mixture was poured into water and the organics extracted with ethyl acetate (2×25 ml). The combined organics were washed with brine, dried over magnesium sulfate and evaporated. The resulting oil was purified by column chromatography on silica gel (150 g, 2:1 ethyl acetate/hexane) to afford the title compound (241 mg, 24%) as a pale yellow oil. MS (m/e): 409.3 (M−H, 100%)

Example AV

N-{3-[5-(2-Methyl-benzoyl)-thiazol-2-ylamino]-propyl}-acetamide

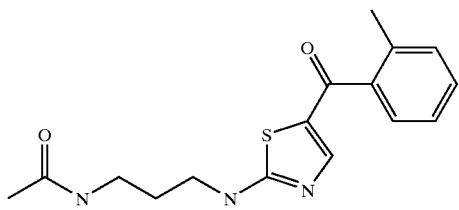

25% Aqueous hydrochloric acid was added dropwise to a solution of RO4386677-000 in 2-propanol. The mixture was stirred 1 h at room temperature and kept in the refrigerator over the week-end. The solvent was evaporated under reduced pressure and the residue triturated with diethyl ether. Ethyl acetate (40 ml) was added and the hydrochloride quenched by the addition of saturated aqueous sodium bicarbonate solution (50 ml). The aqueous phase was extracted with dichloromethane (5×75 ml).The combined organic phases were dried over sodium sulfate and evaporated. The residue was purified by column chromatography on silica gel. The only product isolated was the title compound, as a yellow oil which solidified on standing. Recrystallisation from a mixture of ethyl acetate, dichloromethane and hexane afforded the pure product as a light yellow solid (275 mg, 13%). MS (m/e): 318.3 (M+H, 100%).

Example AW

4-Methyl-N-{3-[5-(2-methyl-benzoyl)-thiazol-2-ylamino]-propyl}-benzenesulfonamide

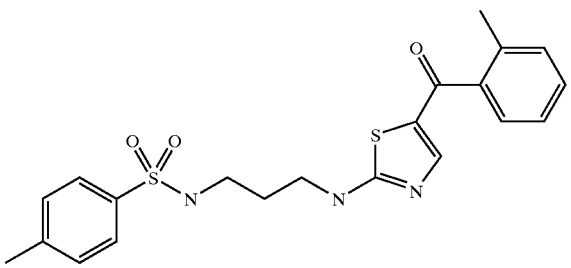

[2-(3-Amino-propylamino)-thiazol-5-yl]-o-tolyl-methanone was dissolved in dichloromethane and triethylamine and toluene-4-sulfonyl chloride added. The mixture was stirred overnight at room temperature, poured into 1 M pH4 phosphate buffer (5 ml) and extracted with dichloromethane (3×10 ml). The combined organic phases were dried over magnesium sulfate and evaporated. The oily residue was purified by column chromatography on silica gel (13:7 hexane/acetone eluant), using a small amount of dichloromethane to apply the mixture to the column. The title compound was isolated as an off-white solid. MS (m/e): 428.3 (M−H, 100%).

Example AX

Ethanesulfonic Acid {3-[5-(2-Methyl-benzoyl)-thiazol-2-ylamino]-propyl}-amide

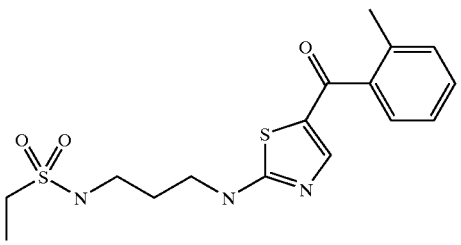

The title compound was produced from [2-(3-Amino-propylamino)-thiazol-5-yl]-o-tolyl-methanone and ethane-sulfonyl chloride according to the procedure described for Example AW. The product was isolated as an off-white solid. MS (m/e): 468.3 (M+H, 100%).

Example AY 2,2,2-Trifluoro-ethanesulfonic Acid {3-[5-(2-Methyl-benzoyl)-thiazol-2-ylamino]-propyl}-amide

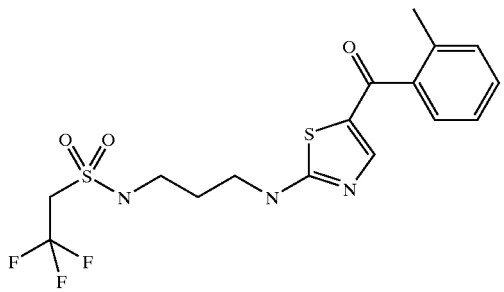

The title compound was produced from [2-(3-Amino-propylamino)-thiazol-5-yl]-o-tolyl-methanone and 2,2,2-trifluoroethanesulfonyl chloride according to the procedure described for Example AW. The product was isolated as an orange gum. MS (m/e): 422.3 (M+H, 100%).

Example AZ

Methanesulfonic Acid {3-[5-(2-Methyl-benzoyl)-thiazol-2-ylamino]-propyl}-amide

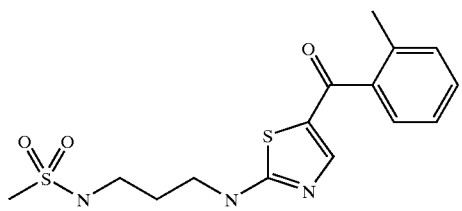

The title compound was produced from [2-(3-Amino-propylamino)-thiazol-5-yl]-o-tolyl-methanone and methanesulfonyl chloride according to the procedure described for Example AW. The product was isolated as an orange gum. MS (m/e): 352.2 (M−H, 100%).

Example BA

Propane-2-sulfonic Acid {3-[5-(2-Methyl-benzoyl)-thiazol-2-ylamino]-propyl}-amide

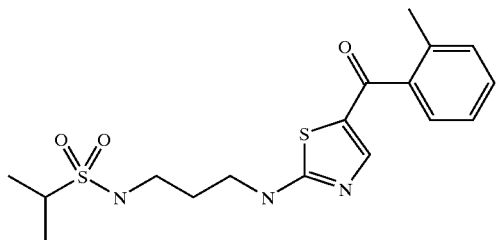

The title compound was produced from [2-(3-Amino-propylamino)-thiazol-5-yl]-o-tolyl-methanone and 2-propanesulfonyl chloride according to the procedure described for Example AW. The product was isolated as an orange gum. MS (m/e): 380.2 (M−H, 100%).

Example BB

Naphthalene-1-sulfonic Acid {3-[5-(2-Methyl-benzoyl)-thiazol-2-ylamino]-propyl}-amide

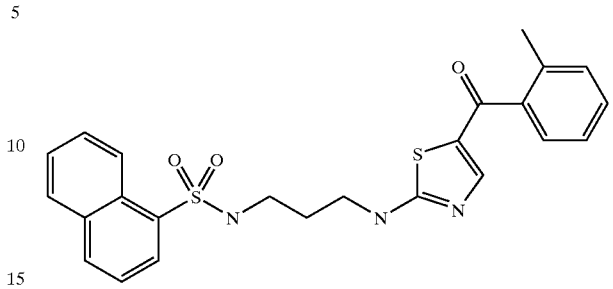

The title compound was produced from [2-(3-Amino-propylamino)-thiazol-5-yl]-o-tolyl-methanone and 1-naphthalenesulfonyl chloride according to the procedure described for Example AW. The product was isolated as an off-white gum. MS (m/e): 464.1 (M−H, 100%).

Example BC 1,1-Dimethylethyl{{3-[5-(2-methyl-benzoyl)-thiazol-2-ylamino]-propylamino}sulfonyl]-carbamate

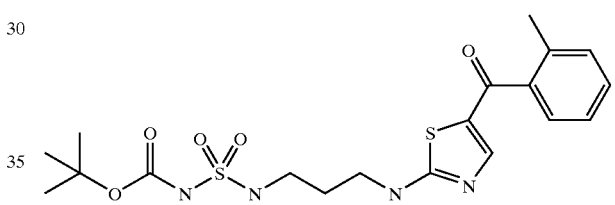

To a solution of 43 mg [2-(3-Amino-propylamino)-thiazol-5-yl]-o-tolyl-methanone in dichloromethane was added 49 mg 4-(dimethylamino)-1-[[[(1,1-dimethylethoxy)carbonyl]amino]sulfonyl]-pyridinium (Organic Letters, 2001,3,2241). The mixture was stirred overnight at room temperature. The solvent was evaporated under reduced pressure and the solid residue purified by column chromatography on silica gel (15 g, 7:3 ethyl acetate/hexane eluant), using a small amount of dichloromethane to apply the mixture to the column. The product was isolated as an off-white solid (28 mg, 40%).

MS (m/e): 453.2 (M−H, 100%).

Example BD

{3-[3-(1-Amino-ethylidene)-thioureido]-propyl}-carbamic Acid tert-Butyl Ester

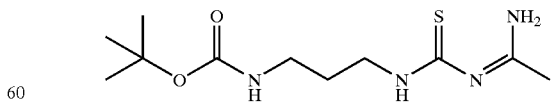

The title compound was prepared from (3-isothiocyanatopropyl)-carbamic acid tert-butyl ester and acetamidine hydrochloride as a colorless gum (quantitative yield) according to the procedure described for Example AE. MS (m/e): 275.2 (M+H, 100%).

Example BE

3-[5-(2-Ethyl-benzoyl)-4-methyl-thiazol-2-ylamino]-propyl}-carbamic Acid tert-Butyl Ester

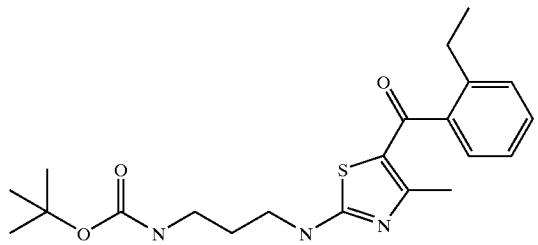

A mixture of 0.60 g {3-[3-(1-Amino-ethylidene)-thioureido]-propyl}-carbamic acid tert-butyl ester and 0.54 g 2-bromo-1-(2-ethyl-phenyl)-ethanone (Example G) were dissolved in N,N-dimethylformamide and stirred overnight at room temperature. 0.33 ml Triethylamine were added and the mixture stirred 72 h at room temperature. The mixture was diluted with dichloromethane, washed twice with water and once with brine, dried over magnesium sulfate, filtered and evaporated to afford the title compound (435 mg) as a pale yellow solid (49%). MS (m/e): 404.5 (M+H, 100%).

Example BF

Naphthalene-1-sulfonic Acid {3-[5-(2-Ethyl-benzoyl)-4-methyl-thiazol-2-ylamino]-propyl}-amide

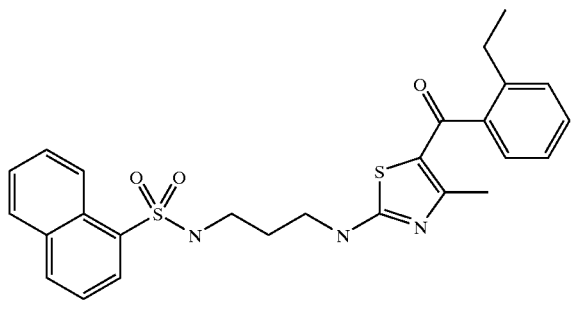

88 mg {3-[5-(2-Ethyl-benzoyl)-4-methyl-thiazol-2-ylamino]-propyl}-carbamic acid tert-butyl ester was dissolved in dioxane and 0.15 ml 25% aqueous hydrochloric acid added dropwise. The mixture was stirred 4 h at room temperature and evaporated to dryness. Toluene was added and the mixture evaporated to dryness and dried overnight in vacuo. The residue was taken up in dichloromethane and 50 mg naphthalene-1-sulfonyl chloride and 0.14 ml triethylamine added. The mixture was stirred overnight at room temperature and partitioned between water and dichloromethane. The organic phase was dried over magnesium sulfate and evaporated to afford the title compound (77 mg, 71%) as a yellow oil. MS (m/e): 492.2 (M+H, 100%).

Example BG

Thiophene-2-sulfonic Acid {3-[5-(2-Ethyl-benzoyl)-4-methyl-thiazol-2-ylamino]-propyl}amide

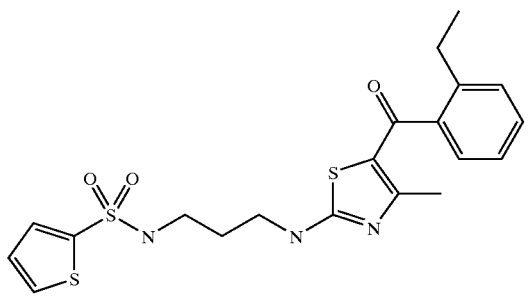

The title compound was prepared from {3-[5-(2-Ethyl-benzoyl)-4-methyl-thiazol-2-ylamino]-propyl}-carbamic acid tert-butyl ester and thiophene-2-sulfonyl chloride according to example BF. Off-white oil, 55%. MS (m/e): 448.1 (M+H, 100%).

Example BH

N-{3-[5-(2-Ethyl-benzoyl)-4-methyl-thiazol-2-ylamino]-propyl}-2-methoxy-5-methyl-benzenesulfonamide

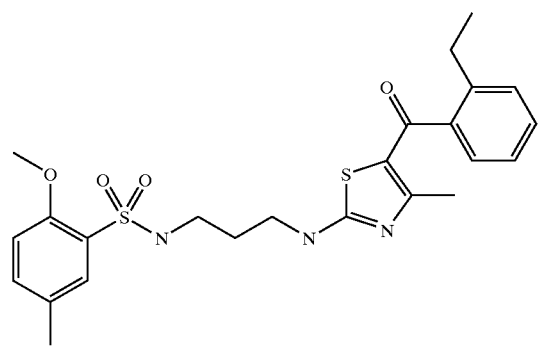

The title compound was prepared from {3-[5-(2-Ethyl-benzoyl)-4-methyl-thiazol-2-ylamino]-propyl}-carbamic acid tert-butyl ester and 6-methoxy-m-toluenesulfonyl chloride according to example XX. Light yellow oil, 67%. MS (m/e): 486.3 (M+H, 100%).

According to Example 172 further sulfonamide derivatives have been synthesised from the corresponding aminothiazole derivative and a sulfonylchloride. The results are compiled in the table and comprise Examples 172–179.

| Ex. | Educts | Name | Mass analysis |
|---|---|---|---|
| 1. | [2-(3-Amino-propylamino)-thiazol-5-yl]-pyridin-2-yl-methanone; hydrochloride and 2-Fluorophenylsulfonyl chloride | 2-Fluoro-N-{3-[5-(pyridine-2-carbonyl)-thiazol-2-ylamino]-propyl}benzenesulfonamide | 419.2 (M − H⁺)⁻ |
| 2. | [2-(3-Amino-propylamino)-thiazol-5-yl]-pyridin-2-yl-methanone; hydrochloride and 2-methoxy-5-methylphenyl-sulfonyl chloride | 2-Methoxy-5-methyl-N-{3-[5-(pyridine-2-carbonyl)-thiazol-2-ylamino]-propyl}-benzenesulfonamide | 445.3 (M − H⁺)⁻ |
| 3. | [2-(3-Amino-propylamino)-thiazol-5-yl]-pyridin-3-yl-methanone; hydrochloride and 2-methoxy-5-methylphenyl-sulfonyl chloride | 2-Methoxy-5-methyl-N-{3-[5-(pyridine-3-carbonyl)-thiazol-2-ylamino]-propyl}-benzenesulfonamide | 445.3 (M − H⁺)⁻ |
| 4. | [2-(3-Amino-propylamino)-thiazol-5-yl]-pyridin-4-yl-methanone; hydrochloride and 2-methoxy-5-methylphenyl-sulfonyl chloride | 2-Methoxy-5-methyl-N-{3-[5-(pyridine-4-carbonyl)-thiazol-2-ylamino]-propyl}-benzenesulfonamide | 445.3 (M − H⁺)⁻ |
| 5. | [2-(3-Amino-propylamino)-thiazol-5-yl]-o-tolyl-methanone; hydrochloride and 2-Fluorophenylsulfonyl chloride | 2-Fluoro-N-{3-[5-(2-methyl-benzoyl)-thiazol-2-ylamino]-propyl}-benzenesulfonamide | 432.3 (M − H⁺)⁻ |
| 6. | [2-(3-Amino-propylamino)-thiazol-5-yl]-o-tolyl-methanone; hydrochloride and 4-methoxyphenylsulfonyl chloride | 4-Methoxy-N-{3-[5-(2-methyl-benzoyl)-thiazol-2-ylamino]-propyl}-benzenesulfonamide | 444.3 (M − H⁺)⁻ |
| 7. | [2-(3-Amino-propylamino)-thiazol-5-yl]-o-tolyl-methanone; hydrochloride and 2-thiophenylsulfonyl chloride | Thiophene-2-sulfonic acid {3-[5-(2-methyl-benzoyl)-thiazol-2-ylamino]-propyl}-amide | 420.2 (M − H⁺)⁻ |
| 8. | [2-(3-Amino-propylamino)-thiazol-5-yl]-o-tolyl-methanone; hydrochloride and 2-methoxy-5-methylphenylsulfonyl chloride | 2-Methoxy-5-methyl-N-{3-[5-(2-methyl-benzoyl)-thiazol-2-ylamino]-propyl}-benzenesulfonamide | 458.3 (M − H⁺)⁻ |
| 9. | [2-(3-Amino-propylamino)-thiazol-5-yl]-o-tolyl-methanone; hydrochloride and 4-fluorophenylsulfonyl chloride | 4-Fluoro-N-{3-[5-(2-methyl-benzoyl)-thiazol-2-ylamino]-propyl}-benzenesulfonamide | 432.3 (M − H⁺)⁻ |
| 10. | [2-(3-Amino-propylamino)-thiazol-5-yl]-o-tolyl-methanone; hydrochloride and 2-methylphenylsulfonyl chloride | 2-Methyl-N-{3-[5-(2-methyl-benzoyl)-thiazol-2-ylamino]-propyl}-benzenesulfonamide | 428.4 (M − H⁺)⁻ |
| 11. | [2-(3-Amino-propylamino)-thiazol-5-yl]-o-tolyl-methanone; hydrochloride and 3-fluorophenylsulfonyl chloride | 3-Fluoro-N-{3-[5-(2-methyl-benzoyl)-thiazol-2-ylamino]-propyl}-benzenesulfonamide | 432.4 (M − H⁺)⁻ |
| 12. | [2-(3-Amino-propylamino)-thiazol-5-yl]-o-tolyl-methanone; hydrochloride and 2-chloro-5-(trifluoromethyl)phenylsulfonyl chloride | 2-Chloro-N-{3-[5-(2-methyl-benzoyl)-thiazol-2-ylamino]-propyl}-5-trifluoromethyl-benzenesulfonamide | 516.1 (M − H⁺)⁻ |
| 13. | [2-(3-Amino-propylamino)-thiazol-5-yl]-o-tolyl-methanone; hydrochloride and phenylsulfonyl chloride | N-{3-[5-(2-Methyl-benzoyl)-thiazol-2-ylamino]-propyl}-benzenesulfonamide | 415.5 (M − H⁺)⁻ |
| 14. | [2-(3-Amino-propylamino)-thiazol-5-yl]-o-tolyl-methanone; hydrochloride and 3-methoxyphenylsulfonyl chloride | 3-Methoxy-N-{3-[5-(2-methyl-benzoyl)-thiazol-2-ylamino]-propyl}-benzenesulfonamide | 444.3 (M − H⁺)⁻ |
| 15. | [2-(3-Amino-propylamino)-thiazol-5-yl]-(2-chloro-phenyl)-methanone; hydrochloride and 2-fluorophenylsulfonyl chloride | N-{3-[5-(2-Chloro-benzoyl)-thiazol-2-ylamino]-propyl}-2-fluoro-benzenesulfonamide | 452.2 (M − H⁺)⁻ |
| 16. | [2-(3-Amino-propylamino)-thiazol-5-yl]-(2-chloro-phenyl)-methanone; hydrochloride and 4-methoxyphenylsulfonyl chloride | N-{3-[5-(2-Chloro-benzoyl)-thiazol-2-ylamino]-propyl}-4-methoxy-benzenesulfonamide | 464.2 (M − H⁺)⁻ |
| 17. | [2-(3-Amino-propylamino)-thiazol-5-yl]-(2-chloro-phenyl)-methanone; hydrochloride and 2-thiophenylsulfonyl chloride | Thiophene-2-sulfonic acid {3-[5-(2-chloro-benzoyl)-thiazol-2-ylamino]-propyl}-amide | 440.2 (M − H⁺)⁻ |
| 18. | [2-(3-Amino-propylamino)-thiazol-5-yl]-(2-chloro-phenyl)-methanone; hydrochloride and 2-methoxy-5-methylphenyl-sulfonyl chloride | N-{3-[5-(2-Chloro-benzoyl)-thiazol-2-ylamino]-propyl}-2-methoxy-5-methyl-benzenesulfonamide | 478.2 (M − H⁺)⁻ |
| 19. | [2-(3-Amino-propylamino)-thiazol-5-yl]-(2-chloro-phenyl)-methanone; hydrochloride and 4-fluorophenylsulfonyl chloride | N-{3-[5-(2-Chloro-benzoyl)-thiazol-2-ylamino]-propyl}-4-fluoro-benzenesulfonamide | 452.2 (M − H⁺)⁻ |
| 20. | [2-(3-Amino-propylamino)-thiazol-5-yl]-(2-chloro-phenyl)-methanone; hydrochloride and 2-methylphenylsulfonyl chloride | N-{3-[5-(2-Chloro-benzoyl)-thiazol-2-ylamino]-propyl}-2-methyl-benzenesulfonamide | 448.2 (M − H⁺)⁻ |
| 21. | [2-(3-Amino-propylamino)-thiazol-5-yl]-(2-chloro-phenyl)-methanone; hydrochloride and 3-fluorophenylsulfonyl chloride | N-{3-[5-(2-Chloro-benzoyl)-thiazol-2-ylamino]-propyl}-3-fluoro-benzenesulfonamide | 452.2 (M − H⁺)⁻ |
| 22. | [2-(3-Amino-propylamino)-thiazol-5-yl]-(2-chloro-phenyl)-methanone; hydrochloride and 2-chloro-5-(trifluoromethyl)-phenylsulfonyl chloride | 2-Chloro-N-{3-[5-(2-chloro-benzoyl)-thiazol-2-ylamino]-propyl}-5-trifluoromethyl-benzenesulfonamide | 536.1 (M − H⁺)⁻ |
| 23. | [2-(3-Amino-propylamino)-thiazol-5-yl]-(2-chloro-phenyl)-methanone; hydrochloride and phenylsulfonyl chloride | N-{3-[5-(2-Chloro-benzoyl)-thiazol-2-ylamino]-propyl}-benzenesulfonamide | 434.3 (M − H⁺)⁻ |
| 24. | [2-(3-Amino-propylamino)-thiazol-5-yl]-(2-chloro-phenyl)-methanone; hydrochloride and 3-methoxyphenylsulfonyl chloride | N-{3-[5-(2-Chloro-benzoyl)-thiazol-2-ylamino]-propyl}-3-methoxy-benzenesulfonamide | 464.2 (M − H⁺)⁻ |
| 25. | 2-methyl phenacylbromide and [3-(3-dimethylamino-methylene-thioureido)-propyl]-carbamic acid tert-butyl ester | {3-[5-(2-Methyl-benzoyl)-thiazol-2-ylamino]-propyl}-carbamic acid tert-butyl ester | 375.9 MH+ |
| 26. | [3-(3-dimethylaminomethylene-thioureido)-propyl]-carbamic acid tert-butyl ester and 2-chlorophenacylbromide | 3-[5-(2-Chloro-benzoyl)-thiazol-2-ylamino]-propyl}-carbamic acid tert-butyl ester | 395.8 MH+ |
| 27. | [3-(3-dimethylaminomethylene-thioureido)-propyl]-carbamic acid tert-butyl ester and 2-ethylphenacylbromide | {3-[5-(2-Ethyl-benzoyl)-thiazol-2-ylamino]-propyl}-carbamic acid tert-butyl ester | 389.9 MH+ |
| 28. | [3-(3-dimethylaminomethylene-thioureido)-propyl]-carbamic acid tert-butyl ester and 2-trifluoromethylphenacylbromide | {3-[5-(2-Trifluoromethyl-benzoyl)-thiazol-2-ylamino]-propyl}-carbamic acid tert-butyl ester | 429.9 MH+ |
| 29. | [2-(3-Amino-propylamino)-thiazol-5-yl]-o-tolyl-methanone; hydrochloride and cyclohexanecarbonyl chloride | Cyclohexanecarboxylic acid {3-[5-(2-methyl-benzoyl)-thiazol-2-ylamino]-propyl}-amide | 386.4 MH+ |
| 30. | [2-(3-Amino-propylamino)-thiazol-5-yl]-(2-ethyl-phenyl)-methanone; hydrochloride and cyclohexanecarbonyl chloride | Cyclohexanecarboxylic acid {3-[5-(2-ethyl-benzoyl)-thiazol-2-ylamino]-propyl}-amide | 400.5 MH+ |
| 31. | [2-(3-Amino-propylamino)-thiazol-5-yl]-phenyl-methanone; hydrochloride and pentanoyl chloride | Pentanoic acid [3-(5-benzoyl-thiazol-2-ylamino)-propyl]-amide | 345.5 MH+ |
| 32. | [2-(3-Amino-propylamino)-thiazol-5-yl]-o-tolyl-methanone; hydrochloride and pentanoyl chloride | Pentanoic acid {3-[5-(2-methyl-benzoyl)-thiazol-2-ylamino]-propyl}-amide | 360.4 MH+ |
| 33. | [2-(3-Amino-propylamino)-thiazol-5-yl]-(2-ethyl-phenyl)-methanone; hydrochloride and pentanoyl chloride | Pentanoic acid {3-[5-(2-ethyl-benzoyl)-thiazol-2-ylamino]-propyl}-amide | 374.5 MH+ |

-continued

| Ex. | Educts | Name | Mass analysis |
|---|---|---|---|
| 34. | [2-(3-Amino-propylamino)-thiazol-5-yl]-(2-fluoro-phenyl)-methanone; hydrochloride and pentanoyl chloride | Pentanoic acid {3-[5-(2-fluoro-benzoyl)-thiazol-2-ylamino]-propyl}-amide | 364.3 MH+ |
| 35. | [2-(3-Amino-propylamino)-thiazol-5-yl]-(2-chloro-phenyl)-methanone; hydrochloride and pentanoyl chloride | Pentanoic acid {3-[5-(2-chloro-benzoyl)-thiazol-2-ylamino]-propyl}-amide | 380.4 MH+ |
| 36. | [2-(3-Amino-propylamino)-thiazol-5-yl]-phenyl-methanone; hydrochloride and 4-Chlorophenylacetyl chloride | N-[3-(5-Benzoyl-thiazol-2-ylamino)-propyl]-2-(4-chloro-phenyl)-acetamide | 414.35 MH+ |
| 37. | [2-(3-Amino-propylamino)-thiazol-5-yl]-o-tolyl-methanone; hydrochloride and 4-Chlorophenylacetyl chloride | 2-(4-Chloro-phenyl)-N-{3-[5-(2-methyl-benzoyl)-thiazol-2-ylamino]-propyl}-acetamide | 428.5 MH+ |
| 38. | [2-(3-Amino-propylamino)-thiazol-5-yl]-(2-ethyl-phenyl)-methanone; hydrochloride and 4-Chlorophenylacetyl chloride | 2-(4-Chloro-phenyl)-N-{3-[5-(2-ethyl-benzoyl)-thiazol-2-ylamino]-propyl}-acetamide | 442.4 MH+ |
| 39. | [2-(3-Amino-propylamino)-thiazol-5-yl]-o-tolyl-methanone; hydrochloride and thiophene-2-carbonyl chloride | Thiophene-2-carboxylic acid {3-[5-(2-methyl-benzoyl)-thiazol-2-ylamino]-propyl}-amide | 386.3 MH+ |
| 40. | [2-(3-Amino-propylamino)-thiazol-5-yl]-(2-ethyl-phenyl)-methanone; hydrochloride and thiophene-2-carbonyl chloride | Thiophene-2-carboxylic acid {3-[5-(2-ethyl-benzoyl)-thiazol-2-ylamino]-propyl}-amide | 400.5 MH+ |
| 41. | [2-(3-Amino-propylamino)-thiazol-5-yl]-(2-fluoro-phenyl)-methanone; hydrochloride and thiophene-2-carbonyl chloride | Thiophene-2-carboxylic acid {3-[5-(2-fluoro-benzoyl)-thiazol-2-ylamino]-propyl}-amide | 390.2 MH+ |
| 42. | [2-(3-Amino-propylamino)-thiazol-5-yl]-(2-chloro-phenyl)-methanone; hydrochloride and thiophene-2-carbonyl chloride | Thiophene-2-carboxylic acid {3-[5-(2-chloro-benzoyl)-thiazol-2-ylamino]-propyl}-amide | 406.4 MH+ |
| 43. | [2-(3-Amino-propylamino)-thiazol-5-yl]-(2-ethyl-phenyl)-methanone; hydrochloride and 2-Fluorobenzoyl chloride | N-{3-[5-(2-Ethyl-benzoyl)-thiazol-2-ylamino]-propyl}-2-fluoro-benzamide | 412.4 MH+ |
| 44. | [2-(3-Amino-propylamino)-thiazol-5-yl]-(2-chloro-phenyl)-methanone; hydrochloride and 2-Fluorobenzoyl chloride | N-{3-[5-(2-Chloro-benzoyl)-thiazol-2-ylamino]-propyl}-2-fluoro-benzamide | 418.3 MH+ |
| 45. | [2-(3-Amino-propylamino)-thiazol-5-yl]-o-tolyl-methanone; hydrochloride and 3-Fluorobenzoyl chloride | 3-Fluoro-N-{3-[5-(2-methyl-benzoyl)-thiazol-2-ylamino]-propyl}-benzamide | 398.4 MH+ |
| 46. | [2-(3-Amino-propylamino)-thiazol-5-yl]-(2-ethyl-phenyl)-methanone; hydrochloride and 3-Fluorobenzoyl chloride | N-{3-[5-(2-Ethyl-benzoyl)-thiazol-2-ylamino]-propyl}-3-fluoro-benzamide | 412.4 MH+ |
| 47. | [2-(3-Amino-propylamino)-thiazol-5-yl]-(2-fluoro-phenyl)-methanone; hydrochloride and 3-Fluorobenzoyl chloride | 3-Fluoro-N-{3-[5-(2-fluoro-benzoyl)-thiazol-2-ylamino]-propyl}-benzamide | 402.5 MH+ |
| 48. | [2-(3-Amino-propylamino)-thiazol-5-yl]-(2-chloro-phenyl)-methanone; hydrochloride and 3-Fluorobenzoyl chloride | N-{3-[5-(2-Chloro-benzoyl)-thiazol-2-ylamino]-propyl}-3-fluoro-benzamide | 418.3 MH+ |
| 49. | [2-(3-Amino-propylamino)-thiazol-5-yl]-o-tolyl-methanone; hydrochloride and 4-Fluorobenzoyl chloride | 4-Fluoro-N-{3-[5-(2-methyl-benzoyl)-thiazol-2-ylamino]-propyl}-benzamide | 398.4 MH+ |
| 50. | [2-(3-Amino-propylamino)-thiazol-5-yl]-(2-ethyl-phenyl)-methanone; hydrochloride and 4-Fluorobenzoyl chloride | N-{3-[5-(2-Ethyl-benzoyl)-thiazol-2-ylamino]-propyl}-4-fluoro-benzamide | 412.4 MH+ |
| 51. | [2-(3-Amino-propylamino)-thiazol-5-yl]-(2-chloro-phenyl)-methanone; hydrochloride and 4-Fluorobenzoyl chloride | N-{3-[5-(2-Chloro-benzoyl)-thiazol-2-ylamino]-propyl}-4-fluoro-benzamide | 418.3 MH+ |
| 52. | [2-(3-Amino-propylamino)-thiazol-5-yl]-o-tolyl-methanone; hydrochloride and benzoyl chloride | N-{3-[5-(2-Methyl-benzoyl)-thiazol-2-ylamino]-propyl}-benzamide | 380.4 MH+ |
| 53. | [2-(3-Amino-propylamino)-thiazol-5-yl]-(2-ethyl-phenyl)-methanone; hydrochloride and benzoyl chloride | N-{3-[5-(2-Ethyl-benzoyl)-thiazol-2-ylamino]-propyl}-benzamide | 394.4 MH+ |
| 54. | [2-(3-Amino-propylamino)-thiazol-5-yl]-(2-chloro-phenyl)-methanone; hydrochloride and benzoyl chloride | N-{3-[5-(2-Chloro-benzoyl)-thiazol-2-ylamino]-propyl}-benzamide | 400.4 MH+ |
| 55. | [2-(3-Amino-propylamino)-thiazol-5-yl]-(2-ethyl-phenyl)-methanone; hydrochloride and 4-methoxybenzoyl chloride | N-{3-[5-(2-Ethyl-benzoyl)-thiazol-2-ylamino]-propyl}-4-methoxy-benzamide | 424.5 MH+ |
| 56. | [2-(3-Amino-propylamino)-thiazol-5-yl]-phenyl-methanone; hydrochloride and 2-methoxybenzoyl chloride | N-[3-(5-Benzoyl-thiazol-2-ylamino)-propyl]-2-methoxy-benzamide | 396.3 MH+ |
| 57. | [2-(3-Amino-propylamino)-thiazol-5-yl]-(2-ethyl-phenyl)-methanone; hydrochloride and 2-methoxybenzoyl chloride | N-{3-[5-(2-Ethyl-benzoyl)-thiazol-2-ylamino]-propyl}-2-methoxy-benzamide | 424.5 MH+ |
| 58. | [2-(3-Amino-propylamino)-thiazol-5-yl]-o-tolyl-methanone; hydrochloride and 4-chlorobenzoyl chloride | 4-Chloro-N-{3-[5-(2-methyl-benzoyl)-thiazol-2-ylamino]-propyl}-benzamide | 414.3 MH+ |
| 59. | [2-(3-Amino-propylamino)-thiazol-5-yl]-(2-ethyl-phenyl)-methanone; hydrochloride 4-chlorobenzoyl chloride | 4-Chloro-N-{3-[5-(2-ethyl-benzoyl)-thiazol-2-ylamino]-propyl}-benzamide | 428.5 MH+ |
| 60. | [2-(3-Amino-propylamino)-thiazol-5-yl]-(2-trifluoromethyl-phenyl)-methanone; hydrochloride and cyclohexyanecarbonyl chloride | Cyclohexanecarboxylic acid {3-[5-(2-trifluoromethyl-benzoyl)-thiazol-2-ylamino]-propyl}-amide | 440.5 MH+ |
| 61. | [2-(3-Amino-propylamino)-thiazol-5-yl]-(4-methyl-pyridin-3-yl)-methanone; hydrochloride and cyclohexanecarbonyl chloride | Cyclohexanecarboxylic acid {3-[5-(4-methyl-pyridine-3-carbonyl)-thiazol-2-ylamino]-propyl}-amide | 387.4 MH+ |
| 62. | [2-(3-Amino-propylamino)-thiazol-5-yl]-(2-trifluoromethyl-phenyl)-methanone; hydrochloride and pentanoyl chloride | Pentanoic acid {3-[5-(2-trifluoromethyl-benzoyl)-thiazol-2-ylamino]-propyl}-amide | 414.4 MH+ |
| 63. | [2-(3-Amino-propylamino)-thiazol-5-yl]-(4-methyl-pyridin-3-yl)-methanone; hydrochloride and pentanoyl chloride | Pentanoic acid {3-[5-(4-methyl-pyridine-3-carbonyl)-thiazol-2-ylamino]-propyl}-amide | 361.3 MH+ |
| 64. | [2-(3-Amino-propylamino)-thiazol-5-yl]-(2-methyl-pyridin-3-yl)-methanone; hydrochloride and pentanoyl chloride | Pentanoic acid {3-[5-(2-methyl-pyridine-3-carbonyl)-thiazol-2-ylamino]-propyl}-amide | 361.3 MH+ |
| 65. | [2-(3-Amino-propylamino)-thiazol-5-yl]-(3-methyl-thiophen-2-yl)-methanone; hydrochloride and pentanoyl chloride | Pentanoic acid {3-[5-(3-methyl-thiophene-2-carbonyl)-thiazol-2-ylamino]-propyl}-amide | 366.3 MH+ |
| 66. | [2-(3-Amino-propylamino)-thiazol-5-yl]-(2-trifluoromethyl-phenyl)-methanone; hydrochloride and 4-Chlorophenylacetyl chloride | 2-(4-Chloro-phenyl)-N-{3-[5-(2-trifluoromethyl-benzoyl)-thiazol-2-ylamino]-propyl}-acetamide | 482.3 MH+ |
| 67. | 2-(3-Amino-propylamino)-thiazol-5-yl]-(3-methyl-pyridin-2-yl)-methanone; hydrochloride and 4-Chlorophenylacetyl chloride | 2-(4-Chloro-phenyl)-N-{3-[5-(3-methyl-pyridine-2-carbonyl)-thiazol-2-ylamino]-propyl}-acetamide | 429.5 MH+ |
| 68. | [2-(3-Amino-propylamino)-thiazol-5-yl]-(3-methyl-pyrazin-2-yl)-methanone; hydrochloride and 4-Chlorophenylacetyl chloride | 2-(4-Chloro-phenyl)-N-{3-[5-(3-methyl-pyrazine-2-carbonyl)-thiazol-2-ylamino]-propyl}-acetamide | 430.5 MH+ |

-continued

| Ex. | Educts | Name | Mass analysis |
|---|---|---|---|
| 69. | [2-(3-Amino-propylamino)-thiazol-5-yl]-(2-trifluoromethyl-phenyl)-methanone; hydrochloride and thiophene-2-carbonyl chloride | Thiophene-2-carboxylic acid {3-[5-(2-trifluoromethyl-benzoyl)-thiazol-2-ylamino]-propyl}-amide | 440.4 MH+ |
| 70. | 2-(3-Amino-propylamino)-thiazol-5-yl]-(3-methyl-pyridin-2-yl)-methanone; hydrochloride and thiophene-2-carbonyl chloride | Thiophene-2-carboxylic acid {3-[5-(3-methyl-pyridine-2-carbonyl)-thiazol-2-ylamino]-propyl}-amide | 387.3 MH+ |
| 71. | [2-(3-Amino-propylamino)-thiazol-5-yl]-(2-trifluoromethyl-phenyl)-methanone; hydrochloride and 2-Fluorobenzoyl chloride | 2-Fluoro-N-{3-[5-(2-trifluoromethyl-benzoyl)-thiazol-2-ylamino]-propyl}-benzamide | 452.4 MH+ |
| 72. | [2-(3-Amino-propylamino)-thiazol-5-yl]-(3-methyl-pyrazin-2-yl)-methanone; hydrochloride and 2-Fluorobenzoyl chloride | 2-Fluoro-N-{3-[5-(3-methyl-pyrazine-2-carbonyl)-thiazol-2-ylamino]-propyl}-benzamide | 400.4 MH+ |
| 73. | [2-(3-Amino-propylamino)-thiazol-5-yl]-(2-trifluoromethyl-phenyl)-methanone; hydrochloride and 3-Fluorobenzoyl chloride | 3-Fluoro-N-{3-[5-(2-trifluoromethyl-benzoyl)-thiazol-2-ylamino]-propyl}-benzamide | 452.4 MH+ |
| 74. | [2-(3-Amino-propylamino)-thiazol-5-yl]-(4-methyl-pyridin-3-yl)-methanone; hydrochloride and 3-Fluorobenzoyl chloride | 3-Fluoro-N-{3-[5-(4-methyl-pyridine-3-carbonyl)-thiazol-2-ylamino]-propyl}-benzamide | 399.4 MH+ |
| 75. | 2-(3-Amino-propylamino)-thiazol-5-yl]-(3-methyl-pyridin-2-yl)-methanone; hydrochloride and 3-Fluorobenzoyl chloride | 3-Fluoro-N-{3-[5-(3-methyl-pyridine-2-carbonyl)-thiazol-2-ylamino]-propyl}-benzamide | 399.4 MH+ |
| 76. | [2-(3-Amino-propylamino)-thiazol-5-yl]-(3-methyl-pyrazin-2-yl)-methanone; hydrochloride and 3-Fluorobenzoyl chloride | 3-Fluoro-N-{3-[5-(3-methyl-pyrazine-2-carbonyl)-thiazol-2-ylamino]-propyl}-benzamide | 400.4 MH+ |
| 77. | [2-(3-Amino-propylamino)-thiazol-5-yl]-(2-trifluoromethyl-phenyl)-methanone; hydrochloride and 4-Fluorobenzoyl chloride | 4-Fluoro-N-{3-[5-(2-trifluoromethyl-benzoyl)-thiazol-2-ylamino]-propyl}-benzamide | 452.4 MH+ |
| 78. | [2-(3-Amino-propylamino)-thiazol-5-yl]-(4-methyl-pyridin-3-yl)-methanone; hydrochloride and 4-Fluorobenzoyl chloride | 4-Fluoro-N-{3-[5-(4-methyl-pyridine-3-carbonyl)-thiazol-2-ylamino]-propyl}-benzamide | 399.4 MH+ |
| 79. | 2-(3-Amino-propylamino)-thiazol-5-yl]-(3-methyl-pyridin-2-yl)-methanone; hydrochloride and 4-Fluorobenzoyl chloride | 4-Fluoro-N-{3-[5-(3-methyl-pyridine-2-carbonyl)-thiazol-2-ylamino]-propyl}-benzamide | 399.4 MH+ |
| 80. | [2-(3-Amino-propylamino)-thiazol-5-yl]-(3-methyl-thiophen-2-yl)-methanone; hydrochloride 3-methyl-2-thiophenecarbonyl chloride | 4-Fluoro-N-{3-[5-(3-methyl-thiophene-2-carbonyl)-thiazol-2-ylamino]-propyl}-benzamide | 404.4 MH+ |
| 81. | [2-(3-Amino-propylamino)-thiazol-5-yl]-(2-trifluoromethyl-phenyl)-methanone; hydrochloride and benzoyl chloride | N-{3-[5-(2-Trifluoromethyl-benzoyl)-thiazol-2-ylamino]-propyl}-benzamide | 434.5 MH+ |
| 82. | [2-(3-Amino-propylamino)-thiazol-5-yl]-(4-methyl-pyridin-3-yl)-methanone; hydrochloride and benzoyl chloride | N-{3-[5-(4-Methyl-pyridine-3-carbonyl)-thiazol-2-ylamino]-propyl}-benzamide | 381.4 MH+ |
| 83. | [2-(3-Amino-propylamino)-thiazol-5-yl]-(2-trifluoromethyl-phenyl)-methanone; hydrochloride and 4-Methoxybenzoyl chloride | 4-Methoxy-N-{3-[5-(2-trifluoromethyl-benzoyl)-thiazol-2-ylamino]-propyl}-benzamide | 464.3 MH+ |
| 84. | [2-(3-Amino-propylamino)-thiazol-5-yl]-(4-methyl-pyridin-3-yl)-methanone; hydrochloride and 4-Methoxybenzoyl chloride | 4-Methoxy-N-{3-[5-(4-methyl-pyridine-3-carbonyl)-thiazol-2-ylamino]-propyl}-benzamide | 411.4 MH+ |
| 85. | [2-(3-Amino-propylamino)-thiazol-5-yl]-(2-trifluoromethyl-phenyl)-methanone; hydrochloride and 2-Methoxybenzoyl chloride | 2-Methoxy-N-{3-[5-(2-trifluoromethyl-benzoyl)-thiazol-2-ylamino]-propyl}-benzamide | 464.3 MH+ |
| 86. | [2-(3-Amino-propylamino)-thiazol-5-yl]-(2-trifluoromethyl-phenyl)-methanone; hydrochloride and 4-Chlorobenzoyl chloride | 4-Chloro-N-{3-[5-(2-trifluoromethyl-benzoyl)-thiazol-2-ylamino]-propyl}-benzamide | 468.2 MH+ |
| 87. | [2-(3-Amino-propylamino)-thiazol-5-yl]-(4-methyl-pyridin-3-yl)-methanone; hydrochloride and 4-Chlorobenzoyl chloride | 4-Chloro-N-{3-[5-(4-methyl-pyridine-3-carbonyl)-thiazol-2-ylamino]-propyl}-benzamide | 415.3 MH+ |
| 88. | [2-(3-Amino-propylamino)-thiazol-5-yl]-(2-methyl-pyridin-3-yl)-methanone; hydrochloride and 4-Chlorobenzoyl chloride | 4-Chloro-N-{3-[5-(2-methyl-pyridine-3-carbonyl)-thiazol-2-ylamino]-propyl}-benzamide | 415.3 MH+ |
| 89. | [2-(3-Amino-propylamino)-thiazol-5-yl]-phenyl-methanone; hydrochloride and cyclohexyl isocyanate | 1-[3-(5-Benzoyl-thiazol-2-ylamino)-propyl]-3-cyclohexyl-urea | 386.5 MH+ |
| 90. | [2-(3-Amino-propylamino)-thiazol-5-yl]-o-tolyl-methanone; hydrochloride and cyclohexyl isocyanate | 1-Cyclohexyl-3-{3-[5-(2-methyl-benzoyl)-thiazol-2-ylamino]-propyl}-urea | 400.5 MH+ |
| 91. | [2-(3-Amino-propylamino)-thiazol-5-yl]-(2-ethyl-phenyl)-methanone; hydrochloride and cyclohexyl isocyanate | 1-Cyclohexyl-3-{3-[5-(2-ethyl-benzoyl)-thiazol-2-ylamino]-propyl}-urea | 414.5 MH+ |
| 92. | [2-(3-Amino-propylamino)-thiazol-5-yl]-(2-chloro-phenyl)-methanone; hydrochloride and cyclohexyl isocyanate | 1-{3-[5-(2-Chloro-benzoyl)-thiazol-2-ylamino]-propyl}-3-cyclohexyl-urea | 420.9 MH+ |
| 93. | [2-(3-Amino-propylamino)-thiazol-5-yl]-phenyl-methanone; hydrochloride and n-butyl isocyanante | 1-[3-(5-Benzoyl-thiazol-2-ylamino)-propyl]-3-butyl-urea | 360.4 MH+ |
| 94. | [2-(3-Amino-propylamino)-thiazol-5-yl]-o-tolyl-methanone; hydrochloride and n-butyl isocyanante | 1-Butyl-3-{3-[5-(2-methyl-benzoyl)-thiazol-2-ylamino]-propyl}-urea | 374.5 MH+ |
| 95. | [2-(3-Amino-propylamino)-thiazol-5-yl]-(2-ethyl-phenyl)-methanone; hydrochloride and n-butyl isocyanante | 1-Butyl-3-{3-[5-(2-ethyl-benzoyl)-thiazol-2-ylamino]-propyl}-urea | 388.5 MH+ |
| 96. | [2-(3-Amino-propylamino)-thiazol-5-yl]-(2-fluoro-phenyl)-methanone; hydrochloride and n-butyl isocyanante | 1-Butyl-3-{3-[5-(2-fluoro-benzoyl)-thiazol-2-ylamino]-propyl}-urea | 378.4 MH+ |
| 97. | [2-(3-Amino-propylamino)-thiazol-5-yl]-(2-chloro-phenyl)-methanone; hydrochloride and n-butyl isocyanante | 1-Butyl-3-{3-[5-(2-chloro-benzoyl)-thiazol-2-ylamino]-propyl}-urea | 394.9 MH+ |
| 98. | [2-(3-Amino-propylamino)-thiazol-5-yl]-o-tolyl-methanone; hydrochloride and 2-Methoxyphenyl isocyanate | 1-(2-Methoxy-phenyl)-3-{3-[5-(2-methyl-benzoyl)-thiazol-2-ylamino]-propyl}-urea | 424.5 MH+ |
| 99. | [2-(3-Amino-propylamino)-thiazol-5-yl]-(2-ethyl-phenyl)-methanone; hydrochloride and 2-Methoxyphenyl isocyanate | 1-{3-[5-(2-Ethyl-benzoyl)-thiazol-2-ylamino]-propyl}-3-(2-methoxy-phenyl)-urea | 438.5 MH+ |
| 100. | [2-(3-Amino-propylamino)-thiazol-5-yl]-(2-chloro-phenyl)-methanone; hydrochloride and 2-Methoxyphenyl isocyanate | 1-{3-[5-(2-Chloro-benzoyl)-thiazol-2-ylamino]-propyl}-3-(2-methoxy-phenyl)-urea | 444.9 MH+ |
| 101. | [2-(3-Amino-propylamino)-thiazol-5-yl]-o-tolyl-methanone; hydrochloride and 2-Fluorophenyl isocyanate | 1-(2-Fluoro-phenyl)-3-{3-[5-(2-methyl-benzoyl)-thiazol-2-ylamino]-propyl}-urea | 412.4 MH+ |
| 102. | [2-(3-Amino-propylamino)-thiazol-5-yl]-(2-ethyl-phenyl)-methanone; hydrochloride and 2-Fluorophenyl isocyanate | 1-{3-[5-(2-Ethyl-benzoyl)-thiazol-2-ylamino]-propyl}-3-(2-fluoro-phenyl)-urea | 426.5 MH+ |

-continued

| Ex. | Educts | Name | Mass analysis |
|---|---|---|---|
| 103. | [2-(3-Amino-propylamino)-thiazol-5-yl]-(2-chloro-phenyl)-methanone; hydrochloride and 2-Fluorophenyl isocyanate | 1-{3-[5-(2-Chloro-benzoyl)-thiazol-2-ylamino]-propyl}-3-(2-fluoro-phenyl)-urea | 432.9 MH+ |
| 104. | [2-(3-Amino-propylamino)-thiazol-5-yl]-o-tolyl-methanone; hydrochloride and 3-Fluorophenyl isocyanate | 1-(3-Fluoro-phenyl)-3-{3-[5-(2-methyl-benzoyl)-thiazol-2-ylamino]-propyl}-urea | 412.4 MH+ |
| 105. | [2-(3-Amino-propylamino)-thiazol-5-yl]-(2-ethyl-phenyl)-methanone; hydrochloride and 3-Fluorophenyl isocyanate | 1-{3-[5-(2-Ethyl-benzoyl)-thiazol-2-ylamino]-propyl}-3-(3-fluoro-phenyl)-urea | 426.5 MH+ |
| 106. | [2-(3-Amino-propylamino)-thiazol-5-yl]-o-tolyl-methanone; hydrochloride and 4-Fluorophenyl isocyanate | 1-(4-Fluoro-phenyl)-3-{3-[5-(2-methyl-benzoyl)-thiazol-2-ylamino]-propyl}-urea | 412.4 MH+ |
| 107. | [2-(3-Amino-propylamino)-thiazol-5-yl]-(2-ethyl-phenyl)-methanone; hydrochloride and 4-Fluorophenyl isocyanate | 1-{3-[5-(2-Ethyl-benzoyl)-thiazol-2-ylamino]-propyl}-3-(4-fluoro-phenyl)-urea | 426.5 MH+ |
| 108. | [2-(3-Amino-propylamino)-thiazol-5-yl]-phenyl-methanone; hydrochloride and 4-Chlorobenzyl isocyanate (WO0107436) | 1-[3-(5-Benzoyl-thiazol-2-ylamino)-propyl]-3-(2-chloro-benzyl)-urea | 428.9 MH+ |
| 109. | [2-(3-Amino-propylamino)-thiazol-5-yl]-o-tolyl-methanone; hydrochloride and 4-Chlorobenzyl isocyanate (WO0107436) | 1-(2-Chloro-benzyl)-3-{3-[5-(2-methyl-benzoyl)-thiazol-2-ylamino]-propyl}-urea | 442.9 MH+ |
| 110. | [2-(3-Amino-propylamino)-thiazol-5-yl]-(2-ethyl-phenyl)-methanone; hydrochloride and 4-Chlorobenzyl isocyanate (WO0107436) | 1-(2-Chloro-benzyl)-3-{3-[5-(2-ethyl-benzoyl)-thiazol-2-ylamino]-propyl}-urea | 457.0 MH+ |
| 111. | [2-(3-Amino-propylamino)-thiazol-5-yl]-(2-chloro-phenyl)-methanone; hydrochloride and 4-Chlorobenzyl isocyanate (WO0107436) | 1-{3-[5-(2-Chloro-benzoyl)-thiazol-2-ylamino]-propyl}-3-(2-chloro-benzyl)-urea | 463.3 MH+ |
| 112. | [2-(3-Amino-propylamino)-thiazol-5-yl]-o-tolyl-methanone; hydrochloride and phenyl isocyanate | 1-{3-[5-(2-Methyl-benzoyl)-thiazol-2-ylamino]-propyl}-3-phenyl-urea | 394.5 MH+ |
| 113. | [2-(3-Amino-propylamino)-thiazol-5-yl]-(2-ethyl-phenyl)-methanone; hydrochloride and phenyl isocyanate | 1-{3-[5-(2-Ethyl-benzoyl)-thiazol-2-ylamino]-propyl}-3-phenyl-urea | 408.5 MH+ |
| 114. | [2-(3-Amino-propylamino)-thiazol-5-yl]-(2-chloro-phenyl)-methanone; hydrochloride and phenyl isocyanate | 1-{3-[5-(2-Chloro-benzoyl)-thiazol-2-ylamino]-propyl}-3-phenyl-urea | 414.9 MH+ |
| 115. | [2-(3-Amino-propylamino)-thiazol-5-yl]-(4-methyl-pyridin-3-yl)-methanone; hydrochloride and n-butyl isocyanate | 1-Butyl-3-{3-[5-(4-methyl-pyridine-3-carbonyl)-thiazol-2-ylamino]-propyl}-urea | 375.5 MH+ |
| 116. | [2-(3-Amino-propylamino)-thiazol-5-yl]-(4-methyl-pyridin-3-yl)-methanone; hydrochloride and phenyl isocyanate | 1-{3-[5-(4-Methyl-pyridine-3-carbonyl)-thiazol-2-ylamino]-propyl}-3-phenyl-urea | 395.5 MH+ |
| 117. | [2-(3-Amino-propylamino)-thiazol-5-yl]-(3-methyl-pyrazin-2-yl)-methanone; hydrochloride and cyclohexyl isocyanate | 1-Cyclohexyl-3-{3-[5-(3-methyl-pyrazine-2-carbonyl)-thiazol-2-ylamino]-propyl}-urea | 402.5 MH+ |
| 118. | [2-(3-Amino-propylamino)-thiazol-5-yl]-(3-methyl-thiophen-2-yl)-methanone; hydrochloride and cyclohexyl isocyanate | 1-Cyclohexyl-3-{3-[5-(3-methyl-thiophene-2-carbonyl)-thiazol-2-ylamino]-propyl}-urea | 406.6 MH+ |
| 119. | [2-(3-Amino-propylamino)-thiazol-5-yl]-(4-methyl-pyridin-3-yl)-methanone; hydrochloride and 4-Fluorophenylsulfonyl chloride | 4-Fluoro-N-{3-[5-(4-methyl-pyridine-3-carbonyl)-thiazol-2-ylamino]-propyl}-benzenesulfonamide | 434.5 MH+ |
| 120. | [2-(3-Amino-propylamino)-thiazol-5-yl]-(3-methyl-thiophen-2-yl)-methanone; hydrochloride and 4-Fluorophenylsulfonyl chloride | 4-Fluoro-N-{3-[5-(3-methyl-thiophene-2-carbonyl)-thiazol-2-ylamino]-propyl}-benzenesulfonamide | 439.6 MH+ |
| 121. | [2-(3-Amino-propylamino)-thiazol-5-yl]-(4-methyl-pyridin-3-yl)-methanone; hydrochloride and 2-Methoxy-5-methyl-phenylsulfonyl chloride | 2-Methoxy-5-methyl-N-{3-[5-(4-methyl-pyridine-3-carbonyl)-thiazol-2-ylamino]-propyl}-benzenesulfonamide | 460.6 MH+ |
| 122. | [2-(3-Amino-propylamino)-thiazol-5-yl]-(3-methyl-pyrazin-2-yl)-methanone; hydrochloride and 2-Methoxy-5-methyl-phenylsulfonyl chloride | 2-Methoxy-5-methyl-N-{3-[5-(3-methyl-pyrazine-2-carbonyl)-thiazol-2-ylamino]-propyl}-benzenesulfonamide | 461.6 MH+ |
| 123. | [2-(3-Amino-propylamino)-thiazol-5-yl]-(3-methyl-thiophen-2-yl)-methanone; hydrochloride and 2-Methoxy-5-methyl-phenylsulfonyl chloride | 2-Methoxy-5-methyl-N-{3-[5-(3-methyl-thiophene-2-carbonyl)-thiazol-2-ylamino]-propyl}-benzenesulfonamide | 465.6 MH+ |
| 124. | [2-(3-Amino-propylamino)-thiazol-5-yl]-(4-methyl-pyridin-3-yl)-methanone; hydrochloride and 4-Methoxyphenylsulfonyl chloride | 1-(4-Methoxy-phenyl)-3-{3-[5-(4-methyl-pyridine-3-carbonyl)-thiazol-2-ylamino]-propyl}-urea | 425.5 MH+ |
| 125. | 3-Bromo-1-o-tolyl-propane-1,2-dione and (3-thioureido-propyl) carbamic acid tert-butyl ester | {3-[4-(2-Methyl-benzoyl)-thiazol-2-ylamino]-propyl}-carbamic acid tert-butyl ester | 376.5 MH+ |
| 126. | [2-(3-Amino-propylamino)-thiazol-4-yl]-o-tolyl-methanone; hydrochloride and benzoyl chloride | N-{3-[4-(2-methyl-benzoyl)-thiazol-2-ylamino]-propyl}-benzamide | 380.4 MH+ |
| 127. | [2-(3-Amino-propylamino)-thiazol-4-yl]-o-tolyl-methanone; hydrochloride and 2-Fluorobenzoyl chloride | 2-Fluoro-N-{3-[4-(2-methyl-benzoyl)-thiazol-2-ylamino]-propyl}-benzamide | 398.4 MH+ |
| 128. | [2-(3-Amino-propylamino)-thiazol-4-yl]-o-tolyl-methanone; hydrochloride and 3,5-dimethoxybenzoyl chloride | 3,5-Dimethoxy-N-{3-[4-(2-methyl-benzoyl)-thiazol-2-ylamino]-propyl}-benzamide | 440.5 MH+ |
| 129. | [2-(3-Amino-propylamino)-thiazol-4-yl]-o-tolyl-methanone; hydrochloride and pentanoyl chloride | Pentanoic acid {3-[4-(2-methyl-benzoyl)-thiazol-2-ylamino]-propyl}-amide | 360.3 MH+ |
| 130. | [2-(3-Amino-propylamino)-thiazol-4-yl]-o-tolyl-methanone; hydrochloride and 2-thiophene isocyanate | 1-{3-[4-(2-Methyl-benzoyl)-thiazol-2-ylamino]-propyl}-3-thiophen-2-yl-urea | 401.5 MH+ |
| 131. | [2-(3-Amino-propylamino)-thiazol-4-yl]-o-tolyl-methanone; hydrochloride and 2-fluorophenyl isocyanate | 1-(2-Fluoro-phenyl)-3-{3-[4-(2-methyl-benzoyl)-thiazol-2-ylamino]-propyl}-urea | 413.3 MH+ |
| 132. | [2-(3-Amino-propylamino)-thiazol-4-yl]-o-tolyl-methanone; hydrochloride and 2-methylbenzenesulfonyl chloride | 2-Methyl-N-{3-[4-(2-methyl-benzoyl)-thiazol-2-ylamino]-propyl}-benzenesulfonamide | 430.5 MH+ |
| 133. | [2-(3-Amino-propylamino)-thiazol-4-yl]-o-tolyl-methanone; hydrochloride and 4-fluorobenzenesulfonyl chloride | 4-Fluoro-N-{3-[4-(2-methyl-benzoyl)-thiazol-2-ylamino]-propyl}-benzenesulfonamide | 434.4 MH+ |
| 134. | [2-(3-Amino-propylamino)-thiazol-4-yl]-o-tolyl-methanone; hydrochloride and 3-methoxybenzenesulfonyl chloride | 3-Methoxy-N-{3-[4-(2-methyl-benzoyl)-thiazol-2-ylamino]-propyl}-benzenesulfonamide | 446.3 MH+ |
| 135. | [2-(3-Amino-propylamino)-thiazol-4-yl]-o-tolyl-methanone; hydrochloride and 3-methoxybenzenesulfonyl chloride | 4-Methoxy-N-{3-[4-(2-methyl-benzoyl)-thiazol-2-ylamino]-propyl}-benzenesulfonamide | 446.3 MH+ |
| 136. | [2-(3-Amino-propylamino)-thiazol-4-yl]-o-tolyl-methanone; hydrochloride and benzenesulfonyl chloride | N-{3-[4-(2-Methyl-benzoyl)-thiazol-2-ylamino]-propyl}-benzenesulfonamide | 416.3 MH+ |

-continued

| Ex. | Educts | Name | Mass analysis |
|---|---|---|---|
| 137. | [2-(3-Amino-propylamino)-thiazol-4-yl]-o-tolyl-methanone; hydrochloride and 2-chloro-5-(trifluormethyl)benzenesulfonyl chloride | 2-Chloro-N-{3-[4-(2-methyl-benzoyl)-thiazol-2-ylamino]-propyl}-5-trifluoromethyl-benzenesulfonamide | 518.1 MH+ |
| 138. | [2-(3-Amino-propylamino)-thiazol-4-yl]-o-tolyl-methanone; hydrochloride and 2-thiophenesulfonyl chloride | Thiophene-2-sulfonic acid {3-[4-(2-methyl-benzoyl)-thiazol-2-ylamino]-propyl}-amide | 422.3 MH+ |
| 139. | [2-(3-Amino-propylamino)-thiazol-4-yl]-o-tolyl-methanone; hydrochloride and 3-fluorobenzenesulfonyl chloride | 3-Fluoro-N-{3-[4-(2-methyl-benzoyl)-thiazol-2-ylamino]-propyl}-benzenesulfonamide | 434.4 MH+ |
| 140. | [2-(3-Amino-propylamino)-thiazol-4-yl]-o-tolyl-methanone; hydrochloride and 6-methoxy-m-toluenesulfonyl chloride | 2-Methoxy-5-methyl-N-{3-[4-(2-methyl-benzoyl)-thiazol-2-ylamino]-propyl}-benzenesulfonamide | 460.5 MH+ |
| 141. | [2-(3-Amino-propylamino)-thiazol-4-yl]-o-tolyl-methanone; hydrochloride and 2,5-dimethoxybenzenesulfonyl chloride | 2,5-Dimethoxy-N-{3-[4-(2-methyl-benzoyl)-thiazol-2-ylamino]-propyl}-benzenesulfonamide | 476.2 MH+ |
| 142. | [2-(5-Amino-pentylamino)-thiazol-5-yl]-pyridin-2-yl-methanone; hydrochloride and 2-fluorobenzenesulfonyl chloride | 2-Fluoro-N-{5-[5-(pyridine-2-carbonyl)-thiazol-2-ylamino]-pentyl}-benzenesulfonamide | 447.2 (M − H+)− |
| 143. | [2-(5-Amino-pentylamino)-thiazol-5-yl]-pyridin-2-yl-methanone; hydrochloride and benzenesulfonyl chloride | 4-Methoxy-N-{5-[5-(pyridine-2-carbonyl)-thiazol-2-ylamino]-pentyl}-benzenesulfonamide | 459.3 (M − H+)− |
| 144. | [2-(5-Amino-pentylamino)-thiazol-5-yl]-pyridin-2-yl-methanone; hydrochloride and 2-thiophenesulfonyl chloride | Thiophene-2-sulfonic acid {5-[5-(pyridine-2-carbonyl)-thiazol-2-ylamino]-pentyl}-amide | 435.3 (M − H+)− |
| 145. | [2-(5-Amino-pentylamino)-thiazol-5-yl]-pyridin-2-yl-methanone; hydrochloride and 6-methoxy-m-toluenesulfonyl chloride | 2-Methoxy-5-methyl-N-{5-[5-(pyridine-2-carbonyl)-thiazol-2-ylamino]-pentyl}-benzenesulfonamide | 473.2 (M − H+)− |
| 146. | [2-(5-Amino-pentylamino)-thiazol-5-yl]-pyridin-2-yl-methanone; hydrochloride and 4-fluorobenzenesulfonyl chloride | 4-Fluoro-N-{5-[5-(pyridine-2-carbonyl)-thiazol-2-ylamino]-pentyl}-benzenesulfonamide | 447.3 (M − H+)− |
| 147. | [2-(5-Amino-pentylamino)-thiazol-5-yl]-pyridin-2-yl-methanone; hydrochloride and 2-methylbenzenesulfonyl chloride | 2-Methyl-N-{5-[5-(pyridine-2-carbonyl)-thiazol-2-ylamino]-pentyl}-benzenesulfonamide | 443.3 (M − H+)− |
| 148. | [2-(5-Amino-pentylamino)-thiazol-5-yl]-pyridin-2-yl-methanone; hydrochloride and 3-fluorobenzenesulfonyl chloride | 3-Fluoro-N-{5-[5-(pyridine-2-carbonyl)-thiazol-2-ylamino]-pentyl}-benzenesulfonamide | 447.2 (M − H+)− |
| 149. | [2-(5-Amino-pentylamino)-thiazol-5-yl]-pyridin-2-yl-methanone; hydrochloride and 2-chloro-5-(trifluoromethyl)-benzenesulfonyl chloride | 2-Chloro-N-{5-[5-(pyridine-2-carbonyl)-thiazol-2-ylamino]-pentyl}-5-trifluoro-methyl-benzenesulfonamide | 531.1 (M − H+)− |
| 150. | [2-(5-Amino-pentylamino)-thiazol-5-yl]-pyridin-2-yl-methanone; hydrochloride and benzenesulfonyl chloride | N-{5-[5-(Pyridine-2-carbonyl)-thiazol-2-ylamino]-pentyl}-benzenesulfonamide | 429.4 (M − H+)− |
| 151. | [2-(5-Amino-pentylamino)-thiazol-5-yl]-pyridin-2-yl-methanone; hydrochloride and 3-methoxybenzenesulfonyl chloride | 3-Methoxy-N-{5-[5-(pyridine-2-carbonyl)-thiazol-2-ylamino]-pentyl}-benzenesulfonamide | 459.3 (M − H+)− |
| 152. | [2-(5-Amino-pentylamino)-thiazol-5-yl]-pyridin-4-yl-methanone; hydrochloride and 2-fluorobenzenesulfonyl chloride | 2-Fluoro-N-{5-[5-(pyridine-4-carbonyl)-thiazol-2-ylamino]-pentyl}-benzenesulfonamide | 447.2 (M − H+)− |
| 153. | [2-(5-Amino-pentylamino)-thiazol-5-yl]-pyridin-4-yl-methanone; hydrochloride and 6-methoxy-m-toluenesulfonyl chloride | 2-Methoxy-5-methyl-N-{5-[5-(pyridine-4-carbonyl)-thiazol-2-ylamino]-pentyl}-benzenesulfonamide | 473.1 (M − H+)− |
| 154. | [2-(5-Amino-pentylamino)-thiazol-5-yl]-o-tolyl-methanone; hydrochloride and 2-fluorobenzenesulfonyl chloride | 2-Fluoro-N-{5-[5-(2-methyl-benzoyl)-thiazol-2-ylamino]-pentyl}-benzenesulfonamide | 460.4 (M − H+)− |
| 155. | [2-(5-Amino-pentylamino)-thiazol-5-yl]-o-tolyl-methanone; hydrochloride and 4-methoxybenzenesulfonyl chloride | 4-Methoxy-N-{5-[5-(2-methyl-benzoyl)-thiazol-2-ylamino]-pentyl}-benzenesulfonamide | 472.1 (M − H+)− |
| 156. | [2-(5-Amino-pentylamino)-thiazol-5-yl]-o-tolyl-methanone; hydrochloride and 2-thiophenesulfonyl chloride | Thiophene-2-sulfonic acid {5-[5-(2-methyl-benzoyl)-thiazol-2-ylamino]-pentyl}-amide | 448.2 (M − H+)− |
| 157. | [2-(5-Amino-pentylamino)-thiazol-5-yl]-o-tolyl-methanone; hydrochloride and 6-methoxy-m-toluenesulfonyl chloride | 2-Methoxy-5-methyl-N-{5-[5-(2-methyl-benzoyl)-thiazol-2-ylamino]-pentyl}-benzenesulfonamide | 486.3 (M − H+)− |
| 158. | [2-(5-Amino-pentylamino)-thiazol-5-yl]-o-tolyl-methanone; hydrochloride and 4-fluorobenzenesulfonyl chloride | 4-Fluoro-N-{5-[5-(2-methyl-benzoyl)-thiazol-2-ylamino]-pentyl}-benzenesulfonamide | 460.4 (M − H+)− |
| 159. | [2-(5-Amino-pentylamino)-thiazol-5-yl]-o-tolyl-methanone; hydrochloride and 2-methylbenzenesulfonyl chloride | 2-Methyl-N-{5-[5-(2-methyl-benzoyl)-thiazol-2-ylamino]-pentyl}-benzenesulfonamide | 456.4 (M − H+)− |
| 160. | [2-(5-Amino-pentylamino)-thiazol-5-yl]-o-tolyl-methanone; hydrochloride and 3-fluorobenzenesulfonyl chloride | 3-Fluoro-N-{5-[5-(2-methyl-benzoyl)-thiazol-2-ylamino]-pentyl}-benzenesulfonamide | 460.3 (M − H+)− |
| 161. | [2-(5-Amino-pentylamino)-thiazol-5-yl]-o-tolyl-methanone; hydrochloride and 2-chloro-5-(trifluoromethyl)benzene-sulfonyl chloride | 2-Chloro-N-{5-[5-(2-methyl-benzoyl)-thiazol-2-ylamino]-pentyl}-5-trifluoromethyl-benzenesulfonamide | 544.1 (M − H+)− |
| 162. | [2-(5-Amino-pentylamino)-thiazol-5-yl]-o-tolyl-methanone; hydrochloride and benzenesulfonyl chloride | N-{5-[5-(2-Methyl-benzoyl)-thiazol-2-ylamino]-pentyl}-benzenesulfonamide | 442.3 (M − H+)− |
| 163. | [2-(5-Amino-pentylamino)-thiazol-5-yl]-o-tolyl-methanone; hydrochloride and 3-methoxybenzenesulfonyl chloride | 3-Methoxy-N-{5-[5-(2-methyl-benzoyl)-thiazol-2-ylamino]-pentyl}-benzenesulfonamide | 472.1 (M − H+)− |
| 164. | [2-(5-Amino-pentylamino)-thiazol-5-yl]-(2-chloro-phenyl)-methanone; hydrochloride and 2-fluorobenzenesulfonyl chloride | N-{5-[5-(2-Chloro-benzoyl)-thiazol-2-ylamino]-pentyl}-2-fluoro-benzenesulfonamide | 480.2 (M − H+)− |
| 165. | [2-(5-Amino-pentylamino)-thiazol-5-yl]-(2-chloro-phenyl)-methanone; hydrochloride and 4-methoxybenzenesulfonyl chloride | N-{5-[5-(2-Chloro-benzoyl)-thiazol-2-ylamino]-pentyl}-4-methoxy-benzenesulfonamide | 492.2 (M − H+)− |
| 166. | [2-(5-Amino-pentylamino)-thiazol-5-yl]-(2-chloro-phenyl)-methanone; hydrochloride and 2 thiophenesulfonyl chloride | Thiophene-2-sulfonic acid {5-[5-(2-chloro-benzoyl)-thiazol-2-ylamino]-pentyl}-amide | 468.1 (M − H+)− |
| 167. | [2-(5-Amino-pentylamino)-thiazol-5-yl]-(2-chloro-phenyl)-methanone; hydrochloride and 6-methoxy-m-toluenesulfonyl chloride | N-{5-[5-(2-Chloro-benzoyl)-thiazol-2-ylamino]-pentyl}-2-methoxy-5-methyl-benzenesulfonamide | 506.2 (M − H+)− |

-continued

| Ex. | Educts | Name | Mass analysis |
|---|---|---|---|
| 168. | [2-(5-Amino-pentylamino)-thiazol-5-yl]-(2-chloro-phenyl)-methanone; hydrochloride and 4-fluorobenzenesulphonyl chloride | N-{5-[5-(2-Chloro-benzoyl)-thiazol-2-ylamino]-pentyl}-4-fluorobenzenesulfonamide | 480.3 (M − H⁺)⁻ |
| 169. | [2-(5-Amino-pentylamino)-thiazol-5-yl]-(2-chloro-phenyl)-methanone; hydrochloride and 2-methylbenzenesulphonyl chloride | N-{5-[5-(2-Chloro-benzoyl)-thiazol-2-ylamino]-pentyl}-2-methyl-benzenesulfonamide | 476.2 (M − H⁺)⁻ |
| 170. | [2-(5-Amino-pentylamino)-thiazol-5-yl]-(2-chloro-phenyl)-methanone; hydrochloride and 3-fluorobenzenesulphonyl chloride | N-{5-[5-(2-Chloro-benzoyl)-thiazol-2-ylamino]-pentyl}-3-fluoro-benzenesulfonamide | 480.3 (M − H⁺)⁻ |
| 171. | [2-(5-Amino-pentylamino)-thiazol-5-yl]-(2-chloro-phenyl)-methanone; hydrochloride and 2-chloro-5-(trifluoromethyl)-benzenesulfonyl chloride | 2-Chloro-N-{5-[5-(2-chloro-benzoyl)-thiazol-2-ylamino]-pentyl}-5-trifluoromethyl-benzenesulfonamide | 564.0 (M − H⁺)⁻ |
| 172. | [2-(5-Amino-pentylamino)-4-methyl-thiazol-5-yl]-o-tolyl-methanone hydrochloride and benzenesulphonyl chloride | N-{5-[4-Methyl-5-(2-methyl-benzoyl)-thiazol-2-ylamino]-pentyl}-benzenesulfonamide | 458.1 MH+ |
| 173. | [2-(5-Amino-pentylamino)-4-methyl-thiazol-5-yl]-o-tolyl-methanone hydrochloride and 2-methylbenzenesulphonyl chloride | 2-Methyl-N-{5-[4-methyl-5-(2-methyl-benzoyl)-thiazol-2-ylamino]-pentyl}-benzenesulfonamide | 472.3 MH+ |
| 174. | [2-(5-Amino-pentylamino)-4-methyl-thiazol-5-yl]-o-tolyl-methanone hydrochloride and 2-fluorobenzenesulphonyl chloride | 2-fluoro-N-{5-[4-methyl-5-(2-methyl-benzoyl)-thiazol-2-ylamino]-pentyl}-benzenesulfonamide | 476.3 MH+ |
| 175. | [2-(5-Amino-pentylamino)-4-methyl-thiazol-5-yl]-o-tolyl-methanone hydrochloride and 3-fluorobenzenesulphonyl chloride | 3-Fluoro-N-{5-[4-methyl-5-(2-methyl-benzoyl)-thiazol-2-ylamino]-pentyl}-benzenesulfonamide | 476.2 MH+ |
| 176. | [2-(5-Amino-pentylamino)-4-methyl-thiazol-5-yl]-o-tolyl-methanone hydrochloride and 4-fluorobenzenesulphonyl chloride | 4-Fluoro-N-{5-[4-methyl-5-(2-methyl-benzoyl)-thiazol-2-ylamino]-pentyl}-benzenesulfonamide | 476.2 MH+ |
| 177. | [2-(5-Amino-pentylamino)-4-methyl-thiazol-5-yl]-o-tolyl-methanone hydrochloride and 6-methoxy-m-toluenesulfonyl chloride | 2-Methoxy-5-methyl-N-{5-[4-methyl-5-(2-methyl-benzoyl)-thiazol-2-ylamino]-pentyl}-benzenesulfonamide | 502.3 MH+ |
| 178. | [2-(5-Amino-pentylamino)-4-methyl-thiazol-5-yl]-o-tolyl-methanone hydrochloride and 3-methoxybenzenesulfonyl chloride | 3-Methoxy-N-{5-[4-methyl-5-(2-methyl-benzoyl)-thiazol-2-ylamino]-pentyl}-benzenesulfonamide | 488.3 MH+ |
| 179. | [2-(5-Amino-pentylamino)-4-methyl-thiazol-5-yl]-o-tolyl-methanone hydrochloride and 4-methoxybenzenesulfonyl chloride | 4-Methoxy-N-{5-[4-methyl-5-(2-methyl-benzoyl)-thiazol-2-ylamino]-pentyl}-benzenesulfonamide | 488.3 MH+ |
| 180. | [2-(2-Amino-ethylamino)-thiazol-5-yl]-o-tolyl-methanone; hydrochloride and 2-thiophenylsulfonyl chloride | Thiophene-2-sulfonic acid {2-[5-(2-methyl-benzoyl)-thiazol-2-ylamino]-ethyl}-amide | 406.2 [M − H]− |
| 181. | [2-(2-Amino-propylamino)-thiazol-5-yl]-o-tolyl-methanone; hydrochloride and 2,5-dimethoxyphenylsulfonyl chloride | 2,5-Dimethoxy-N-{3-[5-(2-methyl-benzoyl)-thiazol-2-ylamino]-propyl}-benzenesulfonamide | 474.1 [M − H]− |
| 182. | [2-(2-Amino-butylamino)-thiazol-5-yl]-o-tolyl-methanone; hydrochloride and 2-thiophenylsulfonyl chloride | Thiophene-3-sulfonic acid {4-[5-(2-methyl-benzoyl)-thiazol-2-ylamino]-butyl}-amide | 434.2 [M − H]− |
| 183. | [2-(5-Amino-pentylamino)-thiazol-5-yl]-o-tolyl-methanone; hydrochloride and 2,5-dimethoxyphenylsulfonyl chloride | 2,5-Dimethoxy-N-{5-[5-(2-methyl-benzoyl)-thiazol-2-ylamino]-pentyl}-benzenesulfonamide | 502.0 [M − H]− |
| 184. | [2-(2-Amino-ethylamino)-thiazol-5-yl]-o-tolyl-methanone; hydrochloride and 3-thiophenylsulfonyl chloride | Thiophene-3-sulfonic acid {2-[5-(2-methyl-benzoyl)-thiazol-2-ylamino]-ethyl}-amide | 406.2 [M − H]− |
| 185. | [2-(2-Amino-propylamino)-thiazol-5-yl]-o-tolyl-methanone; hydrochloride and 2,5-dimethylphenylsulfonyl chloride | 2,5-Dimethyl-N-{3-[5-(2-methyl-benzoyl)-thiazol-2-ylamino]-propyl}benzenesulfonamide | 442.2 [M − H]− |
| 186. | [2-(2-Amino-propylamino)-thiazol-5-yl]-o-tolyl-methanone; hydrochloride and 2-chloro-5-methoxyphenylsulfonyl chloride | 5-Chloro-2-methoxy-N-{3-[5-(2-methyl-benzoyl)-thiazol-2-ylamino]-propyl}-benzenesulfonamide | 478.0 [M − H]− |
| 187. | [2-(2-Amino-butylamino)-thiazol-5-yl]-o-tolyl-methanone; hydrochloride and 2-methylbenzenesulfonyl chloride | 2-Methyl-N-{4-[5-(2-methyl-benzoyl)-thiazol-2-ylamino]-butyl}-benzenesulfonamide | 442.2 [M − H]− |
| 188. | [2-(2-Amino-butylamino)-thiazol-5-yl]-o-tolyl-methanone; hydrochloride and 2-methyl-5-fluorobenzenesulfonyl chloride | 5-Fluoro-2-methyl-N-{4-[5-(2-methyl-benzoyl)-thiazol-2-ylamino]-butyl}-benzenesulfonamide | 460.2 [M − H]− |
| 189. | [2-(2-Amino-butylamino)-thiazol-5-yl]-o-tolyl-methanone; hydrochloride and 2-chloro-5-trifluoromethylbenzenesulfonyl chloride | 2-Chloro-N-{4-[5-(2-methyl-benzoyl)-thiazol-2-ylamino]-butyl}-5-trifluoromethyl-benzenesulfonamide | 530.0 [M − H]− |
| 190. | [2-(2-Amino-pentylamino)-thiazol-5-yl]-o-tolyl-methanone; hydrochloride and 2,5-dimethylphenylsulfonyl chloride | 2,5-Dimethyl-N-{5-[5-(2-methyl-benzoyl)-thiazol-2-ylamino]-pentyl}-benzenesulfonamide | 470.2 [M − H]− |
| 191. | [2-(2-Amino-propylamino)-thiazol-5-yl]-o-tolyl-methanone; hydrochloride and 4-trifluoromethyloxyphenylsulfonyl chloride | N-{3-[5-(2-Methyl-benzoyl)-thiazol-2-ylamino]-propyl}-4-trifluoromethoxy-benzenesulfonamide | 498.0 [M − H]− |
| 192. | [2-(2-Amino-butylamino)-thiazol-5-yl]-o-tolyl-methanone; hydrochloride and 4-fluorophenylsulfonyl chloride | 4-Fluoro-N-{4-[5-(2-methyl-benzoyl)-thiazol-2-ylamino]-butyl}-benzenesulfonamide | 446.2 [M − H]− |
| 193. | [2-(2-Amino-butylamino)-thiazol-5-yl]-o-tolyl-methanone; hydrochloride and 2,4-difluorophenylsulfonyl chloride | 2,4-Difluoro-N-{4-[5-(2-methyl-benzoyl)-thiazol-2-ylamino]-butyl}-benzenesulfonamide | 464.1 [M − H]− |
| 194. | [2-(2-Amino-pentylamino)-thiazol-5-yl]-o-tolyl-methanone; hydrochloride and 4-trifluoromethyloxyphenylsulfonyl chloride | N-{5-[5-(2-Methyl-benzoyl)-thiazol-2-ylamino]-pentyl}-4-trifluoromethoxy-benzenesulfonamide | 525.9 [M − H]− |
| 195. | [2-(2-Amino-propylamino)-thiazol-5-yl]-o-tolyl-methanone; hydrochloride and 2-chloro-5-trifluoromethylbenzenesulfonyl chloride | 2-Chloro-N-{3-[5-(2-methyl-benzoyl)-thiazol-2-ylamino]-propyl}-4-trifluoromethyl-benzenesulfonamide | 516.0 [M − H]− |
| 196. | [2-(2-Amino-butylamino)-thiazol-5-yl]-o-tolyl-methanone; hydrochloride and 2-fluorophenylsulfonyl chloride | 2-Fluoro-N-{4-[5-(2-methyl-benzoyl)-thiazol-2-ylamino]-butyl}-benzenesulfonamide | 446.1 [M − H]− |
| 197. | [2-(2-Amino-butylamino)-thiazol-5-yl]-o-tolyl-methanone; hydrochloride and 5-chlorothiophenyl-2-sulfonyl chloride | 5-Chloro-thiophene-2-sulfonic acid {4-[5-(2-methyl-benzoyl)-thiazol-2-ylamino]-butyl}-amide | 468.0 [M − H]− |

-continued

| Ex. | Educts | Name | Mass analysis |
|---|---|---|---|
| 198. | [2-(2-Amino-pentylamino)-thiazol-5-yl]-o-tolyl-methanone; hydrochloride and 2-chloro-5-trifluoromethylbenzenesulfonyl chloride | 2-Chloro-N-{5-[5-(2-methyl-benzoyl)-thiazol-2-ylamino]-pentyl}-4-trifluoromethyl-benzenesulfonamide | 544.0 [M − H]− |
| 199. | [2-(2-Amino-propylamino)-thiazol-5-yl]-o-tolyl-methanone; hydrochloride and 2-thiophenesulfonyl chloride | Thiophene-3-sulfonic acid {3-[5-(2-methyl-benzoyl)-thiazol-2-ylamino]-propyl}-amide | 420.1 [M − H]− |
| 200. | [2-(2-Amino-propylamino)-thiazol-5-yl]-o-tolyl-methanone; hydrochloride and 2-methyl-5-fluorobenzenesulfonyl chloride | 5-Fluoro-2-methyl-N-{3-[5-(2-methyl-benzoyl)-thiazol-2-ylamino]-propyl}-benzenesulfonamide | 446.2 [M − H]− |
| 201. | [2-(2-Amino-butylamino)-thiazol-5-yl]-o-tolyl-methanone; hydrochloride and 3-fluorophenylsulfonyl chloride | 3-Fluoro-N-{4-[5-(2-methyl-benzoyl)-thiazol-2-ylamino]-butyl}-benzenesulfonamide | 446.1 [M − H]− |
| 202. | [2-(2-Amino-butylamino)-thiazol-5-yl]-o-tolyl-methanone; hydrochloride and 2-methoxy-5-methylphenylsulfonyl chloride | 2-Methoxy-5-methyl-N-{4-[5-(2-methyl-benzoyl)-thiazol-2-ylamino]-butyl}-benzenesulfonamide | 475.1 [M − H]− |
| 203. | [2-(2-Amino-pentylamino)-thiazol-5-yl]-o-tolyl-methanone; hydrochloride and 2-thiophenesulfonyl chloride | Thiophene-3-sulfonic acid {5-[5-(2-methyl-benzoyl)-thiazol-2-ylamino]-pentyl}-amide | 448.1 [M − H]− |
| 204. | [2-(2-Amino-pentylamino)-thiazol-5-yl]-o-tolyl-methanone; hydrochloride and 2-methyl-5-fluorophenylsulfonyl chloride | 5-Fluoro-2-methyl-N-{5-[5-(2-methyl-benzoyl)-thiazol-2-ylamino]-pentyl}-benzenesulfonamide | 474.1 [M − H]− |
| 205. | [2-(2-Amino-ethylamino)-thiazol-5-yl]-o-tolyl-methanone; hydrochloride and 2-methoxy-5-chlorophenylsulfonyl chloride | 5-Chloro-2-methoxy-N-{2-[5-(2-methyl-benzoyl)-thiazol-2-ylamino]-ethyl}-benzenesulfonamide | 464.0 [M − H]− |
| 206. | [2-(2-Amino-propylamino)-thiazol-5-yl]-o-tolyl-methanone; hydrochloride and 2,4-difluorophenylsulfonyl chloride | 2,4-Difluoro-N-{3-[5-(2-methyl-benzoyl)-thiazol-2-ylamino]-propyl}-benzenesulfonamide | 450.2 [M − H]− |
| 207. | [2-(2-Amino-butylamino)-thiazol-5-yl]-o-tolyl-methanone; hydrochloride and 2,5-dimethylphenylsulfonyl chloride | 2,5-Dimethyl-N-{4-[5-(2-methyl-benzoyl)-thiazol-2-ylamino]-butyl}-benzenesulfonamide | 456.3 [M − H]− |
| 208. | [2-(2-Amino-butylamino)-thiazol-5-yl]-o-tolyl-methanone; hydrochloride and 2,5-dimethoxyphenylsulfonyl chloride | 2,5-Dimethoxy-N-{4-[5-(2-methyl-benzoyl)-thiazol-2-ylamino)-butyl}-benzenesulfonamide | 488.1 [M − H]− |
| 209. | [2-(2-Amino-pentylamino)-thiazol-5-yl]-o-tolyl-methanone; hydrochloride and 2,4-difluorophenylsulfonyl chloride | 2,4-Difluoro-N-{5-[5-(2-methyl-benzoyl)-thiazol-2-ylamino]-pentyl}-benzenesulfonamide | 478.1 [M − H]− |
| 210. | [2-(2-Amino-propylamino)-thiazol-5-yl]-o-tolyl-methanone; hydrochloride and 5-chlorothiophenyl-2-sulfonyl chloride | 5-Chloro-thiophene-2-sulfonic acid {3-[5-(2-methyl-benzoyl)-thiazol-2-ylamino]-propyl}-amide | 454.2 [M − H]− |
| 211. | [2-(2-Amino-butylamino)-thiazol-5-yl]-o-tolyl-methanone; hydrochloride and 4-methoxyphenylsulfonyl chloride | 4-Methoxy-N-{4-[5-(2-methyl-benzoyl)-thiazol-2-ylamino]-butyl}-benzenesulfonamide | 458.2 [M − H]− |
| 212. | [2-(2-Amino-butylamino)-thiazol-5-yl]-o-tolyl-methanone; hydrochloride and 2-methoxy-5-chlorophenylsulfonyl chloride | 5-Chloro-2-methoxy-N-{4-[5-(2-methyl-benzoyl)-thiazol-2-ylamino]-butyl}-benzenesulfonamide | 492.0 [M − H]− |
| 213. | [2-(2-Amino-pentylamino)-thiazol-5-yl]-o-tolyl-methanone; hydrochloride and 5-chlorothiophenyl-2-sulfonyl chloride | 5-Chloro-thiophene-2-sulfonic acid {5-[5-(2-methyl-benzoyl)-thiazol-2-ylamino]-pentyl}-amide | 482.1 [M − H]− |
| 214. | [2-(2-Amino-butylamino)-thiazol-5-yl]-o-tolyl-methanone; hydrochloride and 2-thiophenylsulfonyl chloride | Thiophene-2-sulfonic acid {4-[5-(2-methyl-benzoyl)-thiazol-2-ylamino]-butyl}-amide | 434.2 [M − H]− |
| 215. | [2-(2-Amino-butylamino)-thiazol-5-yl]-o-tolyl-methanone; hydrochloride and 3-methoxyphenylsulfonyl chloride | 3-Methoxy-N-{4-[5-(2-methyl-benzoyl)-thiazol-2-ylamino]-butyl}-benzenesulfonamide | 458.2 [M − H]− |
| 216. | [2-(2-Amino-butylamino)-thiazol-5-yl]-o-tolyl-methanone; hydrochloride and 4-trifluoromethyloxy-phenylsulfonyl chloride | N-{4-[5-(2-Methyl-benzoyl)-thiazol-2-ylamino]-butyl}-4-trifluoromethoxy-benzenesulfonamide | 512.1 [M − H]− |
| 217. | [2-(3-Methylamino-propylamino)-thiazol-5-yl]-o-tolyl-methanone; hydrochloride and 2-thiophenylsulfonyl chloride | Thiophene-2-sulfonic acid methyl-{3-[5-(2-methyl-benzoyl)-thiazol-2-ylamino]-propyl}-amide | 434.2 [M − H]− |
| 218. | [2-(3-Methylamino-propylamino)-thiazol-5-yl]-o-tolyl-methanone; hydrochloride and 3-methoxyphenylsulfonyl chloride | 3-Methoxy-N-methyl-N-{3-[5-(2-methyl-benzoyl)-thiazol-2-ylamino]-propyl}-benzenesulfonamide | 458.2 [M − H]− |
| 219. | [2-(3-Methylamino-propylamino)-thiazol-5-yl]-o-tolyl-methanone; hydrochloride and 2-chloro-4-trifluoromethyl-phenylsulfonyl chloride | 2-Chloro-N-methyl-N-{3-[5-(2-methyl-benzoyl)-thiazol-2-ylamino]-propyl}-4-trifluoromethyl-benzenesulfonamide | 530.0 [M − H]− |
| 220. | [2-(3-Methylamino-propylamino)-thiazol-5-yl]-o-tolyl-methanone; hydrochloride and 2-methylphenylsulfonyl chloride | 2,N-Dimethyl-N-{3-[5-(2-methyl-benzoyl)-thiazol-2-ylamino]-propyl}-benzenesulfonamide | 442.2 [M − H]− |
| 221. | [2-(3-Methylamino-propylamino)-thiazol-5-yl]-o-tolyl-methanone; hydrochloride and 2-methyl-5-fluorophenyl-sulfonyl chloride | 5-Fluoro-2,N-dimethyl-N-{3-[5-(2-methyl-benzoyl)-thiazol-2-ylamino]-propyl}-benzenesulfonamide | 460.2 [M − H]− |
| 222. | [2-(3-Methylamino-propylamino)-thiazol-5-yl]-o-tolyl-methanone; hydrochloride and 2-chloro-5-trifluoromethyl-phenylsulfonyl chloride | 2-Chloro-N-methyl-N-{3-[5-(2-methyl-benzoyl)-thiazol-2-ylamino]-propyl}-5-trifluoromethyl-benzenesulfonamide | 530.0 [M − H]− |
| 223. | [2-(3-Methylamino-propylamino)-thiazol-5-yl]-o-tolyl-methanone; hydrochloride and 4-fluorophenylsulfonyl chloride | 4-Fluoro-N-methyl-N-{3-[5-(2-methyl-benzoyl)-thiazol-2-ylamino]-propyl}-benzenesulfonamide | 446.1 [M − H]− |
| 224. | [2-(3-Methylamino-propylamino)-thiazol-5-yl]-o-tolyl-methanone; hydrochloride and 2,4-difluorophenylsulfonyl chloride | 2,4-Difluoro-N-methyl-N-{3-[5-(2-methyl-benzoyl)-thiazol-2-ylamino]-propyl}-benzenesulfonamide | 464.3 [M − H]− |
| 225. | [2-(3-Methylamino-propylamino)-thiazol-5-yl]-o-tolyl-methanone; hydrochloride and 2-fluorophenylsulfonyl chloride | 2-Fluoro-N-methyl-N-{3-[5-(2-methyl-benzoyl)-thiazol-2-ylamino]-propyl}-benzenesulfonamide | 446.1 [M − H]− |
| 226. | [2-(3-Methylamino-propylamino)-thiazol-5-yl]-o-tolyl-methanone; hydrochloride and 5-chlorothiophenyl-2-sulfonyl chloride | 5-Chloro-thiophene-2-sulfonic acid methyl-{3-[5-(2-methyl-benzoyl)-thiazol-2-ylamino]-propyl}-amide | 468.0 [M − H]− |
| 227. | [2-(3-Methylamino-propylamino)-thiazol-5-yl]-o-tolyl-methanone; hydrochloride and 3-fluorophenylsulfonyl chloride | 3-Fluoro-N-methyl-N-{3-[5-(2-methyl-benzoyl)-thiazol-2-ylamino]-propyl}-benzenesulfonamide | 446.1 [M − H]− |
| 228. | [2-(3-Methylamino-propylamino)-thiazol-5-yl]-o-tolyl-methanone; hydrochloride and 2-methoxy-5-methylphenyl-sulfonyl chloride | 2-Methoxy-5,N-dimethyl-N-{3-[5-(2-methyl-benzoyl)-thiazol-2-ylamino]-propyl}-benzenesulfonamide | 472.1 [M − H]− |
| 228. | [2-(3-Methylamino-propylamino)-thiazol-5-yl]-o-tolyl-methanone; hydrochloride and 4-chlorophenylsulfonyl chloride | 4-Chloro-N-methyl-N-{3-[5-(2-methyl-benzoyl)-thiazol-2-ylamino]-propyl}-benzenesulfonamide | 462.1 [M − H]− |

-continued

| Ex. | Educts | Name | Mass analysis |
|---|---|---|---|
| 230. | [2-(3-Methylamino-propylamino)-thiazol-5-yl]-o-tolyl-methanone; hydrochloride and 2,5-methylphenylsulfonyl chloride | 2,5,N-Trimethyl-N-{3-[5-(2-methyl-benzoyl)-thiazol-2-ylamino]-propyl}-benzenesulfonamide | 456.3 [M − H]− |
| 231. | [2-(3-Methylamino-propylamino)-thiazol-5-yl]-o-tolyl-methanone; hydrochloride and 4-nitrophenylsulfonyl chloride | N-Methyl-N-{3-[5-(2-methyl-benzoyl)-thiazol-2-ylamino]-propyl}-4-nitro-benzenesulfonamide | 472.9 [M − H]− |
| 232. | [2-(3-Methylamino-propylamino)-thiazol-5-yl]-o-tolyl-methanone; hydrochloride and 4-methoxyphenylsulfonyl chloride | 4-Methoxy-N-methyl-N-{3-[5-(2-methyl-benzoyl)-thiazol-2-ylamino]-propyl}-benzenesulfonamide | 458.2 [M − H]− |
| 233. | [2-(3-Methylamino-propylamino)-thiazol-5-yl]-o-tolyl-methanone; hydrochloride and 2-methoxy-5-chlorophenyl-sulfonyl chloride | 5-Chloro-2-methoxy-N-methyl-N-{3-[5-(2-methyl-benzoyl)-thiazol-2-ylamino]-propyl}-benzenesulfonamide | 492.1 [M − H]− |

Example A

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example C

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example D

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example E

Injection solutions can have the following composition:

| | |
|---|---|
| Compound of formula I | 3.0 mg |
| Gelatin | 150.0 mg |
| Phenol | 4.7 mg |
| Water for injection solutions | ad 1.0 ml |

What is claimed is:

1. A compound of formula I

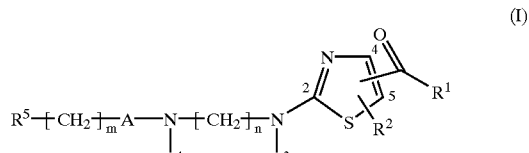

(I)

wherein $R^1$ is aryl or heteroaryl;

$R^2$ is hydrogen, alkyl or cycloalkyl;

$R^3$ is hydrogen, alkyl or cycloalkyl;

$R^4$ is hydrogen, alkyl or cycloalkyl;

$R^5$ is alkyl, cycloalkyl, aryl, heteroaryl;

$R^6$ is hydrogen, alkyl or cycloalkyl;

A is —C(O)—; —S(O)$_2$—; —N(R$^6$)—C(O)— or —O—C(O)—;

n is 2 to 6;

m is zero to 2;

and pharmaceutically acceptable salts and esters thereof.

2. The compound according to claim 1, wherein $R^2$ is hydrogen or methyl.

3. The compound according to claim 1, wherein $R^3$ is hydrogen.

4. The compound according to claim 1, wherein $R^4$ is hydrogen.

5. The compound according to claim 1, wherein $R^5$ is phenyl, or heteroaryl which is thiophenyl, both optionally substituted with one to three substituents independently selected from alkyl, alkoxy, halogen, haloalkyl, haloalkoxy and nitro.

6. The compound according to claim 1, wherein $R^6$ is hydrogen.

7. The compound according to claim 1, wherein $R^1$ is heteroaryl which is pyridinyl, or aryl which is unsubstituted phenyl or phenyl substituted with one to three substituents independently selected from alkyl alkoxy, halogen and haloalkyl.

8. The compound according to claim 1, wherein A is —S(O)$_2$—.

9. The compound according to claim 1, wherein A is —C(O)—.

10. The compound according to claim 1, wherein A is —N(R$^6$)C(O)—.

11. The compound according to claim 1, wherein A is —O—C(O)—.

12. The compound according to claim 1, wherein n is 3 to 5.

13. The compound according to claim 1, wherein A is zero.

14. The compound according to claim 1,
wherein
$R^1$ is heteroaryl which is pyridinyl, or aryl which is unsubstituted phenyl or phenyl substituted with one to three substituents independently selected from alkyl, alkoxy, halogen and haloalkyl;
$R^2$ is hydrogen or methyl;
$R^3$ is hydrogen;
$R^4$ is hydrogen;
$R^5$ is alkyl, phenyl or heteroaryl which is thiophenyl, wherein phenyl and thiophenyl are each optionally substituted with one to three substituents independently selected from alkyl, alkoxy, halogen, haloalkyl, haloalkoxy and nitro;
$R^6$ is hydrogen;
n is 3 to 5; and
m is zero.

15. The compound according to claim 14, wherein A is —S(O)$_2$— or —C(O)—.

16. The compound in accordance with claim 1, selected from
thiophene-2-sulfonic acid {3-[5-(2-methyl-benzoyl)-thiazol-2-ylamino]-propyl}-amide;
2-methoxy-5-methyl-N-{3-[5-(2-methyl-benzoyl)-thiazol-2-ylamino]-propyl}-benzenesulfonamide;
2-chloro-N-{3-[5-(2-methyl-benzoyl)-thiazol-2-ylamino]-propyl}-5-trifluoromethyl-benzenesulfonamide;
thiophene-2-sulfonic acid {3-[5-(2-chloro-benzoyl)-thiazol-2-ylamino]-propyl}-amide;
N-{3-[5-(2-chloro-benzoyl)-thiazol-2-ylamino]-propyl}-2-methoxy-5-methylbenzenesulfonamide;
2-chloro-N-{3-[5-(2-chloro-benzoyl)-thiazol-2-ylamino]-propyl}-5-trifluoromethylbenzenesulfonamide;
2-chloro-N-{3-[4-(2-methyl-benzoyl)-thiazol-2-ylamino]-propyl}-5-trifluoromethylbenzenesulfonamide;
2-methoxy-5-methyl-N-{3-[4-(2-methyl-benzoyl)-thiazol-2-ylamino]-propyl}-benzenesulfonamide;
2-methoxy-5-methyl-N-{5-[5-(pyridine-2-carbonyl)-thiazol-2-ylamino]-pentyl}-benzenesulfonamide;
4-methoxy-N-{5-[5-(2-methyl-benzoyl)-thiazol-2-ylamino]-pentyl}-benzenesulfonamide;
2-methoxy-5-methyl-N-{5-[5-(2-methyl-benzoyl)-thiazol-2-ylamino]-pentyl}-benzenesulfonamide;
2-methyl-N-{5-[5-(2-methyl-benzoyl)-thiazol-2-ylamino]-pentyl}-benzenesulfonamide;
3-fluoro-N-{5-[5-(2-methyl-benzoyl)-thiazol-2-ylamino]-pentyl}-benzenesulfonamide;
2-chloro-N-{5-[5-(2-methyl-benzoyl)-thiazol-2-ylamino]-pentyl}-5-trifluoromethyl-benzenesulfonamide;
N-{5-[5-(2-chloro-benzoyl)-thiazol-2-ylamino]-pentyl}-2-fluoro-benzenesulfonamide;
N-{5-[5-(2-chloro-benzoyl)-thiazol-2-ylamino]-pentyl}-2-methoxy-5-methylbenzenesulfonamide;
N-{5-[5-(2-chloro-benzoyl)-thiazol-2-ylamino]-pentyl}-2-methyl-benzenesulfonamide;
2-methoxy-5-methyl-N-{5-[4-methyl-5-(2-methyl-benzoyl)-thiazol-2-ylamino]-pentyl}-benzenesulfonamide;
2-chloro-N-{3-[5-(2-methyl-benzoyl)-thiazol-2-ylamino]-propyl}-4-trifluoromethylbenzenesulfonamide;
5-fluoro-2-methyl-N-{3-[5-(2-methyl-benzoyl)-thiazol-2-ylamino]-propyl}-benzenesulfonamide;
2,5-dimethoxy-N-{4-[5-(2-methyl-benzoyl)-thiazol-2-ylamino]-butyl}-benzenesulfonamide;
5-chloro-thiophene-2-sulfonic acid {3-[5-(2-methyl-benzoyl)-thiazol-2-ylamino]-propyl}-amide;
thiophene-2-sulfonic acid {4-[5-(2-methyl-benzoyl)-thiazol-2-ylamino]-butyl}-amide;
thiophene-2-sulfonic acid methyl-{3-[5-(2-methyl-benzoyl)-thiazol-2-ylamino]-propyl}-amide;
2,N-dimethyl-N-{3-[5-(2-methyl-benzoyl)-thiazol-2-ylamino]-propyl}-benzenesulfonamide;
5-chloro-thiophene-2-sulfonic acid methyl-{3-[5-(2-methyl-benzoyl)-thiazol-2-ylamino]-propyl}-amide;
4-chloro-N-methyl-N-{3-[5-(2-methyl-benzoyl)-thiazol-2-ylamino]-propyl}-benzenesulfonamide; and
N-methyl-N-{3-[5-(2-methyl-benzoyl)-thiazol-2-ylamino]-propyl}-4-nitro-benzenesulfonamide.

17. A pharmaceutical composition comprising a compound according to claim 1 or a pharmaceutically acceptable salt or ester thereof, and a pharmaceutically acceptable carrier.

18. A pharmaceutical composition comprising a compound according to claim 14 or a pharmaceutically acceptable salt or ester thereof, and a pharmaceutically acceptable carrier.

19. A method for treatment of obesity in a patient in need of treatment, comprising administering a compound according to claim 1 or a pharmaceutically acceptable salt or ester thereof to said patient, in an amount of from about 0.1 mg to 20 mg per kg body weight per day.

20. The method according to claim 19, wherein said compound, salt or ester thereof is administered in an amount of from about 0.5 mg to 4 mg per kg body weight per day.

21. A method for treatment of obesity in a patient in need of treatment, comprising administering a compound according to claim 14 or a pharmaceutically acceptable salt or ester thereof to said patient, in an amount of from about 0.1 mg to 20 mg per kg body weight per day.

22. The method according to claim 21, wherein said compound, salt or ester thereof is administered in an amount of from about 0.5 mg to 4 mg per kg body weight per day.

* * * * *

UNITED STATES PATENT AND TRADEMARK OFFICE
CERTIFICATE OF CORRECTION

PATENT NO. : 6,686,381 B2
DATED : February 3, 2004
INVENTOR(S) : Patrizio Mattei et al.

It is certified that error appears in the above-identified patent and that said Letters Patent is hereby corrected as shown below:

<u>Column 75,</u>
Line 24, "… wherein A is zero." should read -- … wherein m is zero. --
Line 46, "…or -C(O)-" should be -- …or -O-C(O)- --

Signed and Sealed this

Eighteenth Day of May, 2004

JON W. DUDAS
*Acting Director of the United States Patent and Trademark Office*